US007595433B2

(12) United States Patent
Jankowski et al.

(10) Patent No.: US 7,595,433 B2
(45) Date of Patent: Sep. 29, 2009

(54) MODULATIONS OF AMINO ACID AND SUGAR CONTENT IN PLANTS

(75) Inventors: Boris Jankowski, Santa Monica, CA (US); Kenneth A. Feldmann, Newbury Park, CA (US); Steven Craig Bobzin, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 169 days.

(21) Appl. No.: 11/225,903

(22) Filed: Sep. 13, 2005

(65) Prior Publication Data

US 2006/0059582 A1   Mar. 16, 2006

Related U.S. Application Data

(60) Provisional application No. 60/610,356, filed on Sep. 14, 2004.

(51) Int. Cl.
*C12N 15/82* (2006.01)
(52) U.S. Cl. .................................. 800/284; 800/287
(58) Field of Classification Search ........................ None
See application file for complete search history.

(56) References Cited

U.S. PATENT DOCUMENTS

| | | | |
|---|---|---|---|
| 4,987,071 A | 1/1991 | Cech et al. | |
| 5,204,253 A | 4/1993 | Sanford et al. | |
| 5,254,678 A | 10/1993 | Haseloff et al. | |
| 5,538,880 A | 7/1996 | Lundquist et al. | |
| 5,591,616 A | 1/1997 | Hiei et al. | |
| 6,197,561 B1 * | 3/2001 | Martino-Catt et al. | 800/278 |
| 6,329,571 B1 | 12/2001 | Hiei | |
| 6,423,885 B1 | 7/2002 | Waterhouse et al. | |
| 2004/0031072 A1 | 2/2004 | La Rosa et al. | |
| 2005/0009187 A1 * | 1/2005 | Shinozaki et al. | 435/468 |
| 2005/0246785 A1 | 11/2005 | Cook et al. | |
| 2006/0041952 A1 | 2/2006 | Cook | |
| 2006/0059582 A1 | 3/2006 | Jankowski et al. | |

FOREIGN PATENT DOCUMENTS

| | | |
|---|---|---|
| EP | 1033405 A2 * | 6/2000 |
| EP | 1033405 A2 | 9/2000 |
| WO | WO 99/32619 | 7/1999 |
| WO | WO 01/35725 | 5/2001 |
| WO | WO0159163 | 8/2001 |
| WO | WO 01/75164 | 10/2001 |
| WO | WO 02/15675 | 2/2002 |
| WO | WO 02/46449 | 6/2002 |
| WO | WO 03/013227 | 2/2003 |
| WO | 03/04491 * | 5/2003 |
| WO | WO03044190 | 5/2003 |
| WO | WO2004035798 | 4/2004 |
| WO | WO 2006/005023 | 12/2006 |

OTHER PUBLICATIONS

Yanagisawa, et al., (2004 ) Metabolic engineering with Dof1 transcription factor in plants: Improved nitrogen assimilation and growth under low-nitrogen conditions. PNAS vol. 101 No. 20 7833-7838.*
Van Eenennaam et al (2004) Elevation of seed alpha-tocopherol levels using plant-based transcription factors targeted to an endogenous locus. Metab Eng. Apr;6(2):101.*
Yanagisawa S. The Dof family of plant transcription factors. Trends Plant Sci. Dec. 2002;7(12):555-60.*
Broun, et al (1998) Catalytic Plasticity Of Fatty Acid Modification Enzymes Underlying Chemical Diversity Of Plant Lipids. Science 282(13) 1315-1317.*
Broun, et al (1998) Catalytic Plasticity Of Fatty Acid Modification Enzymes Underlying Chemical Diversity Of Plant Lipids. Science 282(13) 1315-1317.*
Galweiler et al Technical advance: the DNA-binding activity of gal4 is inhibited by methylation of the gal4 binding site in plant chromatin. Plant J. Jul. 2000;23(1):143-57.*
Zhang et al, Synthetic Zinc Finger Transcription Factor Action at an Endogenous Chromosomal Site activation of the human erythropoietin gene J. Biol. Chem., vol. 275, Issue 43, 33850-33860, Oct. 27, 2000.*
Lazar et al. (1988) Transforming Growth Factor A: Mutation Of Aspartic Acid 47 And Leucine 48 In Different Biological Activities. Molec. & Cell. Biol. 8(3)1247-52.*
Doerks, et al (1998) Protein Annotation: Detective Work For Function Prediction TIG 14(6) 248-250.*
Haas, et al, (2002) Genome Biology 3: 1-12.*
Alexandrov et al, (2006) Features of Arabidopsis Genes and Genome Discovered using Full-length cDNAs vol. 60 1 69-85.*
Benfrey and Chua 1990 Science 250(4983): 959-966.*
U.S. Appl. No. 60/505,689, filed Sep. 23, 2003, Cook et al.
U.S. Appl. No. 60/518,075, filed Nov. 6, 2003, Pennell et al.
U.S. Appl. No. 60/544,771, filed Feb. 13, 2004, Cook et al.
U.S. Appl. No. 60/558,869, filed Apr. 1, 2004, Cook et al.
U.S. Appl. No. 60/583,691, filed Jun. 30, 2004, Alexandrov et al.
U.S. Appl. No. 60/637,140, filed Dec. 16, 2004, K. Feldmann.
U.S. Appl. No. 11/172,703, filed Jun. 30, 2005, Pennell et al.
Wilson, et al., Assessing Annotation Transfer for Genomics: Quantifying the Relations between Protein Sequence, Structure and Function through Traditional and Probabilistic Scores; J. Mol. Biol. 297, pp. 233-249, (2000).
Tian, et al., How Well is Enzyme Function Conserved as a Function of Pairwise Sequence Identity?; J. Mol. Biol. (2003) 333, pp. 863-882.
Xu, et al., Microarray-based analysis of gene expression in very large gene families: the cytochrome P450 gene superfamily of *Arabidopsis thaliana*; Gene 272 (2001), pp. 61-74.
Paquette, et al., Intron-Exon Organization and Phylogeny in a Large Superfamily, the Paralogous Cytochrome P450 Genes of *Arabidopsis thaliana*; DNA and Cell Biology, vol. 19, No. 5, (2000), pp. 307-317.
Brummell, et al., Inverted repeat of a heterologous 3'-untranslated region for high-efficiency, high-throughput gene silencing; The Plant Journal (2003) 33, pp. 793-800.

(Continued)

*Primary Examiner*—David H Kruse
(74) *Attorney, Agent, or Firm*—Fish & Richardson P.C.

(57) ABSTRACT

Methods and materials for modulating lysine, glucose, fructose, galactose and leucine content in plants are disclosed.

24 Claims, 8 Drawing Sheets

OTHER PUBLICATIONS

Mizutani, et al., Cytochrome p450 superfamily in *Arabidopsis thaliana*: isolation of cDNAs, Differential Expression, and RFLP mapping of multiple cytochromes P450; Plant Molecular Biology (1998) 37, pp. 39-52.

NSF 2010: Functional Genomics Arabidopsis P450s; Retrieved from the Internet: URL:http://arabidopsis-p450.biotec.uiuc.edu/.

Sanger Institute: Changes to Pfam [Retrieved from the Internet:] URL:http://www.sanger.ac.uk/Pfam.

Sonnhammer, et al., Pfam: multiple sequence alignments and HMM-profiles of protein domains; Nucleic Acids Research, vol. 26, (1998), pp. 320-322.

Sonnhammer, et al., Pfam: A Comprehensive Database of Protein Domain Families Based on Seed Alignments; Proteins: Structure, Function, and Genetics, vol. 28 (1997), pp. 405-420.

Bateman, et al., Pfam 3.1: 1313 multiple alignments and profile HMMs match the majority of proteins; Nucleic Acids Research, vol. 27, (1999), pp. 260-262.

Salomon, et al., Genetic identification of functions of TR-DNA transcripts in octopine crown galls; The EMBO Journal, vol. 3, No. 1 pp. 141-146 (1984).

Herrera-Estrella, et al., Chimeric genes as dominant selectable markers in plant cells; The EMBO Journal, vol. 2, No. 6, pp. 987-995 (1983).

Escudero, et al., T-DNA transfer in meristematic cells of maize provided with intracellular Agrobacterium, The Plant Journal, 10(2), pp. 355-560 (1996).

Ishida, et al., High efficiency transformation of maize (Zea mays L.) mediated by Agrobacterium tumefaciens, Nature Biotechnology, vol. 14, pp. 745-750 (1996).

May, et al., Generation of Transgenic Banana (*Musa acuminate*) Plants via Agrobacterium-Mediated Transformation, Bio/Technology, vol. 13, pp. 486-492 (1995).

Armaleo, et al., Current Genetics 17:97 (1990).

Lam, et al., Site-specific mutations alter in vitro factor binding and change promoter expression pattern in transgenic plants, Pro. Natl. Acad. Sci. USA, vol. 86, pp. 7890-7894 (1989).

Conkling, et al., Plant Physiol . 93:1203-1211 (1990).

Bustos, et al., Regulation of β-Glucuronidase Expression in Transgenic Tobacco Plants by an A/T-Rich, cis-Acting Sequence Found Upstream of a French Bean β-Phaseolin Gene, The Plant Cell, vol. 1, pp. 839-853 (1989).

Riggs, et al., Cotyledon Nuclear Proteins Bind to DNA Fragments Harboring Regulatory Elements of Phytohemagglutinin Genes, The Plant Cell, vol. 1(6), pp. 609-621 (1989).

Baerson, et al., Developmental regulation of an acyl carrier protein gene promoter in vegetative and reproductive tissues, Plant Molecular Biology, 22(2), pp. 255-267 (1993).

Slocombe, et al., Plant Physiol 104(4):167-176 (1994).

Chen, et al., Functional analysis of regulatory elements in a plant embryo-specific gene, Proc. Natl. Acad. Sci. USA, vol. 83, pp. 8560-8564 (1986).

Hong, et al., Promoter sequences from two different Brassica napus tapetal oleosin-like genes direct tapetal expression of β-glucuronidase in transgenic Brassica plants, Plant Molecular Biology, 34(3), pp. 549-555 (1997).

Zheng, et al., Mol. Cell Biol. 13-5829-5842 (1993).

Yamamoto, et al., The Promoter of a Pine Photosynthetic Gene Allows Expression of a β-Glucuronidase Reporter Gene in Transgenic Rice Plants in a Light-Independent but Tissue Specific Manner, Plant Cell Physiol., 35(5), pp. 773-778 (1994).

Fejes et al., A 268 bp upstream sequence mediates the circadian clock-regulated transcription of the wheat Cab-1 gene in transgenic plants, Plant Molecular Biology, 15, pp. 921-932 (1990).

Lubberstedt, et al., Plant Physiol. 104:997-1006 (1994).

Luan, et al., Plant Cell 4:971-981 (1992).

Matsuoka, et al., Tissue-specific light-regulated expression directed by the promoter of a C4 gene, maize pyruvate,orthophosphate dikinase, in a C3 plant, rice, Proc. Natl. Acad. Sci. USA, vol. 90, pp. 9586-9590 (1993).

Cerdan, et al., A 146 bp fragment of the tobacco Lhcb1 *2 promoter confers very-low-fluence, low-fluence and high-irradiance responses of phytochrome to a minimal CaMV 35S promoter, Plant Molecular Biology, 33, pp. 245-255 (1997).

Truernit, et al., The promoter of the *Arabidopsis thaliana* SUC2 sucrose-H+ symporter gene directs expression of β-glucuronidase to the phloem: Evidence for phloem loading and unloading by SUC2, Planta, 196, pp. 564-570 (1995).

Fromm, et al., The Plant Cell 1:977-984 (1989).

Summerton and Weller, Morpholino Antisense Oligomers: Design, Preparation, and Properties, Antisense & Nucleic Acid Drug Development., 7, pp. 187-195 (1997).

Hyrup, et al., Peptide Nucleic Acids (PNA): Synthesis, Properties and Potential Applications, Bioorganic & Medicinal Chemistry, vol. 4, No. 1, pp. 5-23 (1996).

Bechtold, et al., In planta Agrobacterium mediated gene transfer by infiltration of adult *Arabidopsis thaliana* plants, C.R. Acad. Sci. Paris, 316, pp. 1194-1199 (1993).

Werck-Reichhart, et al., Cytochromes P450; The Arabidopsis Book, (2002). Retrieved from the Internet: URL:http://www.arabidopsis.org/servlets/TairObject?type=publication&id=501681274.

Sato, et al., Structural analysis of *Arabidopsis thaliana* chromosome 3. 1. Sequence features of the regions of 4,504,864 bp covered by sixty PI and TAC clones; DNA Res. 7(2), 131-135 (2000). Retrieved from the Internet: URL:http://www.ncbi.nlm.nih.gov/entrez/viewer.fcgi?db—protein&val=13878384.

AtMYB23 MYB transcription factor target down-regulation; Jul. 6, 2004. Retrieved from the Internet: URL:http://www.ncbi.nlm.nih.gov/projects/geo/gds/gds_browse.cgi?gds=694.

Matsui, et al., NimbleGen 60mer Arabidopsis array; National Institute of Advanced Industrial Science and Technology (AIST); Jul. 7, 2004. Retrieved from the Internet: URL:http://www.ncbi.nlm.nih.gov/projects/geo/query/acc.cgi?acc=GPL1323.

Perriman, et al., Effective ribozyme delivery in plant cells, Proc. Natl. Acad. Sci. USA, vol. 92(13), pp. 6175-6179 (1995).

Rivera, et al., Genomic evidence for two functionality distinct gene classes; Proc. Natl. Acad. Sci. USA, vol. 95, pp. 6239-6244 (1998).

Pan, et al., GAL4 transcription factor is not a "zinc finger" but forms a Zn(II)2Cys6 binuclear cluster, Proc. Natl. Acad. Sci. USA, vol. 87, pp. 2077-2081 (1990).

International Search Report from International Application No. PCT/US05/32680.

Van Eenennaam, et al., Elevation of seed χ-tocopherol levels using plant-based transcription factors targeted to an endogenous locus, Metabolic Engineering 6, (2004), pp. 101-108.

Yanagisawa, et al., Metabolic engineering with Dof1 transcription factor in plants: Improved nitrogen assimilation and growth under low-nitrogen conditions, PNAS, May 18, 2004, vol. 101, No. 20, pp. 7833-7838.

Zhang, et al., Synthetic Zinc Finger Transcription Factor Action at an Endogenous Chromosomal Site, The Journal of Biological Chemistry, Oct. 27, 2000, vol. 275, No. 43, pp. 33850-33860.

Yanagisawa, S., The Dof family of plant transcription factors, Trends in Plant Science, Dec. 2002, vol. 7, No. 12; pp. 555-560.

GenBank Accession No. CAA16567 dated Nov. 14, 2006, 2 pages.
GenBank Accession No. CAA19798 dated Nov. 14, 2006, 2 pages.
GenBank Accession No. CAB79237 dated Nov. 14, 2006, 2 pages.
GenBank Accession No. AAN72006 dated Nov. 19, 2002, 2 pages.
GenBank Accession No. AAP21371 dated Apr. 25, 2003, 2 pages.
GenBank Accession No. Q9LTM2 dated Nov. 28, 2006, 2 pages.
GenBank Accession No. Q9LTM1 dated Nov. 28, 2006, 3 pages.
GenBank Accession No. BAB02441 dated Feb. 14, 2004, 2 pages.
GenBank Accession No. BAB02440 dated Feb. 14, 2004, 2 pages.
GenBank Accession No. AAK25981 dated Sep. 18, 2002, 2 pages.
GenBank Accession No. AAK64138 dated Sep. 18, 2002, 2 pages.
GenBank Accession No. NP 194013 dated Jun. 9, 2006, 2 pages.
GenBank Accession No. NP 974594 dated Jun. 9, 2006, 2 pages.
GenBank Accession No. NP 189251 dated Jun. 9, 2006, 2 pages.
GenBank Accession No. NP 189250 dated Jun. 9, 2006, 2 pages.

* cited by examiner

Figure 1

[Sequence alignment figure - full page content]

Figure 1 (Continued)

| | | | | | |
|---|---|---|---|---|---|
| SEQ-ID-NO-12 | VHRYSDKHDC | PYDYHTAARD | VI AKANPVVK | ADKLEKI | 173 |
| SEQ-ID-NO-4 | SHRYPEKXEC | SFDFKXVGRD | AI AKANPVI K | ADKVERI | 172 |
| LEAD-SEQ-ID-NO-2 | DHRYPETHDC | SFDFKEVGRG | EI AKANPVVK | ADKI QRF | 176 |
| SEQ-ID-NO-3 | EHRYPETHDC | SFDFKEVGRG | EI AKANPVVK | ADKI QRF | 176 |
| SEQ-ID-NO-7 | THRYTEAHDC | TFDYKKAGRD | QI AKQNPVVL | AEKI NKI | 161 |
| SEQ-ID-NO-10 | MHRYADAHDC | KFDYKQAGRE | AQQNPVVK | ADKVTRF | 161 |
| SEQ-ID-NO-6 | THRYPEQHAC | EFDFKGMGRE | QI AKANPVVK | GEKLDKI | 158 |
| SEQ-ID-NO-11 | IHRYPGTTCL | CF | | | 137 |
| SEQ-ID-NO-8 | RHRYSDAHEC | SFDYKAAGRE | EI AKANPVI K | AAKI KI | 157 |
| SEQ-ID-NO-9 | EHRYTDRHDC | SYDYKTVGRE | AI ARENPVVK | AAKI VKV | 137 |
| | | | | | |
| Consensus | -HRY-D-HDC | SFDYK-VGRD | -I AKANPVVK | ADKI -KI | 187 |

Figure 2

| | | | | | | |
|---|---|---|---|---|---|---|
| SEQ-ID-NO-24 | ------- | ------- | ------- | MD----LL | YTVAALVTFA | SLLAKSKRK | 24 |
| SEQ-ID-NO-25 | ------- | --SQPQWPP | LLQLSAAVLF | ------- | FLLPLLYLLF | LRGSNGEVRG | 45 |
| SEQ-ID-NO-19 | ------- | -SLPPQWLS | IL----AV | ------- | FLLPLLF--- | LLLFRGKDDN | 36 |
| SEQ-ID-NO-20 | ------- | GGSVPQQWQT | CL----LV | ------- | LLPVLLVSYY | LLTSRSRNRS | 44 |
| Lead-SEQ-ID-NO-15 | ------- | ------- | ------- | --M---SI | SLYFLLLPL | FLJFFKKLSP | 23 |
| SEQ-ID-NO-17 | ------- | ------- | ------- | --M---SI | FLCFLLLLPL | FLVFYKRLLP | 23 |
| SEQ-ID-NO-28 | ------- | ------- | ---MSF | TD----HH | YLLLILFLP | ILVYTIRRKI | 27 |
| SEQ-ID-NO-16 | ------- | ------- | ----MA | ILC----VS | LLFLALALTF | FLLKLNEKRE | 26 |
| SEQ-ID-NO-18 | ------- | ------- | ------- | ML----SF | TVFVFLVTLF | TLSLVKQLRK | 24 |
| SEQ-ID-NO-26 | ------- | ------- | -MKMLEQNP | QY----LY | FESLFLVTLP | LYKMLTLKKT | 32 |
| SEQ-ID-NO-27 | ------- | ------- | ----MV | SL----SY | FLIALLCTLP | FLLFLNRMRR | 26 |
| SEQ-ID-NO-21 | ------- | ------- | --MALPPLLL | SP----LP | SLLVLALLS | SLLLAGRKAR | 32 |
| SEQ-ID-NO-23 | ------- | ------- | ----MTVSI | TA----AV | QLFLLLLLL | QLLFVHHKTK | 29 |

Consensus ------- ------- ------- -L------ FL-LLL-LL- --LLF----R- 50

| | | | | | | |
|---|---|---|---|---|---|---|
| SEQ-ID-NO-24 | PKKN----- | LPPGPPRLPI | GNLHQLG-E | KPHRAMVELS | KLYGPLMSLK | 67 |
| SEQ-ID-NO-25 | RQGNSASAPS | LPGPCRQLPV | GNLHQLQI-G | RPHRYFQAVS | RRYGPVVQVQ | 94 |
| SEQ-ID-NO-19 | QKKGL----K | LPGPRQLPL | GNLHQLG-G | QPYVDFWKMA | KKYGPVMYLQ | 81 |
| SEQ-ID-NO-20 | RSGKLGGAPR | LPGPAQLPI | GNLHQLG-P | LPHKNRELA | RRYGPVMQLR | 93 |
| Lead-SEQ-ID-NO-15 | SKGK------K | LPGPLLPI | GNLHQLG-K | SLHRSFHKLS | QNYGPVMFH | 66 |
| SEQ-ID-NO-17 | SKGK------K | LPGPISLPI | GNLHQLG-K | SLHRSFYKLS | QEYGPVMFL | 66 |
| SEQ-ID-NO-28 | SSTKS-----K | LPGPCPPKLPL | GNLHQMG-T | LPHQSLHALS | VKYGPLMLK | 72 |
| SEQ-ID-NO-16 | KKPN------ | LPPSPPNLPI | GNLHQLG-N | LPHRSLRSLA | NELGPLLLH | 69 |
| SEQ-ID-NO-18 | PTAEK---RRL | LPPGPRKLPF | GNLHQLG-T | LPHQSLQYLS | NKHGPLMFLK | 71 |
| SEQ-ID-NO-26 | PLKN------ | LPPSPPQYPI | GNLHQLG-P | DPQASLRDLA | QKYGPLMFLK | 75 |
| SEQ-ID-NO-27 | SYSGK----T | PPPSPPKLPV | CNLHQLG-L | YPHRYLQSLS | RRYGPLMQLH | 71 |
| SEQ-ID-NO-21 | GGSAT---WK | LPGPPKLPV | GHLHLGSS | LLHRSLWELS | KKHGPLMHLK | 79 |
| SEQ-ID-NO-23 | PKTKC-----R | SPPGPPPLPV | GNLHQLS-L | LLHQSLYRLS | KTHGPIFKLS | 74 |

Consensus --K------ LPPGPP-LPI GNLHQLG--- -PHRSL---LS KKYGPLM-LK 100

Figure 2 (Continued)

| | | | | | |
|---|---|---|---|---|---|
| SEQ-ID-NO-24 | LGSVT TVVAT | SVET VRDVLK | TYDLECCSRP | YMTYPARITY | NLKDLVFSPY | 117 |
| SEQ-ID-NO-25 | LGGVRT VVH | SPEAAEDVLR | TNDVHCCSRP | PSPGPRMLSY | NYLDVAFAPY | 144 |
| SEQ-ID-NO-19 | LGRCPTVVLS | STETSKELMK | DRDVCCSRP | LSVGPGQLSY | NFLDVAFSPY | 131 |
| SEQ-ID-NO-20 | LGTVPTVVVS | SAEAAREVLK | VHDVDCCSRP | ASPGPKRLSY | DLKNVGFAPY | 143 |
| Lead-SEQ-ID-NO-15 | FGVVPVVVVS | TREAAAEEVLK | THDLETCTRP | KLTATKLFSY | NYKDIGFAPY | 116 |
| SEQ-ID-NO-17 | FGVVPVVVES | TKEAAAEEVLK | THDLETCTRP | KLSATGLFTY | NFKDIGFAPY | 116 |
| SEQ-ID-NO-28 | LGQIPTLIVS | SADMAREI MK | THDHI FASRP | SLMTAGI LY | GSMDVVFAPY | 122 |
| SEQ-ID-NO-16 | LGHI PTLIVS | TAEIAEEILK | THDLI FASRP | STTAARRI FY | DCTDVAFSPY | 119 |
| SEQ-ID-NO-18 | LGSI PTLVVS | SADAMAREI LK | THDLVFSGRP | SLYAANRLGY | CST VSFAPY | 120 |
| SEQ-ID-NO-26 | FGTVPPVL VVS | SAEAAREILK | NHDSVFSGRP | YSSVANKI FY | NGKDMVFARY | 125 |
| SEQ-ID-NO-27 | FGSVPPVL VVS | SPEAAREI MK | THDLVFADRP | KMSI ANRLFF | NNRDVAFITQY | 121 |
| SEQ-ID-NO-21 | FGRVPVVVVS | SPEMAKEVLK | NQDI VFSNRP | SLI SFSKFSY | GLSDVAFIPY | 129 |
| SEQ-ID-NO-23 | LGRVPVL VLS | SPSLAKQVLK | THDLAFCSRA | STVSFKEYTY | DGCDVAGAPY | 124 |
| Consensus | LG-VPTVVVS | S-E-A-EVLK | THDL--CSRP | -M-----LSY | N--DVAFAPY | 150 |

| | | | | | |
|---|---|---|---|---|---|
| SEQ-ID-NO-24 | DKYWRQVRKL | TVVELYTAKR | VQSFRHIREE | EVASFVRFNK | QAASEE-TV | 166 |
| SEQ-ID-NO-25 | SDYWREMRKL | FVVELISVSR | VRSFAYARAA | EVARLVDTLA | ASPPGV--PV | 192 |
| SEQ-ID-NO-19 | SDYWREMRKL | FLFELLSMRR | VQTFWYAREE | OMDKMI EJLD | GAYPN---PV | 178 |
| SEQ-ID-NO-20 | GEYWREMRKL | FALELLSMRR | VKAACYAREQ | EMDRLVADLD | RAAASKA-SI | 192 |
| Lead-SEQ-ID-NO-15 | GDDWREMRKL | AMLELFSSKK | LKAFRYIREE | ESELLVKKVT | KSAETRT-MV | 165 |
| SEQ-ID-NO-17 | GEDWREMRKL | AMLELFSSKK | LKAFRYIREE | ESAQTQT-LV | ESAQTQT-LV | 165 |
| SEQ-ID-NO-28 | GEHWROMRKL | CVNHLLSPKA | VQSFRRMHEE | EVATMVAKI S | EVSSSSG-VV | 171 |
| SEQ-ID-NO-16 | GEYWROVRKL | CVLELLSI KR | VNSYRSLREE | EVGLMMERI S | QSCSIGE-AV | 168 |
| SEQ-ID-NO-18 | GEYWREMRKL | CVLELLSNKR | VQSFEAVRFE | EVDLLVQNLE | LSHG----PV | 166 |
| SEQ-ID-NO-26 | TEYWRQVKS | MI LELLSNKR | VNSFHYVREE | ETSI MVEKIM | NSHSK--VA | 172 |
| SEQ-ID-NO-27 | GEYWRQI RS | CVLQLLSNKR | VQSFRRVREE | EMERVTKLI C | QLGSSSTPV | 171 |
| SEQ-ID-NO-21 | GERWRQLRKL | CTVELLSTRK | NSFRDI RKE | EISI MVEKI M | SHVRASS-MV | 178 |
| SEQ-ID-NO-23 | GDSWRNLRKI | FVLNLLSSKK | LTSFRLVQEE | EI EGMI SSI R | TRSDI NA-TV | 173 |
| Consensus | GEYWR-MRKL | -VLELLSSKR | VQSFRYVREE | EVE-MVE-I - | QS------V | 200 |

Figure 2 (Continued)

```
SEQ·ID·NO-24         NLSQKILKMS GSVICRIGFG INLE---GSK LENTYQEIIV QAFEVLG-SL  212
SEQ·ID·NO-25         DLSCALYQLL DGIIGTVAFG KGYGAAQWST ERAVFQDVLS ELLLVLG-SF  241
SEQ·ID·NO-19         NLTEKVFNMM DGIIGTIAFG RTTYA--QQE FRDGFVKVLA ATMDMLD-NF  225
SEQ·ID·NO-20         VLNDHVFALT DGIIGTVAFG NIYASK-QFA HKERFQHVLD DAMDMMA-SF  240
Lead·SEQ·ID·NO-15    DLRKALFSYT ASIVCRLAFG QNFHEC-DFV DMDKVEDLVL ESETNLG-SF  213
SEQ·ID·NO-17         DLRKALFSYT ASIVCRLAFG QNFHEC-DFV DMDKVEELVL ESETNLG-SF  213
SEQ·ID·NO-28         NMSETLNLFA SNAMLKAISR KLFR---DER RSRVICELNE ETAAILG-QF  217
SEQ·ID·NO-16         NLSELLLLLS SGTITRVAFG KKYEG--EEE RKNKFADLAT ELTTLMG-AF  215
SEQ·ID·NO-18         NLSELTLSLT NNIVCRIALG KRNRS--CAD DANKVSEMLK ETQAMLG-CF  213
SEQ·ID·NO-26         NLTELLIEVT GNVVCRVSVG -------SGD KVDSYKILIL EIMDMLGYSR  215
SEQ·ID·NO-27         NLSELLLSLT NDVVCRVTLG KKYGGGNGSE EVDKLKEMLT ELQNLMG-IS  220
SEQ·ID·NO-21         NLSELLLSLS CNMTCRSAFG SGF----DDG GDIQLHDMLR EAQEELS-GL  223
SEQ·ID·NO-23         NITEFVVRLA NNITFRVAFG YRSEG--EYG EKSRFQRLLE SGNDTVA-SF  220

Consensus            NLSE-LLSL- -NI-CRVAFG K--------- --DKFQELL- E--DMLG-SF  250

SEQ·ID·NO-24         AAVDYFP--- VICTIIDRIT GLHAKCEKVF HGIDSFFDQA IQRHIDDPSI  259
SEQ·ID·NO-25         SFEDFFPSSA LARW-ADALA GVERRRRRIF RQVDGFLDSV IDKHLEPERL  290
SEQ·ID·NO-19         HAENFFP--- VVGRFIDSLT GALAKRQRTF TDVDRYFEKV IEQHLDPNRP  272
SEQ·ID·NO-20         SAEDFFP--N AAGRLADRLS GFLARRERIF NELDVFFEKV IDQHMDPARP  288
Lead·SEQ·ID·NO-15    AFTDFFP--A GLGWVIDRIS GQHSELHKAF ARLSNFFQHV IDDHLKPGQS  261
SEQ·ID·NO-17         AFIDFFP--A GLGWAIDRIS GQHSRLHKAF ARLSNFFQHV IDDHLKPWQS  261
SEQ·ID·NO-28         SVSDFMP--- LLAW-FDMVF GVGARAKKTA RLWDRVLHEI IEDCRNRRDS  263
SEQ·ID·NO-16         FVGDYFP--- SFAW-VDVLT GMDARLKRNH GELDAFVDHV IDDHLLSRKA  261
SEQ·ID·NO-18         FPVDFFP--- RLGW-LNKFS GLENRLEKIF REMDNFYDQV IKEHIADNSS  259
SEQ·ID·NO-26         SIEDFFP--- LLGW-VDWLT GLRGKVAEAA KGVDTFLECV LKEHLSTTGS  261
SEQ·ID·NO-27         PVWEFIP--- WLNW-TRRFD GVDQRVDRIV KAFDGFLESV IQEHKERDGD  266
SEQ·ID·NO-21         FLSDYLP--- LLGW-VDRLS GMRSRLERAF LKLDSIYQRR IDYHQDRLRQ  269
SEQ·ID·NO-23         YVGDYFP--- GLGW-LDKIT GKLGKMKRNA RDLDEFYQEV IDAHMKDGRK  266

Consensus            S--DFFP--- -LGW-IDRL- G---RLER-F -ELD-FF--V ID-HL---R-  300
```

| | | | | | | |
|---|---|---|---|---|---|---|
| SEQ-ID-NO-24 | LKETFRISPL | VPVLVPRVAA | KDLKIAGYDV | PEKTMHVNM | WAVHMSPSIM | 401 |
| SEQ-ID-NO-25 | LKENFRLHPP | GNLLVPRQTM | QPCLIGGYNV | PSGTRVFNL | WAMGRGPMI | 436 |
| SEQ-ID-NO-19 | VKETFRKHPP | VPLLVPHFSM | KHCKIGGYDI | LPGTIYVNA | WAMGKDPTI | 416 |
| SEQ-ID-NO-20 | VKETLRLHPP | ATLLVPRETM | RDTTICGYDV | PANTRVFVNA | WAIGRDPASW | 433 |
| Lead-SEQ-ID-NO-15 | EETFRLHPP | APLLLPRETM | SDLKIQGYNI | PKNTMEINT | YSIGRDPNCW | 406 |
| SEQ-ID-NO-17 | QETFRLHPP | APLLLPRETM | SDVKIQGYNI | PKNTMEINT | YAIGRDPNCW | 406 |
| SEQ-ID-NO-28 | KELILRLHPP | VPLLIPRESM | DHCEVQGFDI | PKQTRVJVNA | WSIGRDPNVM | 405 |
| SEQ-ID-NO-16 | IKETLRLHPV | APLLVPREST | RDVVIRGYH | PAKTRVFVNA | WAIGRDPKSW | 408 |
| SEQ-ID-NO-18 | VKEVLRLHPV | APLLVPREIT | ENCTLKGFEI | PAKTRVLVNA | KSIAMDPCCW | 405 |
| SEQ-ID-NO-26 | MKESMRLYFT | APLLVPREAR | ODIKFMGYDI | SSGTQVLVNA | WAIARDPLLW | 401 |
| SEQ-ID-NO-27 | IKESLRLHPP | VVLLVPREST | RDTNVLGYDI | ASGTRVLNA | WAIARDPSVM | 413 |
| SEQ-ID-NO-21 | IKETMRLHPP | APLLLPRETM | QHFKLNGYDI | LPKTMMYVNA | WAIGRDPNSM | 410 |
| SEQ-ID-NO-23 | VNETLRLHCP | LPLLVPRETI | QHCEINGYDV | SAKTRVLVNA | WAIGRDEDAM | 405 |
| | | | | | | |
| Consensus | IKETLRLHPP | APLLVPRE-M | QD-KI-GYDI | PS-TRV-VNA | WAIGRDP---W | 450 |
| | | | | | | |
| SEQ-ID-NO-24 | KDPETFNPER | FIDNQTDFKG | LNFELLPFGS | GRRMCPGMGM | GLAVVHITL | 451 |
| SEQ-ID-NO-25 | DNPEEFYPER | FEDRNMDFRG | SNFELVPFGS | CPGVAM | AVTSLELVVA | 486 |
| SEQ-ID-NO-19 | ENPEEYNPDR | FMNSEVDFRG | SDFELVPFGA | GRRICPGLAM | GTTAVKYILS | 466 |
| SEQ-ID-NO-20 | PAPDEFNPER | FVGSDVDYG | SHFELIPFGA | GRRICPGLTM | GETNVTFTLA | 483 |
| Lead-SEQ-ID-NO-15 | EKPNDFNPER | FIDSPVEYKG | QHYELLPFGA | GRRICPGMAT | GITIVELGL | 456 |
| SEQ-ID-NO-17 | TNPNEFLPER | FVDSPIDYKG | QHFELLPFGA | GRRICPGMAT | GMTIVELGL | 456 |
| SEQ-ID-NO-28 | EAPEEFRPER | FLDCAINFRG | HDFELLPFGA | GRRCPGMQF | AVSTLELALA | 455 |
| SEQ-ID-NO-16 | ENALEEFLPER | FVNNSVDFKG | QDFQLIPFGA | GRRGCPGIAF | GISSVEISLA | 458 |
| SEQ-ID-NO-18 | ENPNEFLPER | FLVSPIDFKG | QHFEMLPFGV | GRRGCPGVNF | AMPVVELALA | 455 |
| SEQ-ID-NO-26 | DKPEEFRPER | FLNSPIDYKG | FHYELLPFGA | GRRGCPGIQF | AMCINELVVA | 451 |
| SEQ-ID-NO-27 | ENPEEFLPER | FLDSSLDYKG | LHFELLPFGA | GRRGCPGATF | AVAIDELALA | 463 |
| SEQ-ID-NO-21 | GRPHVFDPER | FMHDSTEASG | ODFKLIPFGE | GRRICPGKNL | GMLMVELALA | 460 |
| SEQ-ID-NO-23 | ENPEEFNPDR | FVGSSLDYKG | ODFQFLPFGA | GRRICPGIQF | GVETVELALA | 455 |
| | | | | | | |
| Consensus | ENPEEF-PER | F---S-VD-KG | --FELIPFGA | GRRICPGM-- | G---VVEL-LA | 500 |

Figure 2 (Continued)

| | | | | | |
|---|---|---|---|---|---|
| SEQ-ID-NO-24 | NLLYRFDWKL | PNGMKAEELS | EENYGLCV | KKLPLEAPV | LTQWT----- | 496 |
| SEQ-ID-NO-25 | NLLYCFDWKL | PKGMKEEDID | MEEIGQSFR | RKVELFVPV | KHEQYQLMGH | 536 |
| SEQ-ID-NO-19 | NLLYGWDYEM | PRGKFEDFP | LEEGGLTVH | NKQDMVIPK | KHKWD----- | 511 |
| SEQ-ID-NO-20 | NLLYCYDWAL | PGAMKPEDVS | MEETGALIFH | RKTPLVVVPT | KYKNRRAA-- | 531 |
| Lead-SEQ-ID-NO-15 | NVLYFFDWSL | PDGMKIEDID | MEEAGAFVVA | KKVPLELIPT | PHQW------ | 500 |
| SEQ-ID-NO-17 | NVLYFFDWSL | PYGMAIADIN | MEEAGAFVLA | KKVPLELVPV | LHY------- | 499 |
| SEQ-ID-NO-28 | NLVRSFDWEL | PDGMNNEDLG | MGDGPGLSAR | RRQSLLLVAK | PFLGLKCM-- | 503 |
| SEQ-ID-NO-16 | NLLYMFNWEL | PGDLTKEDLD | MSEAVGITVH | MKFPLQLVAK | RHLS------ | 502 |
| SEQ-ID-NO-18 | NLLFRFDWEL | PLGLGIQDLD | MEEAIGITIH | KKAHLMLKAT | PFCE------ | 499 |
| SEQ-ID-NO-26 | NLVHKFNFEL | PDGKRLEDLD | MTAASGITLR | KKSPLLVVAR | PFV------- | 494 |
| SEQ-ID-NO-27 | KLVHKFDFGL | PNGARMEELD | MSELSGMTVH | KKSPLLLLP | PIHAAP---- | 509 |
| SEQ-ID-NO-21 | NLLYSFDWHL | PPGMVKEDIS | MEEAPGVTVH | REYALCLMAT | KYDATTA--- | 507 |
| SEQ-ID-NO-23 | NLLYAFNWEL | PPGVERENID | MHEAPGLVTR | RATDLRLVAT | NYEEAN---- | 501 |

Consensus       NLLY-FDWEL  P-GMK-EDLD  MEEA-GLTV-  KK-PL-LVP-    -H------        550

| | |
|---|---|
| SEQ-ID-NO-24 | --- 496 |
| SEQ-ID-NO-25 | -N- 538 |
| SEQ-ID-NO-19 | --- 511 |
| SEQ-ID-NO-20 | --- 531 |
| Lead-SEQ-ID-NO-15 | --- 500 |
| SEQ-ID-NO-17 | --- 499 |
| SEQ-ID-NO-28 | --- 503 |
| SEQ-ID-NO-16 | --- 502 |
| SEQ-ID-NO-18 | --- 499 |
| SEQ-ID-NO-26 | --- 494 |
| SEQ-ID-NO-27 | --- 509 |
| SEQ-ID-NO-21 | --- 507 |
| SEQ-ID-NO-23 | --- 501 |

Consensus       ---       552

MODULATIONS OF AMINO ACID AND SUGAR CONTENT IN PLANTS

CROSS-REFERENCE TO RELATED APPLICATIONS

This application claims priority under 35 U.S.C. § 119 to U.S. Provisional Application No. 60/610,356, filed Sep. 14, 2004, incorporated herein by reference in its entirety.

TECHNICAL FIELD

This document relates to materials and methods for modulating amino acid and/or sugar content in plants.

BACKGROUND

An essential amino acid for an organism is an amino acid that cannot be synthesized by the organism from other available resources, and therefore must be supplied as part of its diet. Nine amino acids, including lysine and leucine, are generally regarded as essential for humans. Deficiencies of particular essential amino acids in certain major food crops have spurred efforts to improve the nutritional value of plants. One strategy to improve the nutritional value of plants relies upon traditional plant breeding methods. Another approach involves genetic manipulation of plant characteristics through the introduction of exogenous nucleic acids conferring a desirable trait.

SUMMARY

This document provides methods and materials related to modulating amino acid and/or sugar content in plants. For example, the present invention relates to materials and methods for expressing proteins that are capable of modulating the level of one or more amino acids and/or one or more sugars in plants. Modulation can include an increase relative to basal or native states (e.g., a control level). In other cases, modulation can include a decrease relative to basal or native states. In some cases, an amino acid-modulating protein can be a transcription factor. In other cases, an amino acid-modulating protein can be a cytochrome P450 protein.

In one embodiment, a method of modulating the level of at least one of lysine, glucose, fructose and galactose in a plant is provided. The method can include introducing into a plant cell an isolated nucleic acid comprising a nucleic acid sequence encoding a polypeptide having 80% or greater sequence identity to an amino acid sequence selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13 amino acid sequences, where a plant produced from the plant cell has a difference in the level of at least one of lysine, glucose, fructose and galactose compared to the corresponding level in a corresponding control plant that does not comprise the isolated nucleic acid. The percent identity can be 80%, 85%, 90%, 95% or greater.

In another embodiment, a method of modulating the level of leucine in a plant is provided. The method can include introducing into a plant cell an isolated nucleic acid comprising a nucleic acid sequence encoding a polypeptide having 80% or greater sequence identity to an amino acid sequence SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28, wherein a plant produced from the plant cell has a difference in the level of leucine compared to the level of leucine in a corresponding control plant that does not comprise the isolated nucleic acid. The percent identity can be 80%, 85%, 90%, 95% or greater.

In a further embodiment, a method of modulating the level of at least one of lysine, glucose, fructose, galactose and leucine in a plant is provided. The includes introducing into a plant cell: a) a first isolated nucleic acid comprising a nucleic acid sequence encoding a polypeptide comprising an amino acid sequence selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13; and b) a second isolated nucleic acid comprising a nucleic acid sequence encoding a polypeptide comprising an amino acid sequence selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28, wherein a plant produced from the plant cell has a difference in the level of at least one of lysine, glucose, fructose, galactose and leucine as compared to the corresponding level in a corresponding control plant that does not comprise the first and second isolated nucleic acids.

In another aspect, a method of producing a plant having a modulated level of at least one of lysine, glucose, fructose and galactose is provided. The method includes a) introducing into a plant cell an isolated nucleic acid comprising a nucleic acid sequence encoding a polypeptide having 80% or greater sequence identity to an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13; and b) growing a plant from the plant cell. The percent identity can be 80%, 85%, 90%, 95% or greater.

In another aspect, a method of producing a plant having a modulated level of leucine is provided. The said method includes a) introducing into a plant cell an isolated nucleic acid comprising a nucleic acid sequence encoding a polypeptide having 80% or greater sequence identity to an amino acid sequence selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28; and b) growing a plant from the plant cell. The percent identity can be 80%, 85%, 90%, 95% or greater.

In a further aspect, a method of producing a plant having a modulated level of at least one of lysine, glucose, fructose, galactose and leucine is provided. The method includes a) introducing into a plant cell a first isolated nucleic acid comprising a nucleic acid sequence encoding a polypeptide comprising an amino acid sequence selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13; and a second isolated nucleic acid comprising a nucleic acid sequence encoding a polypeptide comprising an amino acid sequence selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28; and b) growing a plant from the plant cell.

Recombinant vectors are also provided. A recombinant vector can include a described polynucleotide operably linked to a regulatory region. A regulatory region can be a promoter. A promoter can be, without limitation, a cell-specific promoter, a tissue specific promoter, a constitutive promoter or a broadly expressing promoter.

A plant or plant cell can be a member of one of the following genera: *Abies, Agrostis, Allium, Alseodaphne, Anacardium, Andropogon, Arachis, Apium, Aragrostis, Ascophyllum, Asparagus, Atropa, Avena, Beilschmiedia, Brassica, Capsicum, Carthamus, Chondrus, Chicorium, Citrus, Citrullus, Cocculus, Cocos, Coffea, Corylus, Cracilaria, Croton, Crypthecodinium, Cucumis, Cucurbita, Cunninghamia, Cuphea, Cynodon, Daucus, Dianthus, Duguetia, Elaeis, Enteromorpha, Euphoria, Festuca, Festulolium, Ficus, Fragaria, Fucus, Glaucium, Glycine, Gossypium, Haematococcus, Helianthus, Heterocallis, Hevea, Himanthalia, Hordeum, Hyoscyamus, Lactuca, Landolphia, Lemna, Linum, Litsea, Lolium, Lycopersicon, Lupinus, Majorana, Malus, Manihot, Medicago, Musa, Nicotiana, Odontella, Olea, Oryza, Palmaria, Panicum, Pannesetum, Papaver, Parthenium, Persea, Petunia, Phaseolus, Phleum, Phoenix, Picea, Pinus, Pistacia, Pisum, Poa, Populus* sect., *Porphyra, Prunus, Pseudotsuga Pyrus, Raphanus, Ricinus, Rosa, Rubus, Saccharum, Salix, Schizochytrium, Secale, Senecio, Sinapis, Solanum, Sorghum, Spinacia, Spirulina, Stephania, Triticum, Tagetes, Theobroma, Trifolium, Trigonella, Ulva, Undaria, Vaccinium, Vicia, Vigna, Vinca, Vitis,* and *Zea.*

A plant or plant cell can be a member of one of the following species: *Ananus comosus, Arabidopsis thaliana, Brassica rapa, Brassica napus, Brassica oleracea, Bixa orellana, Calendula officinalis, Cinnamommum camphora, Coffea arabica, Glycine max, Glycyrrhiza glabra, Gossypium hirsutum, Gossypium herbaceum, Lactuca sativa, Lycopersicon esculentum, Mentha piperita, Mentha spicata, Musa paradisiaca, Oryza Sativa, Parthenium argentatum, Rosmarinus officinalis, Solanum tuberosum, Theobroma cacao, Triticum aestivum, Vitis vinifera,* and *Zea mays.*

A plant or plant cell can be one of the following: alfalfa, amaranth, apple, beans (including kidney beans, lima beans, dry beans, green beans), broccoli, cabbage, carrot, castor bean, chick peas, cherry, clover, coffee, cotton, cottonseed, crambe, eucalyptus, flax, grape, grapefruit, lemon, lentils, lettuce, linseed, mango, melon (e.g., watermelon, cantaloupe), mustard, orange, peanut, peach, pear, peas, pepper, plum, poplar, potato, rapeseed (high erucic acid and canola), safflower, sesame, soybean, spinach, strawberry, sugarbeet, sunflower, tea, tomato, as well as monocots such as banana, barley, date palm, field corn, garlic, millet, oat, oil palm, onion, pineapple, popcorn, rice, rye, sorghum, sudangrass, sugarcane, sweet corn, switchgrass, turf grasses, wheat, fir, pine, spruce, brown seaweeds, green seaweeds, red seaweeds, and microalgae.

Plant cells are having modulated levels of one or more amino acids or sugars are also featured. In one embodiment, a plant cell can include an exogenous nucleic acid comprising a nucleic acid sequence encoding a polypeptide having 80% or greater sequence identity to an amino acid sequence selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13; where expression of the exogenous nucleic acid in a plant produced from the plant cell is effective to result in a difference in the level of at least one of lysine, glucose, fructose and galactose as compared to the corresponding level in a corresponding control plant that does not comprise the exogenous nucleic acid. The percent identity can be 80%, 85%, 90%, 95% or greater.

In another embodiment, a plant cell can include an exogenous nucleic acid comprising a nucleic acid sequence encoding a polypeptide having 80% or greater sequence identity to an amino acid sequence selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28, where expression of the exogenous nucleic acid in a plant produced from the plant cell is effective to result in a difference in the level of leucine as compared to the level of leucine in a corresponding control plant that does not comprise the exogenous nucleic acid. The percent identity can be 80%, 85%, 90%, 95% or greater.

In a further embodiment, a plant cell can include first exogenous nucleic acid comprising a nucleic acid sequence encoding a polypeptide comprising an amino acid sequence selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13, and a second exogenous nucleic acid comprising a nucleic acid sequence encoding a polypeptide comprising an amino acid sequence selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28; where expression of the first exogenous nucleic acid and the second exogenous nucleic acid in a plant produced from said plant cell is effective to result in a difference in the level of at least one of lysine, glucose, fructose, galactose and leucine as compared to the corresponding level in a corresponding control plant that does not comprise the first exogenous nucleic acid and the second exogenous nucleic acid.

Plant cells can include recombinant vectors that can include a described polynucleotide operably linked to a regulatory region. A regulatory region can be a promoter. A promoter can be, without limitation, a cell-specific promoter, a tissue specific promoter, a constitutive promoter or a broadly expressing promoter.

Transgenic plants having modulated levels of one or more amino acids or sugars are also provided. The modulation of levels of one or more amino acids can be in vegetative tissues of a transgenic plant. In one aspect, a transgenic plant can include a plant having a modulated level of at least one of lysine, glucose, fructose and galactose as compared to a corresponding control plant, the transgenic plant comprising an exogenous nucleic acid comprising a nucleic acid sequence encoding a polypeptide having 80% or greater sequence identity to an amino acid sequence selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13. The percent identity can be 80%, 85%, 90%, 95% or greater.

In another aspect, a transgenic plant can include a plant having a modulated level of leucine as compared to a corresponding control plant, the transgenic plant comprising an exogenous nucleic acid comprising a nucleic acid sequence encoding a polypeptide having 80% or greater sequence identity to an amino acid sequence selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28. The percent identity can be 80%, 85%, 90%, 95% or greater.

In a further aspect, a transgenic plant can include a plant having a modulated level of at least one of lysine, glucose, fructose, galactose and leucine as compared to a corresponding control plant, said transgenic plant comprising a first exogenous nucleic acid comprising a nucleic acid sequence encoding a polypeptide comprising an amino acid sequence selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13, and a second exogenous nucleic acid comprising a nucleic acid sequence encoding a polypeptide comprising an amino acid sequence selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28.

Transgenic plants can include recombinant vectors that can include a described polynucleotide operably linked to a regulatory region. A regulatory region can be a promoter. A promoter can be, without limitation, a cell-specific promoter, a tissue specific promoter, a constitutive promoter or a broadly expressing promoter. The modulation of levels of one or more amino acids can be in vegetative tissues of a transgenic plant.

Also provided are plant products and articles of manufacture produced from the transgenic plants. In one embodiment, methods of producing one of more amino acids e.g. lysine, leucine, and one or more sugars, e.g. glucose, fructose, and galactose are provided. The method includes extracting at least one of lysine, glucose, fructose, galactose and leucine from the transgenic plant. Such amino acids and sugars can be extracted from plant tissues, seeds or roots. In another embodiment, plant tissues are provided, including fruit and seeds.

In still another embodiment, articles of manufacture are provided. Articles of manufacture can include, without limitation, foods, food products, and extracts made from the transgenic plants including vegetative tissue and seeds. In another aspect, an article of manufacture including seeds in the appropriate packaging material is also provided.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is an alignment setting forth amino acid sequence of CeresClone 13832 and certain homologs or orthologs.

FIG. 2 is an alignment setting forth amino acid sequences of cDNA ID 23530177 and certain homologs or orthologs.

DETAILED DESCRIPTION

The material and methods provided herein can be used to make a plant or plant cell having a modulated level of one or more amino acids, e.g., lysine and leucine, and/or a modulated level of one or more sugars, e.g., glucose, fructose, and galactose. Thus, methods for modulating one or more amino acid and/or sugar levels in a plant are provided. Methods are also provided for producing plants and plant cells having modulated levels of one or more amino acids and/or sugars. Methods for producing plant products including seeds, oils, and roots containing modulated levels of one or more amino acids and/or sugars are further provided. Such plants may be used to produce foodstuffs having increased nutritional content, which may benefit both food producers and consumers, or can be used as sources from which to extract one or more amino acids, e.g., lysine or leucine, or one or more sugars, e.g., glucose, fructose, and galactose.

I. Polypeptides and Polynucleotides

A. Polypeptides

Provided herein are amino acid-modulating polypeptides. An amino acid-modulating polypeptide can be effective for modulating the level of one or more amino acids in a plant or plant cell. Modulation in the level of an amino acid can be either an increase in the level of an amino acid or a decrease in the level of an amino acid, e.g., relative to the level in a control plant. An amino acid-modulating polypeptide can be a lysine modulating polypeptide. A lysine modulating polypeptide can also be effective, in some cases, for modulating the level of one or more sugars, for example, glucose, fructose, or galactose. In some cases, an amino acid-modulating polypeptide can be a leucine modulating polypeptide.

1. Lysine-Modulating Polypeptides.

A lysine modulating polypeptide can have the amino acid sequence of Ceres clone 13832 as set forth in FIG. 1 and in SEQ ID NO:2. Ceres clone 13832 (SEQ ID NO: 2) is predicted to be a zinc finger transcription factor. Transcription factors are a diverse class of proteins that regulate gene expression through specific DNA binding events. In particular, transcription factors are involved in the complex regulatory network of genes responsible for amino acid biosynthesis. Transcription factors include a number of characteristic structural motifs that mediate interactions with nucleic acids. Zinc finger motifs typically include one or more cysteine and histidine residues that can bind a zinc atom. Zinc finger motifs can serve as structural platforms for DNA binding.

Thus, a lysine-modulating polypeptide can be an *Arabidopsis* polypeptide having the amino acid sequence set forth in SEQ ID NO:2. Alternatively, a lysine-modulating polypeptide can be an ortholog, homolog, or variant of the polypeptide having the sequence set forth in SEQ ID NO:2. A lysine-modulating polypeptide, as described herein, can have an amino acid sequence with at least 35 percent sequence identity (e.g., 35 percent, 40 percent, 45 percent, 50 percent, 55 percent, 60 percent, 65 percent, 70 percent, 80 percent, 81 percent, 82 percent, 83 percent, 84 percent, 85 percent, 86 percent, 87 percent, 88 percent, 89 percent, 90 percent, 91 percent, 92 percent, 93 percent, 94 percent, 95 percent, 96 percent, 97 percent, 98 percent, or 99 percent sequence identity) to the amino acid sequence set forth in SEQ ID NO:2.

The alignment shown in FIG. 1 sets forth amino acid sequences of SEQ ID NO:2 orthologues and a consensus sequence. A consensus amino acid sequence for such orthologues was determined by aligning amino acid sequences, e.g., amino acid sequences related to SEQ ID NO:2, from a variety of species and determining the most common amino acid or type of amino acid at each position. For example, the alignment in FIG. 1 provides the amino acid sequences of CeresClone 13832 (SEQ ID NO:2), gi30102906 (SEQ ID NO:3), CeresClone: 962327 (SEQ ID NO:4), CeresClone: 1101577 (SEQ ID NO:6), gi50934425 (SEQ ID NO:7), gi40850574 (SEQ ID NO:8), gi7488772 (SEQ ID NO:9), CeresClone: 701370 (SEQ ID NO:10), gi66271037 (SEQ ID NO:11), and gi5031281 (SEQ ID NO:12). In certain cases, therefore, a lysine-modulating polypeptide can include an amino acid sequence having about 80% or greater sequence identity to an amino acid sequence set forth in FIG. 1, e.g., 80% or greater amino acid sequence identity to CeresClone 13832 (SEQ ID NO:2), CeresClone: 962327 (SEQ ID NO:4), CeresClone: 1101577 (SEQ ID NO:6), and CeresClone: 701370 (SEQ ID NO:10). Eighty percent sequence identity or greater can be about 82, 85, 87, 90, 92, 95, 96, 97, 98, 99, or 100% sequence identity to such a sequence.

2. Leucine-Modulating Polypeptides

Figure 2:
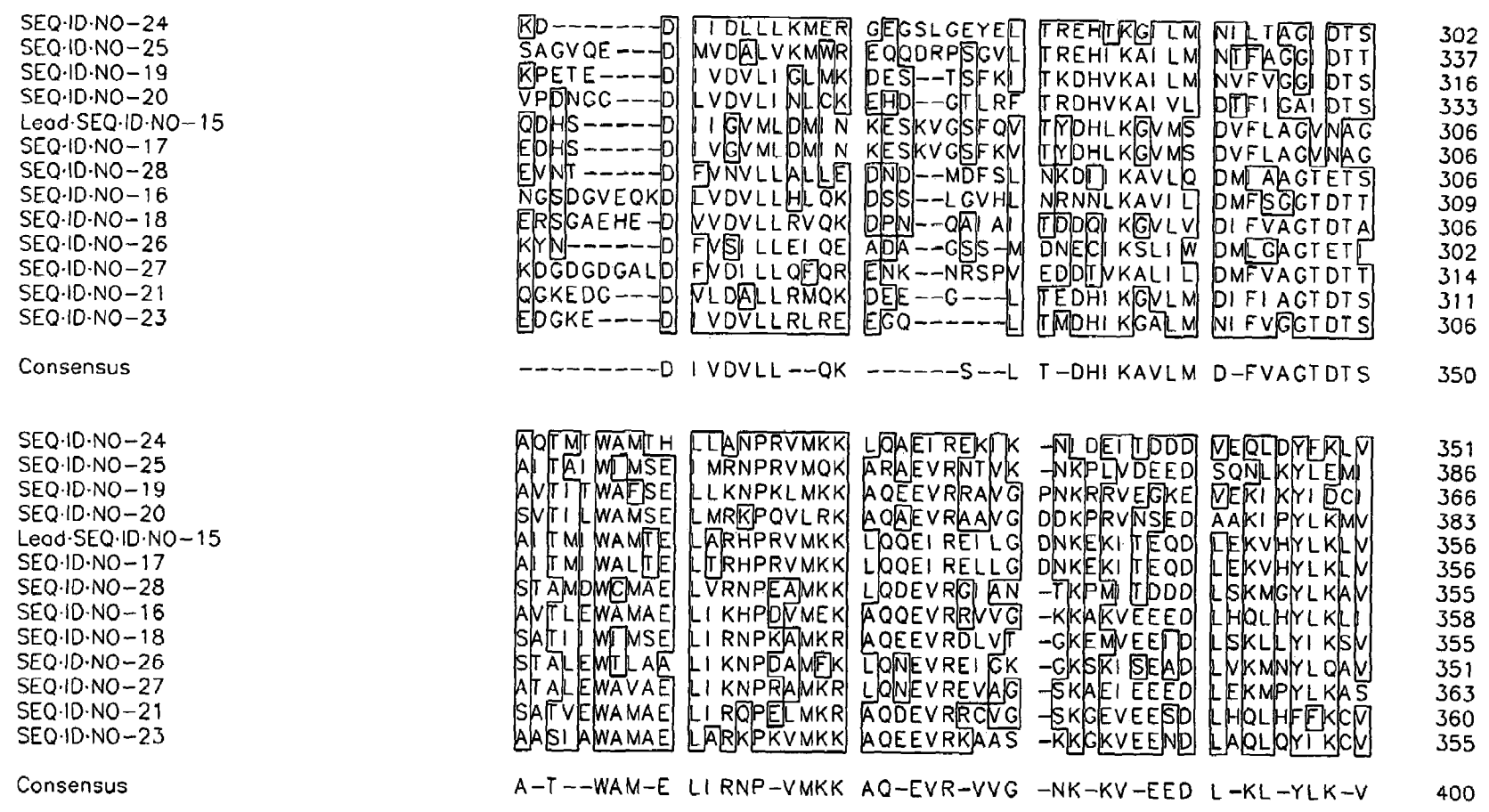

A leucine modulating polypeptide can have the amino acid sequence of cDNA ID 23530177 as set forth in FIG. 2 and SEQ ID NO:15. cDNA ID 23530177 is predicted to be a cytochrome P450 protein from the CYP71B subfamily. Cytochrome P450 enzymes comprise a diverse superfamily of proteins that mediate oxidative transformations in a wide array of biosynthetic and detoxification pathways essential for plant growth and development. All P450 enzymes have a common catalytic center consisting of a heme molecule with iron coordinated to the thiolate of a conserved cysteine, as well as a common overall topology and tridimensional fold.

Thus, a leucine-modulating polypeptide can be an *Arabidopsis* polypeptide having the amino acid sequence set forth in SEQ ID NO:15. Alternatively, a leucine-modulating polypeptide can be an ortholog, homolog, or variant of the polypeptide having the sequence set forth in SEQ ID NO:15. A leucine-modulating polypeptide, as described herein, can have an amino acid sequence with at least 35 percent sequence identity (e.g., percent, percent, 45 percent, 50 percent, 55 percent, 60 percent, 65 percent, 70 percent, 80 percent, 81 percent, 82 percent, 83 percent, 84 percent, 85 percent, 86 percent, 87 percent, 88 percent, 89 percent, 90 percent, 91 percent, 92 percent, 93 percent, 94 percent, 95 percent, 96 percent, 97 percent, 98 percent, or 99 percent sequence identity) to the amino acid sequence set forth in SEQ ID NO:15.

FIG. 2 sets forth amino acid sequences of SEQ ID NO:15, orthologues and a consensus sequence. A consensus amino acid sequence for such orthologues was determined by aligning amino acid sequences, e.g., amino acid sequences related to SEQ ID NO:15, from a variety of species and determining the most common amino acid or type of amino acid at each position. For example, the alignment provides the amino acid sequences of cDNA ID 23530177 (SEQ ID NO:15), gi25282608 (SEQ ID NO:16), gi11994438 (SEQ ID NO:17), gi3334659 (SEQ ID NO:18), gi37788136 (SEQ ID NO:19), gi5915841 (SEQ ID NO:20), gi17644125 (SEQ ID NO:21), gi13516750 (SEQ ID NO:23), gi1345641 (SEQ ID NO:24), gi50936051 (SEQ ID NO:25), gi46947673 (SEQ ID NO:26), gi3582021 (SEQ ID NO:27), and gi46409049 (SEQ ID NO:28). In certain cases, therefore, a leucine-modulating polypeptide can include an amino acid sequence having about 80% or greater sequence identity to an amino acid sequence set forth in FIG. 2, e.g. 80% or greater amino acid sequence identity to cDNA ID 23530177. Eighty percent sequence identity or greater can be about 82, 85, 87, 90, 92, 95, 96, 97, 98, 99, or 100% sequence identity to such a sequence.

The term "polypeptide" as used herein refers to a compound of two or more subunit amino acids, amino acid analogs, or other peptidomimetics, regardless of post-translational modification (e.g., phosphorylation or glycosylation). The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

By "isolated" or "purified" with respect to a polypeptide, it is meant that the polypeptide is separated to some extent from the cellular components with which it is normally found in nature (e.g., other polypeptides, lipids, carbohydrates, and nucleic acids). A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

Other amino acid-modulating polypeptides can be identified by functional complementation of amino acid-modulating polypeptide mutants. Suitable amino acid-modulating polypeptides also can be identified by analysis of nucleotide and polypeptide sequence alignments. For example, performing a query on a database of nucleotide or polypeptide sequences can identify other orthologs of the polypeptides having the amino acid sequences set forth in SEQ ID NO:2, and SEQ ID NO:15 Sequence analysis can involve BLAST or PSI-BLAST analysis of nonredundant databases using amino acid sequences of known amino acid-modulating polypeptides. If desired, manual inspection can be performed by selecting those candidates that appear to have domains suspected of being present in amino acid-modulating polypeptides.

Typically, conserved regions of amino acid-modulating polypeptides exhibit at least 40% amino acid sequence identity (e.g., at least 45%, at least 50%, at least 60%, at least 70%, at least 80%, or at least 90% amino acid sequence identity). Conserved regions of target and template polypeptides can exhibit at least 92%, 94%, 96%, 98%, or 99% amino acid sequence identity. Amino acid sequence identity can be deduced from amino acid or nucleotide sequences. In certain cases, highly conserved domains can be identified within amino acid-modulating polypeptides. These conserved regions can be useful in identifying functionally similar polypeptides.

Domains are groups of contiguous amino acids in a polypeptide that can be used to characterize protein families and/or parts of proteins. Such domains have a "fingerprint" or "signature" that can comprise conserved (1) primary sequence, (2) secondary structure, and/or (3) three-dimensional conformation. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed.

The identification of conserved regions in a template, or subject, polypeptide can facilitate production of variants of wild type amino acid-modulating polypeptides. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Pfam/ and online at genome.wustl.edu/Pfam/. Descriptions of the information included at the Pfam database are included in Sonnhammer et al., 1998, Nucl. Acids Res. 26: 320-322; Sonnhammer et al., 1997, Proteins 28:405-420; and Bateman et al., 1999, Nucl. Acids Res. 27:260-262. From the Pfam database, consensus sequences of protein motifs and domains can be aligned with the template polypeptide sequence to determine conserved region(s).

Conserved regions also can be determined by aligning sequences of the same or related polypeptides from closely related species. Closely related species preferably are from the same family. In some embodiments, alignment of sequences from two different species is adequate. For example, sequences from *Arabidopsis* and *Zea mays* can be used to identify one or more conserved regions.

B. Polynucleotides

Also provided herein are polynucleotides that encode any of the amino acid-modulating polypeptides described previously, e.g., any of the amino acid sequences set forth in the alignments shown in FIG. 1 or 2. In some cases an isolated polynucleotide can encode a polypeptide having 80% or more sequence identity to a lysine-modulating polypeptide as set forth in FIG. 1. For example, a polynucleotide sequence encoding a lysine modulating polypeptide can have 80% or more sequence identity to SEQ ID NO:1. In other cases an isolated polynucleotide can encode a polypeptide having 80% or more sequence identity to a leucine-modulating polypeptide as set forth in FIG. 2. For example, a polynucleotide sequence encoding a lysine modulating polypeptide can have 80% or more sequence identity to SEQ ID NO:14.

The terms "nucleic acid" or "polynucleotide" are used interchangeably herein, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

As used herein, "isolated," when in reference to a nucleic acid, refers to a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus, or the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made by, for example, chemical synthesis or the polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. Examples of means by which this can be accomplished in plants are well known in the art, such as *Agrobacterium*-mediated transformation (for dicots, see Salomon et al. EMBO J. 3:141 (1984); Herrera-Estrella et al. EMBO J. 2:987 (1983); for monocots, see Escudero et al., Plant J. 10:355 (1996), Ishida et al., Nature Biotechnology 14:745 (1996), May et al., Bio/Technology 13:486 (1995)); biolistic methods (Armaleo et al., Current Genetics 17:97 1990)); electroporation; in planta techniques, and the like. Such a plant containing an exogenous nucleic acid is referred to here as a T1 plant for the primary transgenic plant, a T2 plant for the first generation, and T3, T4, etc. for second and subsequent generation plants. T2 progeny are the result of self-fertilization of a T1 plant. T3 progeny are the result of self-fertilization of a T2 plant.

An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell (or plant) under consideration. For example, a transgenic plant containing an exogenous nucleic acid can be the progeny of a cross between a stably transformed plant and a non-transgenic plant. Such progeny are considered to contain the exogenous nucleic acid.

As used herein, the term "percent sequence identity" refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw). To determine a "percent identity" between a query sequence and a subject sequence, the number of matching bases or amino acids in the alignment is divided by the total number of matched and mismatched bases or amino acids, followed by multiplying the result by 100.

To determine a percent identity between a query sequence and a subject sequence, the number of matching bases or amino acids in the alignment is divided by the total number of matched and mismatched bases or amino acids excluding gaps, followed by multiplying the result by 100. The output is the percent identity of the subject sequence with respect to the query sequence.

To determine a percent identity between a query sequence and a subject sequence, the number of matching bases or amino acids is divided by the total number of bases or amino acids, and multiplied by 100. For example, if a query nucleotide sequence and a subject nucleotide sequence each are 500 base pairs long and have 200 matched (or identical) bases, these nucleotide sequences are 40 percent identical. If the two compared sequences are of different lengths, the number of matches is divided by the shorter of the two sequence lengths. For example, if 100 amino acids are matched between a 400 amino acid query polypeptide and a 500 amino acid subject polypeptide, these polypeptides would be 25 percent identical with respect to the query polypeptide.

It is noted that a query nucleotide or amino acid sequence that aligns with a subject sequence can result in many different lengths, with each length having its own percent identity. In addition, it is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that methods described herein can utilize non-transgenic plant cells or plants that carry a mutation in an amino acid-modulating polypeptide. For example, a plant carrying a T-DNA insertion, a deletion, a transversion mutation, or a transition mutation in the coding sequence for one of the aforementioned polypeptides can affect amino acid levels.

II. Recombinant Constructs and Vectors

Recombinant constructs are also provided herein and can be used to transform plants or plant cells in order to modulate the level of one or more amino acids, e.g., lysine or leucine, and/or sugars, e.g. glucose, fructose and galactose. A recombinant nucleic acid construct comprises a nucleic acid encoding one or more amino acid-modulating polypeptides as described herein, operably linked to a regulatory region suitable for expressing the regulatory protein in the plant or cell. Thus, a nucleic acid can comprise a coding sequence that includes any of the lysine-modulating polypeptides as set forth in FIG. 1. A nucleic acid can comprise a coding sequence that includes any of the leucine-modulating polypeptides as set forth in FIG. 2.

A. Vectors

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, tobacco mosaic virus and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

B. Regulatory Regions

The term "regulatory region" refers to nucleotide sequences that influence transcription or translation initiation and rate, and stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences, such as secretory signals and protease cleavage sites.

As used herein, the term "operably linked" refers to positioning of a regulatory region and a transcribable sequence in a nucleic acid so as to allow or facilitate transcription of the transcribable sequence. For example, a regulatory region is operably linked to a coding sequence when RNA polymerase is able to transcribe the coding sequence into mRNA, which then can be translated into a protein encoded by the coding sequence.

Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically comprises at least a core (basal) promoter. A promoter also may include at least one control element such as an upstream element. Such elements include upstream activation regions (UARs) and, optionally, other DNA sequences that affect transcription of a polynucleotide such as a synthetic upstream element. The choice of promoters to be included depends upon several factors, including, but not limited to, efficiency, selectability, inducibility, desired expression level, and cell or tissue specificity.

1. Constitutive Promoters

Constitutive promoters can promote transcription of an operably linked nucleic acid under most, but not necessarily all, environmental conditions and states of development or cell differentiation. Non-limiting examples of constitutive promoters that can be included in the nucleic acid constructs provided herein include the cauliflower mosaic virus (CaMV) 35S transcription initiation region, the mannopine synthase (MAS) promoter, the 1' or 2' promoters derived from T-DNA of *Agrobacterium tumefaciens*, the figwort mosaic virus 35S promoter, actin promoters such as the rice actin promoter, promoter 32449, promoter 13879, and ubiquitin promoters such as the maize ubiquitin-1 promoter.

2. Broadly Expressing Promoters

A promoter can be said to be "broadly expressing" when it promotes transcription in many, but not all, plant tissues. For example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. In certain cases, a broadly expressing promoter operably linked to a sequence can promote transcription of the linked sequence in a plant shoot at a level that is at least two times, e.g., at least 3, 5, 10, or 20 times, greater than the level of transcription in a developing seed. In other cases, a broadly expressing promoter can promote transcription in a plant shoot at a level that is at least two times, e.g., at least 3, 5, 10, or 20 times, greater than the level of transcription in a reproductive tissue of a flower. In view of the above, the CaMV 35S promoter is not considered a broadly expressing promoter. Non-limiting examples of broadly expressing promoters that can be included in the nucleic acid constructs provided herein include the p326, YP0158, YP0214, YP0380, PT0848, PTO633, YP0050, YP0144 and YP0190 promoters. See, e.g., U.S. patent application Ser. No. 11/208,308, filed Aug. 19, 2005.

Tissue-, organ- and cell-specific promoters confer transcription only or predominantly in a particular tissue, organ, and cell type, respectively. In some embodiments, promoters specific to non-seed tissues, such as vegetative tissues can be used. Vegetative tissues include the stem, parenchyma, ground meristem, vascular bundle, cambium, phloem, cortex, shoot apical meristem, lateral shoot meristem, root apical meristem, lateral root meristem, leaf primordium, leaf mesophyll, or leaf epidermis can be suitable regulatory regions.

3. Root-Specific Promoters

Root-specific promoters confer transcription only or predominantly in root tissue. Examples of root-specific promoters include the root specific subdomains of the CaMV 35S promoter (Lam et al., Proc Natl Acad Sci USA 86:7890-7894 (1989)), root cell specific promoters reported by Conkling et al. Plant Physiol. 93:1203-1211 (1990), and the tobacco RD2 gene promoter.

4. Seed-Specific Promoters

In some embodiments, promoters that are essentially specific to seeds can be useful. Transcription from a seed-specific promoter occurs primarily in endosperm and cotyledon tissue during seed development. Non-limiting examples of seed-specific promoters that can be included in the nucleic acid constructs provided herein include the napin promoter, the Arcelin-5 promoter, the phaseolin gene promoter (Bustos et al., Plant Cell 1(9):839-853 (1989)), the soybean trypsin inhibitor promoter (Riggs et al., Plant Cell 1(6):609-621 (1989)), the ACP promoter (Baerson et al., Plant Mol Biol, 22(2):255-267 (1993)), the stearoyl-ACP desaturase gene (Slocombe et al., Plant Physiol 104(4):167-176 (1994)), the soybean $\alpha'$ subunit of $\beta$-conglycinin promoter (Chen et al., Proc Natl Acad Sci USA 83:8560-8564 (1986)), the oleosin promoter (Hong et al., Plant Mol Biol 34(3):549-555 (1997)), zein promoters such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., Mol. Cell Biol. 13:5829-5842 (1993)), the beta-amylase gene promoter, and the barley hordein gene promoter.

5. Non-Seed Fruit Tissue Promoters

Promoters that are active in non-seed fruit tissues can also be useful, e.g., a polygalacturonidase promoter, the banana TRX promoter, and the melon actin promoter.

6. Photosynthetically-Active Tissue Promoters

Photosynthetically-active tissue promoters confer transcription only or predominantly in photosynthetically active tissue. Examples of such promoters include the ribulose-1,5-bisphosphate carboxylase (RbcS) promoters such as the RbcS promoter from eastern larch (Larix laricina), the pine cab6 promoter (Yamamoto et al., Plant Cell Physiol. 35:773-778 (1994)), the Cab-1 gene promoter from wheat (Fejes et al., Plant Mol. Biol. 15:921-932 (1990)), the CAB-1 promoter from spinach (Lubberstedt et al., Plant Physiol. 104:997-1006 (1994)), the cab1R promoter from rice (Luan et al., Plant Cell 4:971-981 (1992)), the pyruvate, orthophosphate dikinase (PPDK) promoter from corn (Matsuoka et al., Proc Natl Aca. Sci USA 90:9586-9590 (1993)), the tobacco Lhcb1*2 promoter (Cerdan et al., Plant Mol. Biol. 33:245-255 (1997)), the *Arabidopsis thaliana* SUC2 sucrose-H+ symporter promoter (Truernit et al., Planta. 196:564-570 (1995)), and thylakoid membrane protein promoters from spinach (psaD, psaF, psaE, PC, FNR, atpC, atpD, cab, rbcS).

7. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

8. Other Promoters

Other classes of promoters include, but are not limited to, inducible promoters, such as promoters that confer transcription in response to external stimuli such as chemical agents, developmental stimuli, or environmental stimuli.

Other suitable promoters that may fall within one or more of the classes specified above include those set forth in U.S. Patent Application Ser. Nos. 60/505,689; 60/518,075; 60/544,771; 60/558,869; 60/583,691; 60/619,181; 60/637, 140; Ser. Nos. 10/957,569; 11/058,689; 11/172,703 and PCT/US05/23639, e.g., promoters designated YP0086 (gDNA ID 7418340), YP0188 (gDNA ID 7418570), YP0263 (gDNA ID 7418658), p13879, p32449, PT0758; PT0743; PT0829; YP0096 and YP0119.

9. Other Regulatory Regions

A 5' untranslated region (UTR) is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA message stability or translation attenuation. Examples of 3' UTRs include, but are not limited to polyadenylation signals and transcription termination sequences.

A polyadenylation region at the 3'-end of a coding region can also be operably linked to a coding sequence. The polyadenylation region can be derived from the natural gene, from various other plant genes, or from transfer-DNA (T-DNA).

A suitable enhancer is a cis-regulatory element (−212 to −154) from the upstream region of the octopine synthase (ocs) gene. Fromm et al., The Plant Cell 1:977-984 (1989).

The vectors provided herein also can include, for example, origins of replication, scaffold attachment regions (SARs), and/or markers. A marker gene can confer a selectable phenotype on a plant cell. For example, a marker can confer, biocide resistance, such as resistance to an antibiotic (e.g., kanamycin, G418, bleomycin, or hygromycin), or an herbicide (e.g., chlorsulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

It will be understood that more than one regulatory region may be present in a recombinant polynucleotide, e.g., introns, enhancers, upstream activation regions, and inducible elements. Thus, more than one regulatory region can be operably linked to the sequence encoding an amino acid-modulating polypeptide.

III. Transgenic Plants and Host Cells

A. Producing Transgenic Plants

The isolated nucleic acids, polynucleotides, and vectors provided herein can be used to transform plant cells and, if desired, generate transgenic plants. Thus, transgenic plants and plant cells containing the nucleic acids described herein also are provided, as are methods for making such transgenic plants and plant cells. A plant or plant cell can be transformed by having the construct integrated into its genome, i.e., can be stably transformed. Stably transformed cells typically retain the introduced nucleic acid sequence with each cell division. Alternatively, the plant or plant cells also can be transiently transformed such that the construct is not integrated into its genome. Transiently transformed cells typically lose some or all of the introduced nucleic acid construct with each cell division, such that the introduced nucleic acid cannot be detected in daughter cells after sufficient number of cell divisions. Both transiently transformed and stably transformed transgenic plants and plant cells can be useful in the methods described herein.

Typically, transgenic plant cells used in the methods described herein constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species or for further selection of other desirable traits. Alternatively, transgenic plants can be propagated vegetatively for those species amenable to such techniques. Progeny includes descendants of a particular plant or plant line. Progeny of an instant plant include seeds formed on F1, F2, F3, F4, F5, F6 and subsequent generation plants, or seeds formed on BC1, BC2, BC3, and subsequent generation plants, or seeds formed on F1BC1, F1BC2, F1BC3, and subsequent generation plants. Seeds produced by a transgenic plant can be grown and then selfed (or outcrossed and selfed) to obtain seeds homozygous for the nucleic acid construct.

Alternatively, transgenic plant cells can be grown in suspension culture, or tissue or organ culture, for production of secondary metabolites. For the purposes of the methods provided herein, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

Techniques for transforming a wide variety of higher plant species are known in the art. The polynucleotides and/or recombinant vectors described herein can be introduced into the genome of a plant host using any of a number of known methods, including electroporation, microinjection, and biolistic methods. Alternatively, polynucleotides or vectors can be combined with suitable T-DNA flanking regions and introduced into a conventional *Agrobacterium tumefaciens* host vector. Such *Agrobacterium tumefaciens*-mediated transformation techniques, including disarming and use of binary vectors, are well known in the art. Other gene transfer and transformation techniques include protoplast transformation through calcium or PEG, electroporation-mediated uptake of naked DNA, electroporation of plant tissues, viral vector-mediated transformation, and microprojectile bombardment (see, e.g., U.S. Pat. Nos. 5,538,880, 5,204,253, 5,591,616, and 6,329,571). If a cell or tissue culture is used as the recipient tissue for transformation, plants can be regenerated from transformed cultures using techniques known to those skilled in the art.

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known. After a polynucleotide is stably incorporated into a transgenic plant, it can be introduced into other plants using, for example, standard breeding techniques.

B. Host Cells and Plants

The polynucleotides and vectors described herein can be used to transform a number of monocotyledonous and dicotyledonous plants and plant cell systems. Plants that express an amino acid-modulating polypeptide as described herein can be used to provide food or foodstuffs having an enhanced nutritional content. For example, the seeds, fruits, leaves, roots and shoots can be used to provide foods and foodstuffs having enhanced nutritional content. Such plants can be a source of flours, oils and animal feeds. In other cases the plants can be used as a source from which to extract one or more amino acids.

The polynucleotides and vectors described herein can be used to transform plants and plant systems that include dicots such as alfalfa, amaranth, apple, aspen, beans (including kidney beans, lima beans, dry beans, green beans), blackberry, blueberry, broccoli, cabbage, carnation, carrot, castor bean, celery, chick pea, chicory, chocolate, cherry, clover, coffee, cotton, cottonseed, crambe, eucalyptus, flax, grape, grapefruit, hazel nut, lemon, lentils, lettuce, linseed, lupin, mango, melon (e.g., watermelon, cantaloupe), mustard, orange, peanut, peach, pear, peas, pepper, petunia, plum, poinsettia, poplar, potato, rapeseed (high erucic acid and canola), rose, safflower, sesame, soybean, spinach, strawberry, sugarbeet, sunflower, tea, tobacco, tomato, and willow, as well as monocots such as banana, barley, bentgrass, bermuda grass, date palm, fescue, field corn, garlic, millet, oat, oil palm, onion, pineapple, popcorn, rice, rye, sorghum, sudangrass, sugarcane, sweet corn, switchgrass, turf grasses, and wheat. Gymnosperms such as fir, pine and spruce can also be suitable. Brown seaweeds, green seaweeds, red seaweeds, and microalgae also can be used. In certain embodiments, plants such as sweet corn, field corn, popcorn, banana, pineapple, canola, cotton, wheat, soybean, rice, corn, grape, coffee, cocoa, potato, tomato, lettuce, chicory, and mint are preferred.

Thus, the methods and compositions described herein can be used with dicotyledonous plants belonging, for example, to the orders Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Magniolales, Malvales, Myricales, Myrtales, Nymphaeales, Papeverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Trochodendrales, Theales, Umbellales, Urticales, and Violales. The methods and compositions described herein also can be utilized with monocotyledonous plants such as those belonging to the orders Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, Zingiberales, and with plants belonging to Gymnospermae, e.g., Pinales, Ginkgoales, Cycadales and Gnetales.

The methods and compositions can be used over a broad range of plant species, including species from the dicot genera *Apium, Alseodaphne, Anacardium, Arachis, Atropa, Beilschmiedia, Brassica, Capsicum, Carthamus, Chicorium, Citrus, Citrullus, Cocculus, Cocos, Coffea, Corylus, Croton, Cucumis, Cucurbita, Cuphea, Daucus, Dianthus, Duguetia, Euphoria, Ficus, Fragaria, Glaucium, Glycine, Gossypium, Helianthus, Hevea, Hyoscyamus, Lactuca, Landolphia, Linum, Litsea, Lycopersicon, Lupinus, Majorana, Malus, Manihot, Medicago, Nicotiana, Olea, Papaver, Parthenium, Persea, Petunia, Phaseolus, Pistacia, Pisum, Populus* sect., *Prunus, Pyrus, Raphanus, Ricinus, Rosa, Rubus, Salix, Senecio, Sinapis, Solanum, Spinacia, Stephania, Tagetes, Theobroma, Trifolium, Trigonella, Vaccinium, Vicia, Vigna, Vinca, Vitis*, and the monocot genera *Allium, Andropogon, Aragrostis, Asparagus, Avena, Cynodon, Elaeis, Festuca, Festulolium, Heterocallis, Hordeum, Lemna, Lolium, Musa, Oryza, Panicum, Pannesetum, Phleum, Poa, Phoenix, Saccharum, Secale, Sorghum, Triticum*, and *Zea*; and the gymnosperm genera *Abies, Cunninghamia, Picea, Pinus*, and *Pseudotsuga*.

The methods and compositions described herein also can be used with brown seaweeds, e.g., *Ascophyllum nodosum, Fucus vesiculosus, Fucus serratus, Himanthalia elongata*, and *Undaria pinnatifida*; red seaweeds, e.g., *Porphyra umbilicalis, Palmaria palmata, Cracilaria verrucosa*, and *Chondrus crispus*; green seaweeds, e.g., *Ulva* spp. and *Enteromorpha* spp.; and microalgae, e.g., *Spirulina* sp. (*S. platensis* and *S. maxima*) and *Odontella aurita*. In addition, the methods and compositions can be used with *Cryptheco-dinium cohnii, Schizochytrium* spp., and *Haematococcus pluvialis*.

In some embodiments, a plant can be from a species selected from *Ananus comosus, Arabidopsis thaliana, Brassica rapa, Brassica napus, Brassica oleracea, Bixa orellana, Calendula officinalis, Cinnamommum camphora, Coffea arabica, Glycine max, Glycyrrhiza glabra, Gossypium hirsutum, Gossypium herbaceum, Lactuca sativa, Lycopersicon esculentum, Mentha piperita, Mentha spicata, Musa paradisiaca, Oryza Sativa, Parthenium argentatum, Rosmarinus officinalis, Solanum tuberosum, Theobroma cacao, Triticum aestivum, Vitis vinifera*, and *Zea mays*. For example, in certain embodiments, plants from the following species can be preferred: *Ananus comosus, Brassica rapa, Brassica napus, Brassica oleracea, Coffea arabica, Glycine max, Gossypium hirsutum, Gossypium herbaceum, Lactuca sativa, Lycopersicon esculentum, Mentha piperita, Mentha spicata, Musa paradisiaca, Oryza Sativa, Parthenium argentatum, Solanum tuberosum, Theobroma cacao, Triticum aestivum, Vitis vinifera*, and *Zea mays*.

In some cases, it may be desirable to produce nucleic acids and/or polypeptides described herein by recombinant production in a prokaryotic or non-plant eukaryotic host cell. To recombinantly produce polypeptides, a nucleic acid encoding the polypeptide of interest can be ligated into an expression vector and used to transform a bacterial, eukaryotic, or plant host cell (e.g., insect, yeast, mammalian, or plant cells). In bacterial systems, a strain of *Escherichia coli* such as BL-21 can be used. Suitable *E. coli* vectors include the pGEX series of vectors that produce fusion proteins with glutathione S-transferase (GST). Depending on the vector used, transformed *E. coli* are typically grown exponentially, then stimulated with isopropylthiogalactopyranoside (IPTG) prior to harvesting. In general, expressed fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Alternatively, 6×His-tags can be used to facilitate isolation.

In eukaryotic animal host cells, a number of viral-based expression systems are often utilized to express polypeptides. A nucleic acid encoding a polypeptide can be cloned into, for example, a baculoviral vector such as pBlueBac (Invitrogen, Carlsbad, Calif.) and then used to co-transfect insect cells such as *Spodoptera frugiperda* (Sf9) cells with wild type DNA from *Autographa californica* multiply enveloped nuclear polyhedrosis virus (AcMNPV). Recombinant viruses producing polypeptides of the invention can be identified by standard methodology. Mammalian cell lines that stably express polypeptides can be produced by using expression vectors with the appropriate control elements and a selectable marker. For example, the pcDNA3 eukaryotic expression vector (Invitrogen, Carlsbad, Calif.) is suitable for expression of polypeptides in cells such as Chinese hamster ovary (CHO) cells, COS-1 cells, human embryonic kidney 293 cells, NIH3T3 cells, BHK21 cells, MDCK cells, ST cells, PK15 cells, or human vascular endothelial cells (HUVEC). In some instances, the pcDNA3 vector can be used to express a polypeptide in BHK21 cells, where the vector includes a CMV promoter and a G418 antibiotic resistance gene. Following introduction of the expression vector, stable cell lines can be selected, e.g., by antibiotic resistance to G418, kanamycin, or hygromycin. Alternatively, amplified sequences can be ligated into a mammalian expression vector such as pcDNA3 (Invitrogen, San Diego, Calif.) and then transcribed and translated in vitro using wheat germ extract or rabbit reticulocyte lysate.

C. Plants with Modulated Amino Acid and/or Sugar Levels.

Transgenic plants (or plant cells) can have an altered amino acid and/or sugar levels as compared to those in a corresponding control plant (or plant cell) that either lacks the transgene or does not express the transgene. An amino acid-modulating polypeptide can affect the amino acid and/or sugar level of a plant (e.g., a transgenic plant) when expressed in the plant, e.g., at the appropriate time(s), in the appropriate tissue(s), or at the appropriate expression levels. Amino acid and sugar levels can be evaluated relative to a control plant that does not express the exogenous polynucleotide of interest, such as a corresponding wild type plant, a corresponding plant that is not transgenic for the exogenous polynucleotide of interest but otherwise is of the same genetic background as the transgenic plant of interest, or a corresponding plant of the same genetic background in which expression of the polypeptide is suppressed, inhibited, or not induced (e.g., where expression is under the control of an inducible promoter). A plant can be said "not to express" a polypeptide when the plant exhibits less than 10% (e.g., less than 9%, 8%, 7%, 6%, 5%, 4%, 3%, 2%, 1%, 0.5%, 0.1%, 0.01%, or 0.001%) of the amount of polypeptide or mRNA encoding the polypeptide exhibited by the plant of interest. Expression can be evaluated using methods including, for example, RT-PCR, Northern blots, S1 RNAse protection, primer extensions, Western blots, protein gel electrophoresis, immunoprecipitation, enzyme-linked immunoassays, chip assays, and mass spectrometry. It should be noted that if a polypeptide is expressed under the control of a tissue-specific or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

As described previously, the polynucleotides, recombinant vectors, host cells, and transgenic plants described herein can be engineered to yield overexpression of a polypeptide of interest. Overexpression of the polypeptides provided herein can be used to alter amino acid and/or sugar levels in a transgenic plant relative to a control plant not expressing the polypeptides. Overexpression of a lysine-modulating polypeptide, for example, can increase levels of lysine and sugars including glucose, fructose and galactose. In contrast, overexpression of a leucine-modulating polypeptide for example, can decrease levels of leucine.

In some embodiments, a plant in which expression of a lysine-modulating polypeptide is modulated can have increased levels of lysine. For example, a lysine-modulating polypeptide described herein can be expressed in a transgenic plant, resulting in increased levels of lysine. The lysine level can be increased by at least 5 percent (e.g., 5, 10, 15, 20, 25, 30, 35, 40, 45, 50, 55, 60, 65, 70, 75, 80, 85, 90, 95, 100, 150, 200, 250, 300, 350, 400, or more than 400 percent) as compared to the lysine level in a corresponding control plant that does not express the transgene. In some embodiments, a plant in which expression of a lysine-modulating polypeptide is modulated can have increased levels of seed lysine. The seed lysine level can be increased by at least 5 percent (e.g., 5, 10, 15, 20, 25, 30, 35, 40, 45, 50, 55, 60, 65, 70, 75, 80, 85, 90, 95, 98, 99, or 100 percent) as compared to the seed lysine level in a corresponding control plant that does not express the transgene. A plant in which expression of a lysine-modulating polypeptide is modulated can also have increased levels of one or more sugars, for example, glucose, sucrose and galactose. A sugar level can be increased by at least 5 percent (e.g., 5, 10, 15, 20, 25, 30, 35, 40, 45, 50, 55, 60, 65, 70, 75, 80, 85, 90, 95, 100, 150, 200, 250, 300, 350, 400, 500, 600, 700 or more than 700 percent) as compared to the sugar level in a corresponding control plant that does not express the transgene.

Alternatively, the polynucleotides and recombinant vectors described herein can be used to suppress or inhibit expression of a leucine modulating-polypeptide in a plant species of interest. For example, inhibition or suppression of transcription or translation of a leucine-modulating polypeptide may yield plants having increased leucine levels relative to control plants.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a leucine-modulating polypeptide, e.g., the leucine-modulating polypeptide orthologs set forth in FIG. 2. A nucleic acid that decreases the level of a transcription or translation product of a gene encoding a leucine-modulating polypeptide is transcribed into an antisense nucleic acid similar or identical to the sense coding sequence of an orthologue, homologue or variant, e.g. SEQ ID NO:15. Alternatively, the transcription product of an isolated nucleic acid can be similar or identical to the sense coding sequence of a leucine-modulating polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, R. et al., Proc. Natl. Acad. Sci. USA, 92(13): 6175-6179 (1995); de Feyter, R. and Gaudron, J., Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in Tetrahymena thermophila, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the leucine-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller, 1997, Antisense Nucleic Acid Drug Dev., 7: 187-195; Hyrup et al., 1996, Bioorgan. Med. Chem., 4: 5-23. In addition, the deoxyphosphate backbone can be replaced with, for example, a phosphorothioate or phosphorodithioate backbone, a phosphoroamidite, or an alkyl phosphotriester backbone.

In some embodiments, a plant in which expression of a leucine-modulating polypeptide is modulated can have increased or decreased levels of leucine in one or more non-seed tissues. For example, a plant in which expression of a leucine-modulating polypeptide is modulated can have decreased levels of leucine in one or more non-seed tissues. The leucine level can be decreased by at least 5 percent (e.g., 5, 10, 15, 20, 25, 30, 35, 40, 45, 50, 55, 60, 65, 70, 75, 80, 85, 90, 95, 98, 99, or 100 percent) as compared to the leucine level in a corresponding control plant that does not express the transgene.

The decrease in the amount of leucine can be restricted in some embodiments to particular tissues and/or organs, relative to other tissues and/or organs. For example, a transgenic plant can have an decreased amount of leucine in fruit tissue relative to leaf or root tissue.

Typically, a difference (e.g., an increase or decrease) in the amount of an amino acid or sugar in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of an amino acid is statistically significant at $p<0.01$, $p<0.005$, or $p<0.001$. A statistically significant difference in, for example, the amount of an amino acid in a transgenic plant compared to the amount in cells of a control plant indicates that (1) the recombinant nucleic acid present in the transgenic plant results in altered amino acid levels and/or (2) the recombinant nucleic acid warrants further study as a candidate for altering the amount of amino acid in a plant. The amount of an amino acid or sugar in a transgenic plant or plant cell can be determined by known techniques, e.g., by extraction of amino acids and/or sugars followed by gas chromatography-mass spectrometry (GC-MS) or liquid chromatography-mass spectrometry (LC-MS). If desired, the structure of the amino acid or sugar can be confirmed by GC-MS, LC-MS, nuclear magnetic resonance and/or other known techniques.

IV. Methods of Producing Amino Acids and Sugars

Also provided are methods for producing amino acids and sugars. Such methods can include growing a plant cell that includes a nucleic acid encoding an amino acid-modulating protein as described herein, under conditions effective for the expression of the amino acid-modulating protein. Also provided herein are methods for modulating (e.g., altering, increasing, or decreasing) the amounts of one or more amino acids and sugars in a plant cell. The methods can include growing a plant cell as described above, i.e., a plant cell that includes a nucleic acid encoding an amino acid-modulating protein as described herein. The one or more amino acids or sugars produced by these methods can be novel amino acids or sugars, e.g., not normally produced in a wild-type plant cell.

The methods can further include the step of recovering one or more amino acids or sugars from the cells. For example, plant cells known or suspected of producing one or amino acids or sugars can be subjected to fractionation to recover a desired amino acid or sugar. Typically, fractionation is guided by in vitro assay of fractions. In some instances, cells containing one or more amino acids or sugars can be separated from cells not containing, or containing lower amounts of the amino acids or sugars, in order to enrich for cells or cell types that contain the desired amino acids or sugars. A number of methods for separating particular cell types or tissues are known to those having ordinary skill in the art.

V. Articles of Manufacture: Seeds, Plant Products, and Plant Tissues

Also provided herein are articles of manufacture that comprise seeds from transgenic plants provided herein. The seeds can be conditioned using means known in the art and packaged using packaging material well known in the art to prepare an article of manufacture. A package of seed can have a label e.g., a tag or label secured to the packaging material, a label printed on the packaging material or a label inserted within the package. The label can indicate that plants grown from the seeds contained within the package can produce a crop having an altered level of lysine and/or one or more sugars, for example, glucose, fructose and galactose, or an altered level of leucine relative to corresponding control plants.

Articles of manufacture can also include products derived from any of the transgenic plants described herein. For example, a flour, extract, or foodstuff can be derived from one or more tissues or organs of the transgenic plants described herein. Such products may have modulated levels of any one of the amino acids, e.g., lysine or leucine, or any sugar, e.g. glucose, fructose, or galactose. In some cases, the level of an amino acid or sugar may be increased relative to products derived from control plants. In some cases the level of an amino acid or sugar may be decreased relative to products derived from control plants.

The invention is further described in the following examples, which do not limit the scope of the invention described in the claims.

EXAMPLES

Example 1

Generation of Plants Containing a 35S::23530177 Construct

The following symbols are used in the Examples: T1: first generation transformant; T2: second generation, progeny of self-pollinated T1 plants; T3: third generation, progeny of self-pollinated T2 plants; T4: fourth generation, progeny of self-pollinated T3 plants.

cDNA ID 23530177 (SEQ ID NO: 14) is predicted to encode a cytochrome P450 protein from the CYP71B22 subfamily. T-DNA binary vector constructs were made using standard molecular biology techniques. A recombinant DNA construct for ectopic expression was made by operably linking a cDNA corresponding to cDNA ID 23530177 (SEQ ID NO: 14) in the sense orientation to a CaMV 35S promoter in a Ti plasmid vector. The Ti plasmid vector used for this construct, CRS 338, contains a plant selectable marker gene phosphinothricin acetyltransferase (PAT) which confers resistance to the herbicide Finale®. The resulting construct was designated CERES15218307. The construct was then introduced into *Arabidopsis* ecotype Wassilewskija (WS) by the floral dip method essentially as described in Bechtold, N. et al., C.R. Acad. Sci. Paris, 316:1194-1199 (1993). Ten independently transformed events were selected. Plants from these events were designated as ME04600 events. Control plants contained a construct having the Finale® marker gene but lacking the cDNA ID 23530177 (SEQ ID NO: 14) coding sequence. The physical appearance of the ten selected T1 plants was identical to that of the controls.

The T1 plants were allowed to self-pollinate. T2 seeds were collected and a portion were germinated, allowed to self-pollinate, and T3 seeds were collected. T2 and T3 seeds of the *Arabidopsis thaliana* ME04600 screening events were planted in soil comprising Sunshine LP5 Mix and Thermorock Vermiculite Medium #3 at a ratio of 60:40, respectively. The seeds were stratified at 4° C. for approximately two to three days. After stratification, the seeds were transferred to the greenhouse and covered with a plastic dome and tarp until most of the seeds had germinated. Plants were grown under long day conditions. Approximately seven to ten days post-germination, plants were sprayed with Finale® herbicide to confirm that the plants were transgenic for the Finale® marker.

Example 2

Analysis of Leucine Content in *Arabidopsis* ME04600 Lines

Tissues from ME04600 plants were analyzed for alterations in the levels of amino acids, fatty acids, sugar alcohols, sugars, sterols and other metabolites. Metabolic profiling by Gas Chromatography and Mass Spectrometry (GC-MS) was performed for ME04600 events in two screens: a primary screen for masterpools (T2 seed stocks containing a mixture of all ten events) and a confirmation screen for individual T2 and T3 events of ME04600 lines. In both screens, ME04600 lines were grown in the greenhouse. Aerial tissues were harvested at 10 days post-bolting from four randomly chosen Finale® resistant plants of each masterpool or individual event. The tissues were pooled and immediately frozen in liquid nitrogen. Frozen tissues were stored at −80° C., subsequently lyophilized for 72 hours, and were crushed into a fine powder.

For GC-MS analysis, the resulting fine powder was sequentially extracted using methanol and dichloromethane. The polar phases were derivatized using methoxyamine and N-Methyl-N-(trimethylsilyl)trifluoroacetamide (MSTFA). Only the aqueous phase was used in the analyses. Derivatized extracts were injected into a Shimadzu GC-MS QP-2010. Data were analyzed using Shimadzu GC-MS Solutions software. Target ion peak areas were integrated after identity confirmation using retention time standards and reference ion peak ratios. The target ion peak areas were normalized with respect to the internal standard and compared to the control sample. Ribitol was used as the polar phase internal standard (ISTD). Target peak areas were integrated and the values exported to Excel. All areas were normalized with respect to the internal standard and the initial weight of the sample. All experimental samples were normalized with respect to the control. The levels of thirty-two aerial tissue metabolites analyzed by GC-MS are shown in Table 1.

TABLE 1

| Compound | Compound Class | Compound | Compound Class |
|---|---|---|---|
| Ribitol (ISTD) | Sugar Alcohol (ISTD) | trans-Cinnamic Acid | Phenylpropanoid |
| L-Alanine | Amino Acid | L-Phenylalanine | Amino Acid |
| L-Valine | Amino Acid | L-Asparagine | Amino Acid |
| L-Glycine | Amino Acid | Fructose (peak 1) | Sugar |
| L-Leucine | Amino Acid | Galactose (peak 1) | Sugar |
| L-Isoleucine | Amino Acid | Glucose (peak 1) | Sugar |
| L-Serine | Amino Acid | L-Lysine | Amino Acid |
| L-Proline | Amino Acid | 3-Coumaric Acid | Phenylpropanoid |
| L-Threonine | Amino Acid | L-Histidine | Amino Acid |
| Homoserine | Amino Acid | Coniferyl Alcohol | Phenylpropanoid |
| L-Aspartic Acid | Amino Acid | Caffeic Acid | Phenylpropanoid |
| L-Methionine | Amino Acid | Ferrulic Acid | Phenylpropanoid |
| L-Cysteine | Amino Acid | L-Tryptophan diTMS | Amino Acid |
| Arabinose (peak 1) | Sugar | Sinapinic Acid | Phenylpropanoid |
| L-Glutamic Acid | Amino Acid | Sucrose | Sugar |
| L-Glutamine | Amino Acid | Raffinose | Sugar |

Tissue from the ME04600 masterpool showed a 75% decrease in leucine levels relative to those detected in the corresponding transgenic controls. A calibration curve prepared with a known concentrations of a leucine standard was used to confirm that all leucine measurements on plant tissues were within the linear range of detection by GC-MS. Analyses of four T2 plants in the confirmation screen showed that Events -01 and -04 had statistically significant decreases in leucine levels (38% and 27%, respectively) compared to the transgenic controls. Analyses of T3 plants from Events -01, -02, -03 and -04 showed that Events -01 and -04 also had statistically significant decreases in leucine levels (26% and 42%, respectively) when compared to the transgenic controls. Table 2 below summarizes the results for T2 and T3 individual plants.

TABLE 2

Leucine Levels (% Control) in ME04600 $T_2$ and $T_3$ Generations

|  | ME04600-01 | ME04600-02 | ME04600-03 | ME04600-04 | Control |
|---|---|---|---|---|---|
| $T_2$ | 62 ± 3 | 131 ± 12 | 92 ± 10 | 73 ± 9 | 100 ± 9 |
| p-value | <0.01 | 0.06 | 0.25 | <0.01 | NA |
| $T_3$ | 74 ± 7 | 93 ± 7 | 80 ± 10 | 58 ± 8 | 100 ± 9 |
| p-value | <0.01 | 0.20 | 0.01 | <0.01 | NA |

Isoleucine levels were also found to be decreased in plants ME04600-01 and ME04600-04. These decreases, however, were not significant to a p-value of less than 0.05 in two events over two generations. Of the other 30 compounds measured by this method, none showed significant changes in two events over two generations. Overall visual comparisons of the chromatograms did not indicate any other statistically significant changes in the metabolite profile.

T2 plants of plants ME04600-01 and ME04600-04 exhibited no statistically significant differences in germination rate, general morphology/architecture, days to flowering, rosette area 7 days post-bolting, or fertility (silique number and seed fill), when compared to the transgenic controls.

Example 3

Generation of Plants Containing a 35S::12323707 Construct cDNA 12323707 (SEQ ID NO:1) is predicted to encode a zinc finger transcription factor. *Arabidopsis* Wassilewskija (WS) plants were transformed with a Ti plasmid containing a nucleic acid designated cDNA ID 12323707 (SEQ ID NO:1) operably linked in the sense orientation relative to the CaMV 35S constitutive promoter according to the protocol in Example 1. Ten independently transformed events were selected. Plants from these events were designated as ME06384 events. The physical appearance of the ten selected T1 plants was identical to that of the controls. T1 plants were allowed to self-pollinate and T2 seeds were collected. A portion of the T2 seeds was germinated, allowed to self pollinate and T3 seeds were collected. T2 and T3 seeds of the ME06384 plants were planted and grown as described in Example 1 to confirm that the plants were transgenic for the Finale® marker.

Example 4

Analysis of Lysine Content in *Arabidopsis* ME06384 Events

Approximately ten days post-bolting, aerial tissues from Finale®-resistant T2 plants of each ME06384 event were analyzed for alterations in the levels of amino acids, fatty acids, sugar alcohols, sugars, sterols and other metabolites according to the protocol in Example 2. In addition, four T2 plants were allowed to self-pollinate, and mature seeds were collected and pooled. Aerial tissues from Finale®-resistant T3 plants were analyzed as in Example 2. Metabolites were extracted from pooled seeds and analysed using a commercially available kit, EZ:FAAST (Phenomenex, Torrence, Calif.).

For aerial tissues, analyses of four T2 plants indicated that plants -01, -03, -04, -05 had significant increases of 31%, 72%, 74% and 93%, respectively, in lysine levels as shown in Table 3. Significant increases in lysine levels were also observed for aerial tissues in the T3 generation, with plants 01, -03, -04, -05 having increases of 141%, 52%, 106% and 92%, respectively, in lysine levels. In T3 seeds, lysine content was also elevated relative to those from control plants in the T2 generation (data not shown).

TABLE 3

Lysine Increase (Fold Increase) in ME06384 $T_2$ and $T_3$ Generation

|  | ME06384-01 | ME06384-02 | ME06384-03 | ME06384-04 | ME06384-05 | Control |
|---|---|---|---|---|---|---|
| $T_2$ | 1.31 ± 0.22 | 1.02 ± 0.8 | 1.72 ± 0.13 | 1.75 ± 0.18 | 1.93 ± 0.22 | 1.00 ± 0.06 |
| p-value | 0.13 | <0.01 | <0.01 | <0.01 | <0.01 | N/A |
| $T_3$ | 2.41 ± 0.37 | 1.92 ± 0.64 | 1.52 ± 0.04 | 2.06 ± 0.08 | 1.92 ± 0.23 | 1 ± 0.25 |
| p-value | <0.01 | <0.01 | <0.01 | <0.01 | <0.01 | N/A |

TABLE 4

|  | ME06384-01 | ME06834-03 | ME06834-04 | ME06834-05 | Control |
|---|---|---|---|---|---|
| $T_3$ | 122.3 ± 22.5 | 157.4 ± 4.2 | 156.1 ± 50.1 | 154.6 ± 8.3 | 100 ± 15.5 |
| p-value | 0.07 | <0.01 | <0.01 | <0.01 | N/A |

Example 5

Analysis of Sugar Content in *Arabidopsis* ME06384 Events

Aerial tissues from ME06384 plants were analyzed for sugar content as described in Example 4. Aerial tissues from the T2 generation of ME06384 plants had significantly elevated levels of the sugars, glucose, fructose and galactose. The results of the sugar analyses are shown in Tables 5, 6, and 7. Glucose levels were increased by about 1.76, 2.42, 2.23, 1.53, and 1.93-fold in plants ME06384-01, 02, 03, 04, and 05, respectively, in aerial tissues from T2 plants. Fructose levels were increased by about 1.73, 3.87, 4.16, 2.37 and 2.25-fold in plants ME06384-01, 02, 03, 04, and 05, respectively, in aerial tissues from T2 plants. Galactose levels were increased by about 1.76, 2.42, 2.23, 1.53, and 1.93-fold in plants ME06384-01, 02, 03, 04, and 05, respectively, in aerial tissues from T2 plants. A slight increase, which was not statistically significant, was observed for glucose, fructose and galactose in the T3 generation.

TABLE 5

Glucose Increase (Fold Increase) in ME06384 $T_2$ and $T_3$ Generation

|  | ME06384-01 | ME06384-02 | ME06384-03 | ME06384-04 | ME06384-05 | Control |
|---|---|---|---|---|---|---|
| $T_2$ | 1.76 ± 0.14 | 2.42 ± 0.63 | 2.23 ± 0.08 | 1.53 ± 0.56 | 1.93 ± 0.12 | 1.00 ± 0.1 |
| p-value | <0.01 | 0.01 | <0.01 | 0.18 | <0.01 | N/A |
| $T_3$ | 1.12 ± 0.07 | 1.05 ± 0.03 | 1.03 ± 0.02 | 1.05 ± 0.03 | 1.04 ± 0.02 | 1 ± 0.1 |
| p-value | 0.05 | 0.22 | 0.4 | 0.23 | 0.31 | N/A |

TABLE 6

Fructose Increase (Fold Increase) in ME06384 $T_2$ and $T_3$ Generation

|  | ME06384-01 | ME06384-02 | ME06384-03 | ME06384-04 | ME06384-05 | Control |
|---|---|---|---|---|---|---|
| $T_2$ | 1.73 ± 0.28 | 3.87 ± 0.17 | 4.16 ± 0.46 | 2.37 ± 0.07 | 2.25 ± 0.15 | 1.00 ± 0.09 |
| p-value | 0.08 | <0.01 | <0.01 | <0.01 | <0.01 | N/A |
| $T_3$ | 1.07 ± 0.07 | 1.07 ± 0.04 | 1.08 ± 0.05 | 1.09 ± 0.05 | 1.02 ± 0.05 | 1 ± 0.13 |
| p-value | 0.26 | 0.23 | 0.22 | 0.18 | 0.5 | N/A |

TABLE 7

Galactose Increase (Fold Increase) in ME06384 $T_2$ and $T_3$ Generation

|  | ME06384-01 | ME06384-02 | ME06384-03 | ME06384-04 | ME06384-05 | Control |
|---|---|---|---|---|---|---|
| $T_2$ | 2.2 ± 0.23 | 3.76 ± 0.21 | 4.09 ± 0.49 | 2.71 ± 0.23 | 3.13 ± 0.09 | 1.00 ± 0.15 |
| p-value | <0.01 | <0.01 | <0.01 | <0.01 | <0.01 | N/A |
| $T_3$ | 1.11 ± 0.04 | 1.22 ± 0.03 | 1.16 ± 0.06 | 1.14 ± 0.09 | 1.05 ± 0.03 | 1 ± 0.22 |
| p-value | 0.26 | 0.07 | 0.16 | 0.18 | 0.47 | N/A |

Example 6

Determination of Ortholog/Functional Homolog Sequences

A subject sequence was considered a functional homolog and/or ortholog of a query sequence if the subject and query sequences encode proteins having a similar function and/or activity. A process known as Reciprocal BLAST (Rivera et al, *Proc. Natl Acad. Sci. USA*, 1998, 95:6239-6244) was used to identify potential functional homolog and/or ortholog sequences from databases consisting of all available public and proprietary peptide sequences, including NR from NCBI and peptide translations from Ceres clones.

Before starting a Reciprocal BLAST process, a specific query polypeptide was searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides were designated as a cluster.

The main Reciprocal BLAST process consists of two rounds of BLAST searches; forward search and reverse search. In the forward search step, a query polypeptide sequence, "polypeptide A," from source species $S^A$ was BLASTed against all protein sequences from a species of interest. Top hits were determined using an E-value cutoff of $10^{-5}$ and an identity cutoff of 35%. Among the top hits, the sequence having the lowest E-value was designated as the best hit, and considered a potential functional homolog and/or ortholog. Any other top hit that had a sequence identity of 80% or greater to the best hit or to the original query polypeptide was considered a potential functional homolog and/or ortholog as well. This process was repeated for all species of interest.

In the reverse search round, the top hits identified in the forward search from all species were BLASTed against all protein sequences from the source species $S^A$. A top hit from the forward search that returned a polypeptide from the aforementioned cluster as its best hit was also considered as a potential functional homolog and/or ortholog.

Functional homologs and/or orthologs were identified by manual inspection of potential functional homolog and/or ortholog sequences. Representative functional homologs and/or orthologs for SEQ ID NO: 2 are shown in FIG. 1 and percent identities are shown below in Table 8. Representative functional homologs and/or orthologs for SEQ ID NO: 15 are shown in FIG. 2 and percent identities are shown below in Table 9.

TABLE 8

Percent identity to CeresClone 13832 (SEQ ID NO: 2)

| Designation | Species | SEQ ID NO: | % Identity | e-value |
|---|---|---|---|---|
| gi\|30102906 | *Arabidopsis thaliana* | 3 | 98.86 | 4.90E−98 |
| CeresClone: 962327 | *Brassica napus* | 4 | 65.73 | 5.40E−60 |
| CeresClone: 1101577 | *Glycine max* | 6 | 43.98 | 3.10E−41 |
| gi\|50934425 | *Oryza sativa (japonica)* | 7 | 43.67 | 8.90E−35 |
| gi\|7488772 | *Phaseolus vulgaris* | 9 | 42.98 | 2.80E−24 |
| gi\|40850574 | *Musa acuminata* | 8 | 42.98 | 2.10E−26 |
| CeresClone: 701370 | *Triticum aestivum* | 10 | 41.24 | 6.30E−34 |
| gi\|66271037 | *Gossypium hirsutum* | 11 | 38.97 | 7.10E−26 |
| gi\|5031281 | *Prunus armeniaca* | 12 | 36.84 | 4.10E−30 |

TABLE 9

Percent identity to cDNA ID 23530177 (SEQ ID NO: 15)

| Designation | Species | SEQ ID NO: | % Identity | e-value |
|---|---|---|---|---|
| gi\|11994438 | *Arabidopsis thaliana* | 17 | 88.35 | 1.50E−248 |
| gi\|17644125 | *Musa acuminata* | 21 | 45.6 | 1.20E−115 |
| gi\|25282608 | *Persea americana* | 16 | 44.02 | 3.00E−117 |
| gi\|1345641 | *Thlaspi arvense* | 24 | 43.49 | 9.80E−119 |
| gi\|5915841 | *Sorghum bicolor* | 20 | 43.28 | 1.10E−119 |
| gi\|3334659 | *Glycine max* | 18 | 42.89 | 1.20E−111 |
| gi\|46947673 | *Ammi majus* | 26 | 41.92 | 6.90E−102 |
| gi\|13516750 | *Asparagus officinalis* | 23 | 41.72 | 1.10E−112 |
| gi\|3582021 | *Nepeta racemosa* | 27 | 41.57 | 2.40E−106 |
| gi\|50936051 | *Oryza sativa* | 25 | 39.88 | 6.70E−104 |
| gi\|46409049 | *Muscari armeniacum* | 28 | 39.8 | 3.00E−101 |
| gi\|37788136 | *Manihot esculenta* | 19 | 39.48 | 3.50E−107 |

A number of embodiments of the invention have been described. Nevertheless, it will be understood that various modifications may be made without departing from the spirit and scope of the invention. Accordingly, other embodiments are within the scope of the following claims.

What is claimed is:

1. A method of modulating the level of at least one of lysine, glucose, fructose and galactose in a plant, said method comprising:
   (a) introducing into a plurality of plant cells a nucleic acid comprising a nucleotide sequence encoding a polypeptide having 95% or greater sequence identity to the amino acid sequence of SEQ ID NO:2; and
   (b) producing a plurality of plants from said plant cells; and
   (c) selecting one or more plants from said plurality of plants that expresses said nucleic acid, wherein said selected plants are identified as having a difference in the level of at least one of lysine, glucose, fructose and galactose compared to the corresponding level in a corresponding control plant that does not comprise said nucleic acid.

2. The method of claim 1 wherein said polypeptide is SEQ ID NO:2.

3. The method of claim 1, wherein said polypeptide is SEQ ID NO:3.

4. The method of claim 1 wherein said sequence identity is 98% or greater.

5. The method of claim 1, 2, or 3, wherein said difference is an increase.

6. A method of producing a plant having a modulated level of at least one of lysine, glucose, fructose and galactose, said method comprising
   (a) introducing into a plurality of plant cells a nucleic acid comprising a nucleotide sequence encoding a polypeptide having 95% or greater sequence identity to the amino acid sequence of SEQ ID NO:2;
   (b) producing a plurality of plants from said plant cells;
   (c) selecting one or more plants from said plurality of plants that expresses said nucleic acid, wherein said selected plants are identified as having a difference in the level of at least one of lysine, glucose, fructose and galactose compared to the corresponding level in a corresponding control plant that does not comprise said nucleic acid; and
   (d) growing said plant.

7. The method of claim 6 wherein said polypeptide is SEQ ID NO:2.

8. The method of claim 6, wherein said polypeptide is SEQ ID NO:3.

9. The method of claim 6 wherein said sequence identity is 98% or greater.

10. The method of claim 6, 7, or 8, wherein said difference is an increase.

11. The method of claim 1, 6, 2, 3, 7, or 8, wherein said isolated nucleic acid is operably linked to a regulatory region.

12. The method of claim 11 wherein said regulatory region is a promoter.

13. The method of claim 12, wherein said promoter is a cell-specific or tissue-specific promoter.

14. The method of claim 12, wherein said promoter is a broadly expressing promoter and not a CaMV 35S promoter.

15. The method of claim 14, wherein said broadly expressing promoter is selected from the group consisting of the p326, YP0158, YP0214, YP0380, PT0848, PTO633, YP0050, YP0144 and YP0190 promoters.

16. The method of claim 12, wherein said tissue-specific promoter is a seed-specific promoter.

17. The method of claim 16, wherein said seed-specific promoter is selected from the group consisting of the napin promoter, the Arcelin-5 promoter, the phaseolin gene promoter, the soybean trypsin inhibitor promoter, the ACP promoter, the stearoyl-ACP desaturase gene promoter, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter.

18. The method of claim 12, wherein said promoter is a vegetative tissue specific promoter.

19. The method of claim 18, wherein said promoter is a fruit specific promoter.

20. The method of claim 12, wherein said promoter is an inducible promoter.

21. The method of claim 1, 6, 2, 3, 7, or 8 wherein said plant is from a genus selected from the group consisting of Abies, Agrostis, Allium, Alseodaphne, Anacardium, Andropogon, Arachis, Apium, Aragrostis, Ascophyllum, Asparagus, Atropa, Avena, Beilschmiedia, Brassica, Capsicum, Carthamus, Chondrus, Chicorium, Citrus, Citrullus, Cocculus, Cocos, Coffea, Corylus, Cracilaria, Croton, Crypthecodinium, Cucumis, Cucurbita, Cunninghamia, Cuphea, Cynodon, Daucus, Dianthus, Duguetia, Elaeis, Enteromorpha, Euphoria, Festuca, Festulolium, Ficus, Fragaria, Fucus, Glaucium, Glycine, Gossypium, Haematococcus, Helianthus, Heterocallis, Hevea, Himanthalia, Hordeum, Hyoscyamus, Lactuca, Landolphia, Lemna, Linum, Litsea, Lolium, Lycopersicon, Lupinus, Majorana, Malus, Manihot, Medicago, Musa, Nicotiana, Odontella, Olea, Oryza, Palmaria,

*Panicum, Pannesetum, Papaver, Parthenium, Persea, Petunia, Phaseolus, Phleum, Phoenix, Picea, Pinus, Pistacia, Pisum, Poa, Populus sect., Porphyra, Prunus, Pseudotsuga Pyrus, Raphanus, Ricinus, Rosa, Rubus, Saccharum, Salix, Schizochytrium, Secale, Senecio, Sinapis, Solanum, Sorghum, Spinacia, Spirulina, Stephania, Triticum, Tagetes, Theobroma, Trifolium, Trigonella, Ulva, Undaria, Vaccinium, Vicia, Vigna, Vinca, Vitis, Zea.*

22. The method of claim 1, 6, 2, 3, 7, or 8, wherein said plant is a species selected from *Ananus comosus, Arabidopsis thaliana, Brassica rapa, Brassica napus, Brassica oleracea, Bixa orellana, Calendula officinalis, Cinnamommum camphora, Coffea arabica, Glycine max, Glycyrrhiza glabra, Gossypium hirsutum, Gossypium herbaceum, Lactuca sativa, Lycopersicon esculentum, Mentha piperita, Mentha spicata, Musa paradisiaca, Oryza sativa, Parthenium argentatum, Rosmarinus officinalis, Solanum tuberosum, Theobroma cacao, Triticum aestivum, Vitis vinfera,* and *Zea mays.*

23. The method of claim 1, 6, 2, 3, 7, or 8, wherein said plant is selected from the group consisting of alfalfa, amaranth, apple, kidney beans, lima beans, dry beans, green beans, broccoli, cabbage, carrot, castor bean, chick peas, cherry, clover, coffee, cotton, cottonseed, crambe, eucalyptus, flax, grape, grapefruit, lemon, lentils, lettuce, linseed, mango, watermelon, cantaloupe, mustard, orange, peanut, peach, pear, peas, pepper, plum, poplar, potato, high erucic acid rapeseed, canola, safflower, sesame, soybean, spinach, strawberry, sugarbeet, sunflower, tea, tomato, banana, barley, date palm, field corn, garlic, millet, oat, oil palm, onion, pineapple, popcorn, rice, rye, sorghum, sudangrass, sugarcane, sweet corn, switchgrass, turf grasses, wheat, fir, pine, spruce, brown seaweeds, green seaweeds, red seaweeds, and microalgae.

24. The method of claim 1 or 6, wherein said plants are identified by determining whether or not one or more of said one or more selected plants has a difference in the level of at least one of lysine, glucose, fructose, and galactose compared to the corresponding level in a corresponding control plant that does not comprise said nucleic acid.

* * * * *

SEQUENCE LISTING

```
<160> NUMBER OF SEQ ID NOS: 28

<210> SEQ ID NO 1
<211> LENGTH: 859
<212> TYPE: DNA
<213> ORGANISM: Arabidopsis thaliana
<220> FEATURE:
<221> NAME/KEY: misc_feature
<222> LOCATION: (1)..(859)
<223> OTHER INFORMATION: Ceres CLONE ID no. 13832
<220> FEATURE:
<221> NAME/KEY: CDS
<222> LOCATION: (224)..(751)
```

<223> OTHER INFORMATION: Referenced by SEQ ID NO: 2

<400> SEQUENCE: 1

```
acgtgtttct gttttctct aattttctc ttgttgttct cgattaacga aaaagacttg    60
tcgttctcaa ttcttatcga tttaagaaca aatcatctaa cgaagattac ttccgaagat   120
cagaaacaaa cacaaactgt gaatcgttgt tgttaattc tctttaaaat cgccagaaga   180
aagagatctc cgttttctac agaagaaaag caagagagta agaatgggat cggaacaaaa   240
cgatagcaca agcttcacgc aatcgcaagc ttcagagcca aagctatgtg ttaaaggatg   300
tggtttcttt ggatcaccat caaacatgga tctctgttct aaatgttaca gaggcatttg   360
tgctgaggaa gctcaaacag cagttgctaa agctgctgtt gaaaaatctt tcaagccttc   420
tcctcctcgt agtctcttca tagcagaacc tcctgctgtt gttgtggaac ccaaacccga   480
aaaggcggca gttgttgttg tctcggccga gccatcttcc tcggcggttc ctgaggcgaa   540
cgagccatcg agacctgcac gaaccaaccg gtgtttgtgt tgtaacaaga aggttgggat   600
catggggttt aagtgcaaat gcgggagcac tatctgcggc gatcatcggt acccggagac   660
tcatgattgc agctttgatt tcaaagaagt tggacgtgga gagattgcca agctaatcc   720
tgtggttaag gctgataaaa ttcaaaggtt ctgaaatatg gaagttttt ctaagtattt   780
tggtggtaat tactcatttg tatttgaacc gatttggggg ttgtcttgga tggttttaat   840
ggattgtttc caaagggac                                              859
```

<210> SEQ ID NO 2
<211> LENGTH: 176
<212> TYPE: PRT
<213> ORGANISM: Arabidopsis thaliana
<220> FEATURE:
<221> NAME/KEY: misc_feature
<222> LOCATION: (117)..(157)
<223> OTHER INFORMATION: Pfam Name: zf-AN1; Pfam Description: AN1-like
    Zinc finger
<220> FEATURE:
<221> NAME/KEY: misc_feature
<222> LOCATION: (19)..(43)
<223> OTHER INFORMATION: Pfam Name: zf-A20; Pfam Description: A20-like
    zinc finger

<400> SEQUENCE: 2

```
Met Gly Ser Glu Gln Asn Asp Ser Thr Ser Phe Thr Gln Ser Gln Ala
 1               5                  10                  15

Ser Glu Pro Lys Leu Cys Val Lys Gly Cys Gly Phe Phe Gly Ser Pro
            20                  25                  30

Ser Asn Met Asp Leu Cys Ser Lys Cys Tyr Arg Gly Ile Cys Ala Glu
        35                  40                  45

Glu Ala Gln Thr Ala Val Ala Lys Ala Ala Val Glu Lys Ser Phe Lys
    50                  55                  60

Pro Ser Pro Arg Ser Leu Phe Ile Ala Glu Pro Pro Ala Val Val
65                  70                  75                  80

Val Glu Pro Lys Pro Glu Lys Ala Ala Val Val Val Ser Ala Glu
                85                  90                  95

Pro Ser Ser Ser Ala Val Pro Glu Ala Asn Glu Pro Ser Arg Pro Ala
            100                 105                 110

Arg Thr Asn Arg Cys Leu Cys Cys Asn Lys Lys Val Gly Ile Met Gly
        115                 120                 125

Phe Lys Cys Lys Cys Gly Ser Thr Ile Cys Gly Asp His Arg Tyr Pro
    130                 135                 140
```

```
Glu Thr His Asp Cys Ser Phe Asp Phe Lys Glu Val Gly Arg Gly Glu
145                 150                 155                 160

Ile Ala Lys Ala Asn Pro Val Val Lys Ala Asp Lys Ile Gln Arg Phe
                165                 170                 175
```

<210> SEQ ID NO 3
<211> LENGTH: 176
<212> TYPE: PRT
<213> ORGANISM: Arabidopsis thaliana
<220> FEATURE:
<221> NAME/KEY: misc_feature
<222> LOCATION: (1)..(176)
<223> OTHER INFORMATION: Public GI no. 30102906

<400> SEQUENCE: 3

```
Met Gly Ser Glu Gln Asn Asp Ser Thr Ser Phe Thr Gln Ser Gln Ala
1               5                   10                  15

Ser Glu Pro Lys Leu Cys Val Lys Gly Cys Gly Phe Phe Gly Ser Pro
                20                  25                  30

Ser Asn Met Asp Leu Cys Ser Lys Cys Tyr Arg Gly Ile Cys Ala Glu
            35                  40                  45

Glu Ala Gln Thr Ala Val Ala Lys Ala Ala Val Glu Lys Ser Phe Lys
50                  55                  60

Pro Ser Pro Pro Arg Ser Leu Phe Ile Ala Glu Pro Pro Ala Val Val
65                  70                  75                  80

Val Glu Pro Lys Pro Glu Lys Ala Ala Val Val Val Ser Ala Glu
                85                  90                  95

Pro Ser Ser Ala Val Pro Glu Ala Asn Glu Pro Ser Arg Pro Ala
            100                 105                 110

Arg Thr Asn Arg Cys Leu Cys Cys Asn Lys Lys Val Gly Ile Met Gly
            115                 120                 125

Phe Lys Cys Lys Cys Gly Ser Thr Phe Cys Gly Glu His Arg Tyr Pro
130                 135                 140

Glu Thr His Asp Cys Ser Phe Asp Phe Lys Glu Val Gly Arg Gly Glu
145                 150                 155                 160

Ile Ala Lys Ala Asn Pro Val Val Lys Ala Asp Lys Ile Gln Arg Phe
                165                 170                 175
```

<210> SEQ ID NO 4
<211> LENGTH: 172
<212> TYPE: PRT
<213> ORGANISM: Brassica napus
<220> FEATURE:
<221> NAME/KEY: misc_feature
<222> LOCATION: (1)..(172)
<223> OTHER INFORMATION: >CeresClone:962327
<220> FEATURE:
<221> NAME/KEY: misc_feature
<222> LOCATION: (143)..(143)
<223> OTHER INFORMATION: Xaa is any aa, unknown, or other
<220> FEATURE:
<221> NAME/KEY: misc_feature
<222> LOCATION: (151)..(151)
<223> OTHER INFORMATION: Xaa is any aa, unknown, or other

<400> SEQUENCE: 4

```
Met Ser Ser Glu Gln Asn Asn Ser Thr Ser Phe Pro Pro Thr Glu Pro
1               5                   10                  15

Lys Leu Cys Asp Asn Gly Cys Gly Phe Phe Gly Ser Pro Ser Asn Met
                20                  25                  30

Asn Leu Cys Ser Lys Cys Tyr Arg Ser Leu Arg Ala Glu Glu Asp Gln
            35                  40                  45
```

```
Thr Ala Val Ala Lys Ala Val Lys Asn Ser Leu Lys Leu Pro Ser
         50                  55                  60

Cys Ser Leu Ile Ile Thr Pro Glu Gln Lys Gln Pro Leu Glu Thr Lys
 65              70                  75                  80

Pro Ala Ser Val Val Val Thr Ala Glu Pro Ser Val Pro Ile Ala
                 85                  90                  95

Thr Gly Gln Glu Glu Ala Glu Pro Ser Lys Pro Ala Arg Thr Asn Arg
                100                 105                 110

Cys Phe Ser Cys Asn Lys Lys Val Gly Val Met Gly Phe Lys Cys Lys
            115                 120                 125

Cys Gly Ser Thr Phe Cys Gly Ser His Arg Tyr Pro Glu Lys Xaa Glu
        130                 135                 140

Cys Ser Phe Asp Phe Lys Xaa Val Gly Arg Asp Ala Ile Ala Lys Ala
145                 150                 155                 160

Asn Pro Val Ile Lys Ala Asp Lys Val Glu Arg Ile
                165                 170

<210> SEQ ID NO 5
<211> LENGTH: 175
<212> TYPE: PRT
<213> ORGANISM: Brassica napus
<220> FEATURE:
<221> NAME/KEY: misc_feature
<222> LOCATION: (1)..(175)
<223> OTHER INFORMATION: >CeresClone:1360570

<400> SEQUENCE: 5

Met Ser Ser Glu Gln Asn Asn Ser Thr Ser Phe Pro Pro Thr Glu Pro
 1               5                  10                  15

Lys Leu Cys Asp Asn Gly Cys Gly Phe Phe Gly Ser Pro Ser Asn Met
                20                  25                  30

Asn Leu Cys Ser Lys Cys Tyr Arg Ser Leu Arg Ala Glu Glu Asp Gln
            35                  40                  45

Thr Ala Val Ala Lys Ala Val Glu Lys Ser Leu Lys Leu Pro Ser
         50                  55                  60

Cys Asn Leu Ile Thr Ala Pro Glu Pro Lys Gln Pro Leu Glu Thr Lys
 65              70                  75                  80

Pro Ala Ser Leu Glu Thr Val Val Ile Ala Gly Thr Ser Ser Val Pro
                 85                  90                  95

Pro Val Ala Thr Gly Gln Asp Glu Gly Glu Pro Ser Lys Pro Thr Arg
                100                 105                 110

Pro Asn Arg Cys Phe Ser Cys Asn Lys Lys Val Gly Val Met Gly Phe
            115                 120                 125

Lys Cys Lys Cys Gly Ser Thr Phe Cys Gly Ser His Arg Tyr Pro Glu
        130                 135                 140

Lys His Glu Cys Ser Phe Asp Phe Lys Glu Val Gly Arg Gly Ala Ile
145                 150                 155                 160

Ala Lys Ala Asn Pro Val Val Lys Ala Asp Lys Val Gln Arg Ile
                165                 170                 175

<210> SEQ ID NO 6
<211> LENGTH: 158
<212> TYPE: PRT
<213> ORGANISM: Glycine max
<220> FEATURE:
<221> NAME/KEY: misc_feature
<222> LOCATION: (1)..(158)
<223> OTHER INFORMATION: >CeresClone:1101577
```

<400> SEQUENCE: 6

```
Met Ala Glu Glu His Arg Cys Gln Ala Pro Arg Phe Cys Ala Asn Asn
1               5                   10                  15

Cys Gly Phe Phe Gly Ser Pro Ala Thr Gln Asn Met Cys Ser Lys Cys
            20                  25                  30

Tyr Arg Asp Phe Gln Leu Lys Glu Gln Gln Ser Ser Asn Ala Lys Met
        35                  40                  45

Val Leu Asn Gln Ser Leu Val Pro Ser Pro Pro Ala Val Ile Ser
 50                  55                  60

Gln Pro Ser Ser Ser Ser Ala Ala Val Asp Pro Ser Ser Ala Val
65                  70                  75                  80

Val Asp Asp Ala Pro Arg Glu Ser Glu Val Lys Ala Pro Gln Gln
                85                  90                  95

Asn Arg Cys Met Thr Cys Arg Arg Val Gly Leu Thr Gly Phe Lys
            100                 105                 110

Cys Arg Cys Gly Met Met Leu Cys Gly Thr His Arg Tyr Pro Glu Gln
        115                 120                 125

His Ala Cys Glu Phe Asp Phe Lys Gly Met Gly Arg Glu Gln Ile Ala
    130                 135                 140

Lys Ala Asn Pro Val Val Lys Gly Glu Lys Leu Asp Lys Ile
145                 150                 155
```

<210> SEQ ID NO 7
<211> LENGTH: 161
<212> TYPE: PRT
<213> ORGANISM: Oryza sativa
<220> FEATURE:
<221> NAME/KEY: misc_feature
<222> LOCATION: (1)..(161)
<223> OTHER INFORMATION: Public GI no. 50934425

<400> SEQUENCE: 7

```
Met Ala Gln Glu Ser Trp Lys Asn Glu Ser Glu Thr Val His Thr
1               5                   10                  15

Pro Glu Ala Pro Ile Leu Cys Val Asn Asn Cys Gly Phe Phe Gly Ser
            20                  25                  30

Ser Met Thr Asn Asn Met Cys Ser Lys Cys Tyr Arg Asp Phe Val Lys
        35                  40                  45

Val Thr Thr Met Ala Ala Pro Val Val Glu Lys Lys Ala Phe Thr Pro
 50                  55                  60

Ala Ser Ser Ser Lys Thr Pro Leu Glu Pro Ala Lys Pro Asp Glu Val
65                  70                  75                  80

Pro Ala Ala Ala Val Glu Asp Lys Gln Ala Ala Gln Glu Pro Pro Lys
                85                  90                  95

Pro Pro Ser Asn Arg Cys Leu Ser Cys Arg Lys Lys Val Gly Leu Thr
            100                 105                 110

Gly Phe Gln Cys Arg Cys Gly Gly Thr Phe Cys Ser Thr His Arg Tyr
        115                 120                 125

Thr Glu Ala His Asp Cys Thr Phe Asp Tyr Lys Lys Ala Gly Arg Asp
    130                 135                 140

Gln Ile Ala Lys Gln Asn Pro Val Val Ile Ala Glu Lys Ile Asn Lys
145                 150                 155                 160

Ile
```

<210> SEQ ID NO 8

-continued

```
<211> LENGTH: 157
<212> TYPE: PRT
<213> ORGANISM: Musa acuminata
<220> FEATURE:
<221> NAME/KEY: misc_feature
<222> LOCATION: (1)..(157)
<223> OTHER INFORMATION: Public GI no. 40850574

<400> SEQUENCE: 8

Met Ala Gly Glu Ser Cys Asn Leu Asp Lys Asp Glu Ala Glu Ile Phe
1               5                   10                  15

Lys Pro Ser Pro Ser Ser Ser Pro Ser Pro Ser Pro Ser Pro Pro
            20                  25                  30

Ser Ser Ser Gln Pro Pro Pro Ser Ser Val Leu Leu Lys Pro Ser
        35                  40                  45

Glu Glu Ser Gly Ile Gln Arg Pro Glu Ile Pro Ser Pro Pro Ala
    50                  55                  60

Pro Thr Ile Thr Phe Ala Ala Ser Ser Thr Pro Lys Leu Asp Glu Glu
65                  70                  75                  80

Pro Ser Asn Pro Gly Glu Glu Ser Pro Ala Pro Val Arg Phe Ser Asn
                85                  90                  95

Arg Cys Ser Ala Cys Arg Lys Lys Val Gly Leu Thr Gly Phe Arg Cys
            100                 105                 110

Arg Cys Gly Asp Leu Phe Cys Gly Arg His Arg Tyr Ser Asp Ala His
        115                 120                 125

Glu Cys Ser Phe Asp Tyr Lys Ala Ala Gly Arg Glu Glu Ile Ala Lys
    130                 135                 140

Ala Asn Pro Val Ile Lys Ala Ala Lys Ile Ile Lys Ile
145                 150                 155

<210> SEQ ID NO 9
<211> LENGTH: 137
<212> TYPE: PRT
<213> ORGANISM: Phaseolus vulgaris
<220> FEATURE:
<221> NAME/KEY: misc_feature
<222> LOCATION: (1)..(137)
<223> OTHER INFORMATION: Public GI no. 7488772

<400> SEQUENCE: 9

Met Ala Gln Lys Ala Gln Lys Asn Asp Thr Asp Phe Lys Val Pro Glu
1               5                   10                  15

Pro Ile Thr Pro Cys Ala Thr Thr Ala Ala Ala Thr Ser Ile
            20                  25                  30

Ser Glu Pro Ser Arg Phe Phe Asp Ala Ala Thr Pro Ala Thr Ser Ser
        35                  40                  45

Arg Ser Pro Lys Arg Ser Leu Pro Leu Glu Asp Ala Ala Asn Ala Asp
    50                  55                  60

Arg Thr Val Ala Ser Glu Pro Lys Arg Ala Val Asn Arg Cys Ser Gly
65                  70                  75                  80

Cys Arg Arg Arg Val Gly Leu Thr Gly Phe Arg Cys Arg Cys Gly Asp
                85                  90                  95

Leu Phe Cys Ala Glu His Arg Tyr Thr Asp Arg His Asp Cys Ser Tyr
            100                 105                 110

Asp Tyr Lys Thr Val Gly Arg Glu Ala Ile Ala Arg Glu Asn Pro Val
        115                 120                 125

Val Lys Ala Ala Lys Ile Val Lys Val
    130                 135
```

```
<210> SEQ ID NO 10
<211> LENGTH: 161
<212> TYPE: PRT
<213> ORGANISM: Triticum aestivum
<220> FEATURE:
<221> NAME/KEY: misc_feature
<222> LOCATION: (1)..(161)
<223> OTHER INFORMATION: >CeresClone:701370

<400> SEQUENCE: 10

Met Ala Gln Glu Ser Trp Lys Glu Ala Glu Asp Thr Gly Val His Ala
1               5                   10                  15

Pro Glu Ala Pro Ile Met Cys Ile Asn Asn Cys Gly Phe Phe Gly Asn
            20                  25                  30

Arg Met Thr Glu Asn Met Cys Ser Lys Cys Tyr Arg Asp Thr Val Lys
        35                  40                  45

Ala Lys Ser Met Ala Leu Leu Val Glu Asn Lys Thr Ala Ala Ala Val
    50                  55                  60

Ala Ser Ser Pro Thr Pro Met Val Ala Glu Ile Lys Asp Glu Ala Ser
65                  70                  75                  80

Ala Ser Ala Lys Glu Gly Lys Arg Val Ala Glu Glu Ala Pro Lys
                85                  90                  95

Pro Pro Ser Asn Arg Cys Leu Ser Cys Arg Lys Lys Val Gly Leu Thr
            100                 105                 110

Gly Phe Lys Cys Arg Cys Gly Asp Thr Phe Cys Ser Met His Arg Tyr
        115                 120                 125

Ala Asp Ala His Asp Cys Lys Phe Asp Tyr Lys Gln Ala Gly Arg Glu
    130                 135                 140

Gln Ile Ala Gln Gln Asn Pro Val Val Lys Ala Asp Lys Val Thr Arg
145                 150                 155                 160

Phe

<210> SEQ ID NO 11
<211> LENGTH: 137
<212> TYPE: PRT
<213> ORGANISM: Gossypium hirsutum
<220> FEATURE:
<221> NAME/KEY: misc_feature
<222> LOCATION: (1)..(137)
<223> OTHER INFORMATION: Public GI no. 66271037

<400> SEQUENCE: 11

Met Ala Glu Glu His Arg Cys Gln Ala Pro Gln Leu Cys Ala Asn Asn
1               5                   10                  15

Cys Gly Phe Phe Gly Ser Pro Thr Thr Gln Asn Leu Cys Ser Glu Cys
            20                  25                  30

Tyr Arg Gly Leu Gln Leu Lys Glu Gln Gln Ser Ser Ser Ala Lys Gln
        35                  40                  45

Ala Phe Asn His Thr Leu Val Pro Ser Ser Ser Ser Leu Pro Ser Ser
    50                  55                  60

Ser Ser Ala Arg Ser Ser Phe Ser Ala Ser Leu Pro Ala Lys Glu Glu
65                  70                  75                  80

Pro Ser Ala Gly Thr Lys Glu Thr Lys Val Val Glu Glu Glu Val
                85                  90                  95

Gln Val Thr Pro Asn Arg Cys Leu Ser Cys Lys Lys Arg Val Gly Leu
            100                 105                 110

Thr Gly Phe Lys Cys Arg Cys Gly Met Val Phe Cys Gly Ile His Arg
        115                 120                 125
```

```
Tyr Pro Gly Thr Thr Cys Leu Cys Phe
    130                 135
```

<210> SEQ ID NO 12
<211> LENGTH: 173
<212> TYPE: PRT
<213> ORGANISM: Prunus armeniaca
<220> FEATURE:
<221> NAME/KEY: misc_feature
<222> LOCATION: (1)..(173)
<223> OTHER INFORMATION: Public GI no. 5031281

<400> SEQUENCE: 12

```
Met Glu His Glu Glu Thr Gly Cys Gln Pro His Pro Glu Gly Pro Ile
1               5                   10                  15

Leu Cys Val Asn Asn Cys Gly Phe Phe Gly Ser Val Ala Thr Arg Asn
            20                  25                  30

Met Cys Ser Lys Cys His Lys Asp Met Met Leu Lys Glu Glu Gln Ala
        35                  40                  45

Lys Leu Ala Ala Ser Ser Phe Gly Asn Ile Val Asn Gly Thr Ser Asn
    50                  55                  60

Ser Asn Gly Asn Glu Pro Val Val Ala Ala Gly Val Asp Val Gln Ala
65                  70                  75                  80

His Leu Val Glu Pro Lys Thr Ile Ser Leu Gln Pro Ser Phe Ser Phe
                85                  90                  95

Gly Ser Gly Ser Gly Gly Ser Gly Glu Ala Lys Pro Glu Gly Pro Lys
            100                 105                 110

Arg Cys Gly Thr Cys Asn Lys Arg Val Gly Leu Thr Gly Phe Asn Cys
        115                 120                 125

Arg Cys Gly His Leu Phe Cys Ala Val His Arg Tyr Ser Asp Lys His
    130                 135                 140

Asp Cys Pro Tyr Asp Tyr His Thr Ala Ala Arg Asp Val Ile Ala Lys
145                 150                 155                 160

Ala Asn Pro Val Val Lys Ala Asp Lys Leu Glu Lys Ile
                165                 170
```

<210> SEQ ID NO 13
<211> LENGTH: 171
<212> TYPE: PRT
<213> ORGANISM: Oryza sativa
<220> FEATURE:
<221> NAME/KEY: misc_feature
<222> LOCATION: (1)..(171)
<223> OTHER INFORMATION: Public GI no. 35187687

<400> SEQUENCE: 13

```
Met Glu His Lys Glu Thr Gly Cys Gln Gln Pro Lys Gly Pro Ile Leu
1               5                   10                  15

Cys Ile Asn Asn Cys Gly Phe Phe Gly Ser Ala Ala Thr Met Asn Met
            20                  25                  30

Cys Ser Lys Cys His Lys Glu Met Ile Met Lys Gln Glu Gln Ala Lys
        35                  40                  45

Leu Ala Ala Ser Ser Ile Asp Ser Ile Val Asn Gly Asp Ser Gly
    50                  55                  60

Lys Glu Pro Ile Ile Ala Gly His Ala Glu Val Ala Val Ala Gln Val
65                  70                  75                  80

Glu Val Lys Thr Leu Val Ala Gln Pro Ala Glu Ile Ala Gly Pro Ser
                85                  90                  95
```

```
Glu Gly Val Thr Val Asn Pro Lys Gly Arg Glu Gly Pro Asn Arg Cys
            100                 105                 110

Ser Thr Cys Arg Lys Arg Val Gly Leu Thr Gly Phe Asn Cys Arg Cys
            115                 120                 125

Gly Asn Leu Tyr Cys Ala Met His Arg Tyr Ser Asp Lys His Asp Cys
        130                 135                 140

Gln Phe Asp Tyr Arg Thr Ala Ala Arg Asp Ala Ile Ala Lys Ala Asn
145                 150                 155                 160

Pro Val Val Lys Ala Glu Lys Leu Asp Lys Ile
                165                 170

<210> SEQ ID NO 14
<211> LENGTH: 1503
<212> TYPE: DNA
<213> ORGANISM: Arabidopsis thaliana
<220> FEATURE:
<221> NAME/KEY: misc_feature
<222> LOCATION: (1)..(1503)
<223> OTHER INFORMATION: Ceres cDNA ID no. 23530177
<220> FEATURE:
<221> NAME/KEY: CDS
<222> LOCATION: (1)..(1500)
<223> OTHER INFORMATION: Referenced by SEQ ID NO: 15

<400> SEQUENCE: 14
atgtcgatct ctctctattt cctttttgctc ttgcctctct ttttaatctt cttcaaaaag      60
ctctcacctt ctaaaggaaa gcttcctcct ggacctctag gtcttccgat tatcggaaac     120
ttgcaccaac ttggaaaatc tctccataga tctttccata aactatctca aaactatgga     180
cccgtgatgt ttctacattt cggtgtggtc cctgtggttg tggtctccac aagagaagca     240
gctgaagaag ttctcaagac tcatgatctc gagacttgta cccgaccaaa gctaaccgcg     300
accaagttgt tttcttacaa ctacaaagac attggcttcg ctcaatacgg tgatgactgg     360
agagagatga ggaagcttgc gatgctcgag ctttttagct cgaaaaagct caaggctttc     420
aggtatatta gaagaagaga gagtgaagtc ctagtcaata aactctcgaa atctgctgag     480
acacgaacta tggtagactt gagaaaagct cttttctctt ataccgctag tatcgtatgt     540
aggctcgctt ttggacagaa cttccatgag tgcgattttg tcgatatgga taaagttgaa     600
gatcttgtgc tcgaatctga gaccaatctt ggctcattcg cgttcactga cttcttcccc     660
gcagggcttg gtgggttat agaccggatc tctggccaac attcggagtt gcacaaagcc      720
tttgccagac ttagtaattt tttttcaacat gtgatcgatg atcacttgaa gcctgggcaa     780
tctcaagatc attcagacat cattggtgtc atgttagata tgatcaataa agagagtaaa     840
gtcggttcct tccaagtcac ctacgaccat cttaaaggag tcatgtcgga tgtgtttta      900 gcgggagtga acgcaggagc gatcacaatg atatgggcga tgacagagct agccagacat     960
ccgagagtga tgaaaaaact tcaacaagag attcgagaaa tactcggaga caacaaagaa    1020
aaaatcacgg aacaagatct cgaaaaggtt cactacttga acttgtgat cgaagaaaca     1080 ttcagattac atcctccagc tcctctcttg ctacctagag agacaatgtc tgacttaaag    1140
attcaaggct acaatattcc caagaacacg atgatcgaga tcaatactta ttcaatagga    1200
cgcgatccta attgctggga aaacctaac gatttcaacc ccgagagatt tatcgatagc     1260
cctgtcgaat ataagggtca acattatgag ttgttgcctt tggtgctgg tcgcaggatt     1320 tgtccaggaa tggctacggg gataactatc gtcgagctcg gtttacttaa tgttctttac    1380
ttctttgatt ggagtttgcc tgatggaatg aaaattgaag acatagacat ggaagaagct    1440
```

```
ggagctttcg tcgtcgccaa gaaagtccct cttgagctaa ttccaactcc acatcagtgg   1500
tga                                                                 1503
```

<210> SEQ ID NO 15
<211> LENGTH: 500
<212> TYPE: PRT
<213> ORGANISM: Arabidopsis thaliana
<220> FEATURE:
<221> NAME/KEY: misc_feature
<222> LOCATION: (29)..(495)
<223> OTHER INFORMATION: Pfam Name: p450; Pfam Description: Cytochrome
      P450

<400> SEQUENCE: 15

```
Met Ser Ile Ser Leu Tyr Phe Leu Leu Leu Pro Leu Phe Leu Ile
1               5                   10                  15

Phe Phe Lys Lys Leu Ser Pro Ser Lys Gly Lys Leu Pro Pro Gly Pro
            20                  25                  30

Leu Gly Leu Pro Ile Ile Gly Asn Leu His Gln Leu Gly Lys Ser Leu
        35                  40                  45

His Arg Ser Phe His Lys Leu Ser Gln Asn Tyr Gly Pro Val Met Phe
 50                  55                  60

Leu His Phe Gly Val Val Pro Val Val Val Ser Thr Arg Glu Ala
65                  70                  75                  80

Ala Glu Glu Val Leu Lys Thr His Asp Leu Glu Thr Cys Thr Arg Pro
                85                  90                  95

Lys Leu Thr Ala Thr Lys Leu Phe Ser Tyr Asn Tyr Lys Asp Ile Gly
            100                 105                 110

Phe Ala Gln Tyr Gly Asp Asp Trp Arg Glu Met Arg Lys Leu Ala Met
        115                 120                 125

Leu Glu Leu Phe Ser Ser Lys Lys Leu Lys Ala Phe Arg Tyr Ile Arg
130                 135                 140

Glu Glu Glu Ser Glu Val Leu Val Asn Lys Leu Ser Lys Ser Ala Glu
145                 150                 155                 160

Thr Arg Thr Met Val Asp Leu Arg Lys Ala Leu Phe Ser Tyr Thr Ala
                165                 170                 175

Ser Ile Val Cys Arg Leu Ala Phe Gly Gln Asn Phe His Glu Cys Asp
            180                 185                 190

Phe Val Asp Met Asp Lys Val Glu Asp Leu Val Leu Glu Ser Glu Thr
        195                 200                 205

Asn Leu Gly Ser Phe Ala Phe Thr Asp Phe Phe Pro Ala Gly Leu Gly
210                 215                 220

Trp Val Ile Asp Arg Ile Ser Gly Gln His Ser Glu Leu His Lys Ala
225                 230                 235                 240

Phe Ala Arg Leu Ser Asn Phe Gln His Val Ile Asp Asp His Leu
                245                 250                 255

Lys Pro Gly Gln Ser Gln Asp His Ser Asp Ile Ile Gly Val Met Leu
            260                 265                 270

Asp Met Ile Asn Lys Glu Ser Lys Val Gly Ser Phe Gln Val Thr Tyr
        275                 280                 285

Asp His Leu Lys Gly Val Met Ser Asp Val Phe Leu Ala Gly Val Asn
290                 295                 300

Ala Gly Ala Ile Thr Met Ile Trp Ala Met Thr Glu Leu Ala Arg His
305                 310                 315                 320

Pro Arg Val Met Lys Lys Leu Gln Gln Glu Ile Arg Glu Ile Leu Gly
                325                 330                 335
```

-continued

```
Asp Asn Lys Glu Lys Ile Thr Glu Gln Asp Leu Glu Lys Val His Tyr
            340                 345                 350
Leu Lys Leu Val Ile Glu Glu Thr Phe Arg Leu His Pro Pro Ala Pro
            355                 360                 365
Leu Leu Leu Pro Arg Glu Thr Met Ser Asp Leu Lys Ile Gln Gly Tyr
            370                 375                 380
Asn Ile Pro Lys Asn Thr Met Ile Glu Ile Asn Thr Tyr Ser Ile Gly
385                 390                 395                 400
Arg Asp Pro Asn Cys Trp Glu Lys Pro Asn Asp Phe Asn Pro Glu Arg
                405                 410                 415
Phe Ile Asp Ser Pro Val Glu Tyr Lys Gly Gln His Tyr Glu Leu Leu
                420                 425                 430
Pro Phe Gly Ala Gly Arg Arg Ile Cys Pro Gly Met Ala Thr Gly Ile
            435                 440                 445
Thr Ile Val Glu Leu Gly Leu Leu Asn Val Leu Tyr Phe Phe Asp Trp
            450                 455                 460
Ser Leu Pro Asp Gly Met Lys Ile Glu Asp Ile Asp Met Glu Glu Ala
465                 470                 475                 480
Gly Ala Phe Val Val Ala Lys Lys Val Pro Leu Glu Leu Ile Pro Thr
                485                 490                 495
Pro His Gln Trp
```

<210> SEQ ID NO 16
<211> LENGTH: 502
<212> TYPE: PRT
<213> ORGANISM: Persea americana
<220> FEATURE:
<221> NAME/KEY: misc_feature
<222> LOCATION: (1)..(502)
<223> OTHER INFORMATION: Public GI no. 25282608

<400> SEQUENCE: 16

```
Met Ala Ile Leu Val Ser Leu Leu Phe Leu Ala Ile Ala Leu Thr Phe
1               5                   10                  15
Phe Leu Leu Lys Leu Asn Glu Lys Arg Glu Lys Lys Pro Asn Leu Pro
            20                  25                  30
Pro Ser Pro Pro Asn Leu Pro Ile Ile Gly Asn Leu His Gln Leu Gly
            35                  40                  45
Asn Leu Pro His Arg Ser Leu Arg Ser Leu Ala Asn Glu Leu Gly Pro
        50                  55                  60
Leu Ile Leu Leu His Leu Gly His Ile Pro Thr Leu Ile Val Ser Thr
65                  70                  75                  80
Ala Glu Ile Ala Glu Gly Ile Leu Lys Thr His Asp Leu Ile Phe Ala
                85                  90                  95
Ser Arg Pro Ser Thr Thr Ala Ala Arg Arg Ile Phe Tyr Asp Cys Thr
                100                 105                 110
Asp Val Ala Phe Ser Pro Tyr Gly Glu Tyr Trp Arg Gln Val Arg Lys
            115                 120                 125
Ile Cys Val Leu Glu Leu Leu Ser Ile Lys Arg Val Asn Ser Tyr Arg
        130                 135                 140
Ser Ile Arg Glu Glu Glu Val Gly Leu Met Met Glu Arg Ile Ser Gln
145                 150                 155                 160
Ser Cys Ser Thr Gly Glu Ala Val Asn Leu Ser Glu Leu Leu Leu Leu
                165                 170                 175
Leu Ser Ser Gly Thr Ile Thr Arg Val Ala Phe Gly Lys Lys Tyr Glu
```

-continued

```
                180                 185                 190
Gly Glu Glu Arg Lys Asn Lys Phe Ala Asp Leu Ala Thr Glu Leu
            195                 200                 205

Thr Thr Leu Met Gly Ala Phe Phe Val Gly Asp Tyr Phe Pro Ser Phe
210                 215                 220

Ala Trp Val Asp Val Leu Thr Gly Met Asp Ala Arg Leu Lys Arg Asn
225                 230                 235                 240

His Gly Glu Leu Asp Ala Phe Val Asp His Val Ile Asp His Leu
            245                 250                 255

Leu Ser Arg Lys Ala Asn Gly Ser Asp Gly Val Glu Gln Lys Asp Leu
            260                 265                 270

Val Asp Val Leu Leu His Leu Gln Lys Asp Ser Ser Leu Gly Val His
            275                 280                 285

Leu Asn Arg Asn Asn Leu Lys Ala Val Ile Leu Asp Met Phe Ser Gly
            290                 295                 300

Gly Thr Asp Thr Thr Ala Val Thr Leu Glu Trp Ala Met Ala Glu Leu
305                 310                 315                 320

Ile Lys His Pro Asp Val Met Glu Lys Ala Gln Gln Glu Val Arg Arg
                325                 330                 335

Val Val Gly Lys Lys Ala Lys Val Glu Glu Glu Asp Leu His Gln Leu
            340                 345                 350

His Tyr Leu Lys Leu Ile Ile Lys Glu Thr Leu Arg Leu His Pro Val
            355                 360                 365

Ala Pro Leu Leu Val Pro Arg Glu Ser Thr Arg Asp Val Val Ile Arg
            370                 375                 380

Gly Tyr His Ile Pro Ala Lys Thr Arg Val Phe Ile Asn Ala Trp Ala
385                 390                 395                 400

Ile Gly Arg Asp Pro Lys Ser Trp Glu Asn Ala Glu Glu Phe Leu Pro
                405                 410                 415

Glu Arg Phe Val Asn Asn Ser Val Asp Phe Lys Gly Gln Asp Phe Gln
            420                 425                 430

Leu Ile Pro Phe Gly Ala Gly Arg Arg Gly Cys Pro Gly Ile Ala Phe
            435                 440                 445

Gly Ile Ser Ser Val Glu Ile Ser Leu Ala Asn Leu Leu Tyr Trp Phe
450                 455                 460

Asn Trp Glu Leu Pro Gly Asp Leu Thr Lys Glu Asp Leu Asp Met Ser
465                 470                 475                 480

Glu Ala Val Gly Ile Thr Val His Met Lys Pro Leu Gln Leu Val
            485                 490                 495

Ala Lys Arg His Leu Ser
            500
```

<210> SEQ ID NO 17
<211> LENGTH: 499
<212> TYPE: PRT
<213> ORGANISM: Arabidopsis thaliana
<220> FEATURE:
<221> NAME/KEY: misc_feature
<222> LOCATION: (1)..(499)
<223> OTHER INFORMATION: Public GI no. 11994438

<400> SEQUENCE: 17

```
Met Ser Ile Phe Leu Cys Phe Leu Leu Leu Pro Leu Phe Leu Val
1               5                   10                  15

Phe Tyr Lys Arg Leu Leu Pro Ser Lys Gly Lys Leu Pro Pro Gly Pro
                20                  25                  30
```

-continued

```
Ile Ser Leu Pro Ile Ile Gly Asn Leu His Gln Leu Gly Lys Ser Leu
         35                  40                  45

His Arg Ser Phe Tyr Lys Leu Ser Gln Glu Tyr Gly Pro Val Met Phe
         50                  55                  60

Leu Arg Phe Gly Val Val Pro Val Val Phe Ser Thr Lys Glu Ala
 65                  70                  75                  80

Ala Glu Glu Val Leu Lys Thr His Asp Leu Glu Thr Cys Thr Arg Pro
                     85                  90                  95

Lys Leu Ser Ala Thr Gly Leu Phe Thr Tyr Asn Phe Lys Asp Ile Gly
                    100                 105                 110

Phe Ala Gln Tyr Gly Glu Asp Trp Arg Glu Met Arg Lys Leu Ala Met
                115                 120                 125

Leu Glu Leu Phe Ser Ser Lys Leu Lys Ala Phe Arg Tyr Ile Arg
            130                 135                 140

Glu Glu Glu Ser Glu Leu Leu Val Lys Val Thr Glu Ser Ala Gln
145                 150                 155                 160

Thr Gln Thr Leu Val Asp Leu Arg Lys Ala Leu Phe Ser Tyr Thr Ala
                    165                 170                 175

Ser Ile Val Cys Arg Leu Ala Phe Gly Gln Asn Phe His Glu Cys Asp
                180                 185                 190

Phe Val Asp Met Asp Lys Val Glu Glu Leu Val Leu Glu Ser Glu Thr
            195                 200                 205

Asn Leu Gly Ser Phe Ala Phe Ile Asp Phe Pro Ala Gly Leu Gly
    210                 215                 220

Trp Ala Ile Asp Arg Ile Ser Gly Gln His Ser Arg Leu His Lys Ala
225                 230                 235                 240

Phe Ala Arg Leu Ser Asn Phe Phe Gln His Val Ile Asp Asp His Leu
                    245                 250                 255

Lys Pro Trp Gln Ser Glu Asp His Ser Asp Ile Val Gly Val Met Leu
                260                 265                 270

Asp Met Ile Asn Lys Glu Ser Lys Val Gly Ser Phe Lys Val Thr Tyr
            275                 280                 285

Asp His Leu Lys Gly Val Met Ser Asp Val Phe Leu Ala Gly Val Asn
    290                 295                 300

Ala Gly Ala Ile Thr Met Ile Trp Ala Leu Thr Glu Leu Thr Arg His
305                 310                 315                 320

Pro Arg Val Met Lys Lys Leu Gln Gln Glu Ile Arg Glu Leu Leu Gly
                    325                 330                 335

Asp Asn Lys Glu Lys Ile Thr Glu Gln Asp Leu Glu Lys Val His Tyr
                340                 345                 350

Leu Lys Leu Val Ile Gln Glu Thr Phe Arg Leu His Pro Pro Ala Pro
            355                 360                 365

Leu Leu Leu Pro Arg Glu Thr Met Ser Asp Val Lys Ile Gln Gly Tyr
    370                 375                 380

Asn Ile Pro Lys Asn Thr Met Ile Glu Ile Asn Thr Tyr Ala Ile Gly
385                 390                 395                 400

Arg Asp Pro Asn Cys Trp Thr Asn Pro Asn Glu Phe Ile Pro Glu Arg
                    405                 410                 415

Phe Val Asp Ser Pro Ile Asp Tyr Lys Gly Gln His Phe Glu Leu Leu
                420                 425                 430

Pro Phe Gly Gly Gly Arg Arg Ile Cys Pro Gly Met Ala Thr Gly Met
            435                 440                 445
```

```
Thr Ile Val Glu Leu Gly Leu Leu Asn Val Leu Tyr Phe Phe Asp Trp
    450                 455                 460

Ser Leu Pro Tyr Gly Met Ala Ile Ala Asp Ile Asn Met Glu Glu Ala
465                 470                 475                 480

Gly Ala Phe Val Ile Ala Lys Lys Val Pro Leu Glu Leu Val Pro Val
                485                 490                 495

Leu His Tyr

<210> SEQ ID NO 18
<211> LENGTH: 499
<212> TYPE: PRT
<213> ORGANISM: Glycine max
<220> FEATURE:
<221> NAME/KEY: misc_feature
<222> LOCATION: (1)..(499)
<223> OTHER INFORMATION: Public GI no. 3334659

<400> SEQUENCE: 18

Met Ile Ser Phe Thr Val Phe Val Phe Leu Thr Leu Leu Phe Thr Leu
1               5                   10                  15

Ser Leu Val Lys Gln Leu Arg Lys Pro Thr Ala Glu Lys Arg Arg Leu
            20                  25                  30

Leu Pro Pro Gly Pro Arg Lys Leu Pro Phe Ile Gly Asn Leu His Gln
        35                  40                  45

Leu Gly Thr Leu Pro His Gln Ser Leu Gln Tyr Leu Ser Asn Lys His
    50                  55                  60

Gly Pro Leu Met Phe Leu Gln Leu Gly Ser Ile Pro Thr Leu Val Val
65                  70                  75                  80

Ser Ser Ala Glu Met Ala Arg Glu Ile Phe Lys Asn His Asp Ser Val
                85                  90                  95

Phe Ser Gly Arg Pro Ser Leu Tyr Ala Ala Asn Arg Leu Gly Tyr Gly
            100                 105                 110

Ser Thr Val Ser Phe Ala Pro Tyr Gly Glu Tyr Trp Arg Glu Met Arg
        115                 120                 125

Lys Ile Met Ile Leu Glu Leu Leu Ser Pro Lys Arg Val Gln Ser Phe
    130                 135                 140

Glu Ala Val Arg Phe Glu Glu Val Lys Leu Leu Leu Gln Thr Ile Ala
145                 150                 155                 160

Leu Ser His Gly Pro Val Asn Leu Ser Glu Leu Thr Leu Ser Leu Thr
                165                 170                 175

Asn Asn Ile Val Cys Arg Ile Ala Leu Gly Lys Arg Asn Arg Ser Gly
            180                 185                 190

Ala Asp Asp Ala Asn Lys Val Ser Glu Met Leu Lys Glu Thr Gln Ala
        195                 200                 205

Met Leu Gly Gly Phe Phe Pro Val Asp Phe Phe Pro Arg Leu Gly Trp
    210                 215                 220

Leu Asn Lys Phe Ser Gly Leu Glu Asn Arg Leu Glu Lys Ile Phe Arg
225                 230                 235                 240

Glu Met Asp Asn Phe Tyr Asp Gln Val Ile Lys Glu His Ile Ala Asp
                245                 250                 255

Asn Ser Ser Glu Arg Ser Gly Ala Glu His Glu Asp Val Val Asp Val
            260                 265                 270

Leu Leu Arg Val Gln Lys Asp Pro Asn Gln Ala Ile Ala Ile Thr Asp
        275                 280                 285

Asp Gln Ile Lys Gly Val Leu Val Asp Ile Phe Val Ala Gly Thr Asp
    290                 295                 300
```

```
Thr Ala Ser Ala Thr Ile Ile Trp Ile Met Ser Glu Leu Ile Arg Asn
305                 310                 315                 320

Pro Lys Ala Met Lys Arg Ala Gln Glu Glu Val Arg Asp Leu Val Thr
            325                 330                 335

Gly Lys Glu Met Val Glu Ile Asp Leu Ser Lys Leu Leu Tyr Ile
            340                 345                 350

Lys Ser Val Val Lys Glu Val Leu Arg Leu His Pro Ala Pro Leu
            355                 360                 365

Leu Val Pro Arg Glu Ile Thr Glu Asn Cys Thr Ile Lys Gly Phe Glu
            370                 375                 380

Ile Pro Ala Lys Thr Arg Val Leu Val Asn Ala Lys Ser Ile Ala Met
385                 390                 395                 400

Asp Pro Cys Cys Trp Glu Asn Pro Asn Glu Phe Leu Pro Glu Arg Phe
                405                 410                 415

Leu Val Ser Pro Ile Asp Phe Lys Gly Gln His Phe Glu Met Leu Pro
            420                 425                 430

Phe Gly Val Gly Arg Arg Gly Cys Pro Gly Val Asn Phe Ala Met Pro
            435                 440                 445

Val Val Glu Leu Ala Leu Ala Asn Leu Leu Phe Arg Phe Asp Trp Glu
            450                 455                 460

Leu Pro Leu Gly Leu Gly Ile Gln Asp Leu Asp Met Glu Glu Ala Ile
465                 470                 475                 480

Gly Ile Thr Ile His Lys Lys Ala His Leu Trp Leu Lys Ala Thr Pro
                485                 490                 495

Phe Cys Glu

<210> SEQ ID NO 19
<211> LENGTH: 511
<212> TYPE: PRT
<213> ORGANISM: Manihot esculenta
<220> FEATURE:
<221> NAME/KEY: misc_feature
<222> LOCATION: (1)..(511)
<223> OTHER INFORMATION: Public GI no. 37788136

<400> SEQUENCE: 19

Met Ser Val Ala Ile Leu Thr Ser Leu Pro Pro Gln Trp Leu Ser Ile
1               5                   10                  15

Leu Ala Val Phe Leu Leu Pro Ile Leu Thr Leu Leu Phe Arg Gly
            20                  25                  30

Lys Asp Asp Asn Gln Lys Lys Gly Leu Lys Leu Pro Pro Gly Pro Arg
            35                  40                  45

Gln Leu Pro Leu Ile Gly Asn Leu His Gln Leu Gly Gln Pro Tyr
        50                  55                  60

Val Asp Phe Trp Lys Met Ala Lys Lys Tyr Gly Pro Val Met Tyr Leu
65                  70                  75                  80

Gln Leu Gly Arg Cys Pro Thr Val Val Leu Ser Ser Thr Glu Thr Ser
                85                  90                  95

Lys Glu Leu Met Lys Asp Arg Asp Val Glu Cys Cys Ser Arg Pro Leu
            100                 105                 110

Ser Val Gly Pro Gly Gln Leu Ser Tyr Asn Phe Leu Asp Val Ala Phe
            115                 120                 125

Ser Pro Tyr Ser Asp Tyr Trp Arg Glu Met Arg Lys Leu Phe Ile Phe
        130                 135                 140

Glu Leu Leu Ser Met Arg Arg Val Gln Thr Phe Trp Tyr Ala Arg Glu
```

```
                    145                 150                 155                 160
Glu Gln Met Asp Lys Met Ile Glu Ile Leu Asp Gly Ala Tyr Pro Asn
                165                 170                 175

Pro Val Asn Leu Thr Glu Lys Val Phe Asn Met Met Asp Gly Ile Ile
            180                 185                 190

Gly Thr Ile Ala Phe Gly Arg Thr Thr Tyr Ala Gln Gln Glu Phe Arg
        195                 200                 205

Asp Gly Phe Val Lys Val Leu Ala Thr Met Asp Met Leu Asp Asn
    210                 215                 220

Phe His Ala Glu Asn Phe Phe Pro Val Val Gly Arg Phe Ile Asp Ser
225                 230                 235                 240

Leu Thr Gly Ala Leu Ala Lys Arg Gln Arg Thr Phe Thr Asp Val Asp
                245                 250                 255

Arg Tyr Phe Glu Lys Val Ile Glu Gln His Leu Asp Pro Asn Arg Pro
            260                 265                 270

Lys Pro Glu Thr Glu Asp Ile Val Asp Val Leu Ile Gly Leu Met Lys
        275                 280                 285

Asp Glu Ser Thr Ser Phe Lys Ile Thr Lys Asp His Val Lys Ala Ile
    290                 295                 300

Leu Met Asn Val Phe Val Gly Gly Ile Asp Thr Ser Ala Val Thr Ile
305                 310                 315                 320

Thr Trp Ala Phe Ser Glu Leu Leu Lys Asn Pro Lys Leu Met Lys Lys
                325                 330                 335

Ala Gln Glu Glu Val Arg Arg Ala Val Gly Pro Asn Lys Arg Arg Val
            340                 345                 350

Glu Gly Lys Glu Val Glu Lys Ile Lys Tyr Ile Asp Cys Ile Val Lys
        355                 360                 365

Glu Thr Phe Arg Lys His Pro Pro Val Pro Leu Leu Val Pro His Phe
    370                 375                 380

Ser Met Lys His Cys Lys Ile Gly Gly Tyr Asp Ile Leu Pro Gly Thr
385                 390                 395                 400

Thr Ile Tyr Val Asn Ala Trp Ala Met Gly Lys Asp Pro Thr Ile Trp
                405                 410                 415

Glu Asn Pro Glu Glu Tyr Asn Pro Asp Arg Phe Met Asn Ser Glu Val
            420                 425                 430

Asp Phe Arg Gly Ser Asp Phe Glu Leu Val Pro Phe Gly Ala Gly Arg
        435                 440                 445

Arg Ile Cys Pro Gly Leu Ala Met Gly Thr Thr Ala Val Lys Tyr Ile
    450                 455                 460

Leu Ser Asn Leu Leu Tyr Gly Trp Asp Tyr Glu Met Pro Arg Gly Lys
465                 470                 475                 480

Lys Phe Glu Asp Phe Pro Leu Ile Glu Glu Gly Gly Leu Thr Val His
                485                 490                 495

Asn Lys Gln Asp Ile Met Val Ile Pro Lys Lys His Lys Trp Asp
            500                 505                 510

<210> SEQ ID NO 20
<211> LENGTH: 531
<212> TYPE: PRT
<213> ORGANISM: Sorghum bicolor
<220> FEATURE:
<221> NAME/KEY: misc_feature
<222> LOCATION: (1)..(531)
<223> OTHER INFORMATION: Public GI no. 5915841

<400> SEQUENCE: 20
```

-continued

```
Met Ala Thr Thr Ala Thr Pro Gln Leu Leu Gly Gly Ser Val Pro Gln
1               5                   10                  15

Gln Trp Gln Thr Cys Leu Leu Val Leu Leu Pro Val Leu Leu Val Ser
            20                  25                  30

Tyr Tyr Leu Leu Thr Ser Arg Ser Arg Asn Arg Ser Arg Ser Gly Lys
        35                  40                  45

Leu Gly Gly Ala Pro Arg Leu Pro Pro Gly Pro Ala Gln Leu Pro Ile
    50                  55                  60

Leu Gly Asn Leu His Leu Leu Gly Pro Leu Pro His Lys Asn Leu Arg
65                  70                  75                  80

Glu Leu Ala Arg Arg Tyr Gly Pro Val Met Gln Leu Arg Leu Gly Thr
                85                  90                  95

Val Pro Thr Val Val Ser Ser Ala Glu Ala Ala Arg Glu Val Leu
                100                 105                 110

Lys Val His Asp Val Asp Cys Cys Ser Arg Pro Ala Ser Pro Gly Pro
            115                 120                 125

Lys Arg Leu Ser Tyr Asp Leu Lys Asn Val Gly Phe Ala Pro Tyr Gly
    130                 135                 140

Glu Tyr Trp Arg Glu Met Arg Lys Leu Phe Ala Leu Glu Leu Leu Ser
145                 150                 155                 160

Met Arg Arg Val Lys Ala Ala Cys Tyr Ala Arg Glu Gln Glu Met Asp
                165                 170                 175

Arg Leu Val Ala Asp Leu Asp Arg Ala Ala Ser Lys Ala Ser Ile
                180                 185                 190

Val Leu Asn Asp His Val Phe Ala Leu Thr Asp Gly Ile Ile Gly Thr
            195                 200                 205

Val Ala Phe Gly Asn Ile Tyr Ala Ser Lys Gln Phe Ala His Lys Glu
    210                 215                 220

Arg Phe Gln His Val Leu Asp Asp Ala Met Asp Met Met Ala Ser Phe
225                 230                 235                 240

Ser Ala Glu Asp Phe Phe Pro Asn Ala Ala Gly Arg Leu Ala Asp Arg
                245                 250                 255

Leu Ser Gly Phe Leu Ala Arg Arg Glu Arg Ile Phe Asn Glu Leu Asp
            260                 265                 270

Val Phe Phe Glu Lys Val Ile Asp Gln His Met Asp Pro Ala Arg Pro
    275                 280                 285

Val Pro Asp Asn Gly Gly Asp Leu Val Asp Val Leu Ile Asn Leu Cys
    290                 295                 300

Lys Glu His Asp Gly Thr Leu Arg Phe Thr Arg Asp His Val Lys Ala
305                 310                 315                 320

Ile Val Leu Asp Thr Phe Ile Gly Ala Ile Asp Thr Ser Ser Val Thr
                325                 330                 335

Ile Leu Trp Ala Met Ser Glu Leu Met Arg Lys Pro Gln Val Leu Arg
            340                 345                 350

Lys Ala Gln Ala Glu Val Arg Ala Ala Val Gly Asp Asp Lys Pro Arg
    355                 360                 365

Val Asn Ser Glu Asp Ala Ala Lys Ile Pro Tyr Leu Lys Met Val Val
    370                 375                 380

Lys Glu Thr Leu Arg Leu His Pro Pro Ala Thr Leu Leu Val Pro Arg
385                 390                 395                 400

Glu Thr Met Arg Asp Thr Thr Ile Cys Gly Tyr Asp Val Pro Ala Asn
                405                 410                 415
```

```
Thr Arg Val Phe Val Asn Ala Trp Ala Ile Gly Arg Asp Pro Ala Ser
            420                 425                 430

Trp Pro Ala Pro Asp Glu Phe Asn Pro Asp Arg Phe Val Gly Ser Asp
            435                 440                 445

Val Asp Tyr Tyr Gly Ser His Phe Glu Leu Ile Pro Phe Gly Ala Gly
    450                 455                 460

Arg Arg Ile Cys Pro Gly Leu Thr Met Gly Glu Thr Asn Val Thr Phe
465             470                 475                 480

Thr Leu Ala Asn Leu Leu Tyr Cys Tyr Asp Trp Ala Leu Pro Gly Ala
            485                 490                 495

Met Lys Pro Glu Asp Val Ser Met Glu Glu Thr Gly Ala Leu Thr Phe
            500                 505                 510

His Arg Lys Thr Pro Leu Val Val Val Pro Thr Lys Tyr Lys Asn Arg
            515                 520                 525

Arg Ala Ala
    530

<210> SEQ ID NO 21
<211> LENGTH: 507
<212> TYPE: PRT
<213> ORGANISM: Musa acuminata
<220> FEATURE:
<221> NAME/KEY: misc_feature
<222> LOCATION: (1)..(507)
<223> OTHER INFORMATION: Public GI no. 17644125

<400> SEQUENCE: 21

Met Ala Leu Pro Pro Leu Leu Ser Pro Leu Pro Ser Leu Leu Val
1               5                   10                  15

Val Leu Ala Leu Leu Ser Ser Leu Leu Leu Ala Gly Arg Lys Ala Arg
            20                  25                  30

Gly Gly Ser Ala Thr Trp Lys Leu Pro Pro Gly Pro Pro Lys Leu Pro
            35                  40                  45

Val Ile Gly His Leu His Leu Gly Ser Ser Leu Leu His Arg Ser
    50                  55                  60

Leu Trp Glu Leu Ser Lys Lys His Gly Pro Leu Met His Leu Lys Phe
65                  70                  75                  80

Gly Arg Val Pro Val Val Val Ser Ser Pro Glu Met Ala Lys Glu
                85                  90                  95

Val Leu Lys Thr His Asp Leu Glu Cys Cys Ser Arg Pro Ser Leu Leu
            100                 105                 110

Ser Phe Ser Lys Phe Ser Tyr Gly Leu Ser Asp Val Ala Phe Ile Pro
        115                 120                 125

Tyr Gly Glu Arg Trp Arg Gln Leu Arg Lys Leu Cys Thr Val Glu Leu
    130                 135                 140

Leu Ser Thr Arg Lys Ile Asn Ser Phe Arg Asp Ile Arg Lys Glu Glu
145             150                 155                 160

Met Glu Arg Val Thr Lys Leu Ile Cys Ser His Val Arg Ala Ser Ser
                165                 170                 175

Met Val Asn Leu Ser Glu Leu Leu Ser Leu Ser Cys Asn Met Thr
            180                 185                 190

Cys Arg Ser Ala Phe Gly Ser Gly Phe Asp Asp Gly Gly Asp Ile Gln
        195                 200                 205

Leu His Asp Met Leu Arg Glu Ala Gln Glu Glu Leu Ser Gly Leu Phe
    210                 215                 220

Leu Ser Asp Tyr Leu Pro Leu Leu Gly Trp Val Asp Arg Leu Ser Gly
```

```
                    225                 230                 235                 240

Met Arg Ser Arg Leu Glu Arg Ala Phe Leu Lys Leu Asp Ser Ile Tyr
                245                 250                 255

Gln Arg Arg Ile Asp Tyr His Gln Asp Arg Leu Arg Gln Gln Gly Lys
            260                 265                 270

Glu Asp Gly Asp Val Leu Asp Ala Leu Leu Arg Met Gln Lys Asp Glu
        275                 280                 285

Glu Gly Leu Thr Glu Asp His Ile Lys Gly Val Leu Met Asp Ile Phe
    290                 295                 300

Ile Ala Gly Thr Asp Thr Ser Ser Ala Thr Val Glu Trp Ala Met Ala
305                 310                 315                 320

Glu Leu Ile Arg Gln Pro Glu Leu Met Lys Arg Ala Gln Asp Glu Val
                325                 330                 335

Arg Arg Cys Val Gly Ser Lys Gly Glu Val Glu Ser Asp Leu His
            340                 345                 350

Gln Leu His Phe Phe Lys Cys Val Ile Lys Glu Thr Met Arg Leu His
        355                 360                 365

Pro Pro Ala Pro Leu Leu Pro Arg Glu Thr Met Gln His Phe Lys
    370                 375                 380

Leu Asn Gly Tyr Asp Ile Leu Pro Lys Thr Trp Met Tyr Val Asn Ala
385                 390                 395                 400

Trp Ala Ile Gly Arg Asp Pro Asn Ser Trp Gly Arg Pro His Val Phe
                405                 410                 415

Asp Pro Glu Arg Phe Met His Asp Ser Thr Glu Ala Ser Gly Gln Asp
            420                 425                 430

Phe Lys Leu Ile Pro Phe Gly Glu Gly Arg Arg Ile Cys Pro Gly Lys
        435                 440                 445

Asn Leu Gly Met Leu Met Val Glu Leu Val Leu Ala Asn Leu Leu Tyr
    450                 455                 460

Ser Phe Asp Trp His Leu Pro Pro Gly Met Val Lys Glu Asp Ile Ser
465                 470                 475                 480

Met Glu Glu Ala Pro Gly Val Thr Val His Arg Glu Tyr Ala Leu Cys
                485                 490                 495

Leu Met Ala Thr Lys Tyr Asp Ala Thr Thr Ala
            500                 505

<210> SEQ ID NO 22
<211> LENGTH: 501
<212> TYPE: PRT
<213> ORGANISM: Asparagus officinalis
<220> FEATURE:
<221> NAME/KEY: misc_feature
<222> LOCATION: (1)..(501)
<223> OTHER INFORMATION: Public GI no. 13516748

<400> SEQUENCE: 22

Met Thr Val Ser Ile Thr Ala Ala Val Gln Leu Phe Leu Leu Leu
1               5                   10                  15

Leu Leu Leu Pro Leu Leu Phe Val His His Lys Thr Lys Pro Lys Thr
                20                  25                  30

Lys Cys Arg Ser Pro Pro Gly Pro Pro Leu Pro Val Ile Gly Asn
            35                  40                  45

Leu His Gln Leu Ser Leu Leu His Gln Ser Leu Tyr Arg Leu Ser
        50                  55                  60

Lys Ile His Gly Pro Ile Phe Lys Leu Ser Leu Gly Arg Val Pro Val
65                  70                  75                  80
```

-continued

```
Leu Val Ile Ser Ser Pro Ser Leu Ala Lys Gln Val Leu Lys Thr His
                 85                  90                  95

Asp Leu Ala Cys Cys Ser Arg Ala Ser Thr Val Ser Phe Lys Glu Tyr
            100                 105                 110

Thr Tyr Asp Gly Cys Asp Val Ala Gly Ala Pro Tyr Gly Asp Ser Trp
        115                 120                 125

Arg Asn Leu Arg Lys Ile Phe Val Leu Lys Leu Leu Ser Ser Lys Lys
    130                 135                 140

Leu Thr Ser Phe Arg Leu Val Gln Glu Glu Ile Glu Gly Met Ile
145                 150                 155                 160

Ser Ser Ile Arg Thr Arg Ser Asp Thr Asn Ala Thr Val Asn Ile Thr
                165                 170                 175

Glu Phe Val Val Arg Leu Ala Asn Asn Ile Thr Phe Arg Val Ala Phe
            180                 185                 190

Gly Tyr Arg Ser Glu Gly Glu Tyr Gly Glu Lys Ser Arg Phe Gln Arg
        195                 200                 205

Leu Leu Glu Ser Gly Asn Asp Thr Val Ala Ser Phe Tyr Val Gly Asp
    210                 215                 220

Tyr Phe Pro Gly Leu Gly Trp Leu Asp Lys Met Thr Gly Lys Leu Gly
225                 230                 235                 240

Lys Met Lys Arg Asn Ala Arg Asp Leu Asp Glu Phe Tyr Gln Glu Val
                245                 250                 255

Ile Asp Ala His Met Lys Asp Gly Arg Lys Glu Asp Gly Lys Glu Asp
            260                 265                 270

Ile Val Asp Val Leu Leu Arg Leu Arg Glu Glu Gly Gln Leu Thr Met
        275                 280                 285

Asp His Ile Lys Gly Ala Leu Met Asn Ile Phe Val Gly Gly Thr Asp
    290                 295                 300

Thr Ser Ala Ala Ser Ile Ala Trp Ala Met Ala Glu Leu Ala Arg Lys
305                 310                 315                 320

Pro Lys Val Met Lys Lys Ala Gln Glu Glu Val Arg Lys Ala Ala Ser
                325                 330                 335

Lys Lys Gly Lys Val Glu Glu Asn Asp Leu Ala Gln Leu Gln Tyr Ile
            340                 345                 350

Lys Cys Val Val Asn Glu Thr Leu Arg Leu His Leu Pro Leu Pro Leu
        355                 360                 365

Leu Val Pro Arg Glu Thr Ile Gln His Cys Glu Ile Asn Gly Tyr Asp
    370                 375                 380

Val Ser Ala Lys Thr Arg Val Leu Val Asn Ala Trp Ala Ile Gly Arg
385                 390                 395                 400

Asp Glu Asp Ala Trp Glu Asn Pro Glu Glu Phe Asn Pro Asp Arg Phe
                405                 410                 415

Val Gly Ser Ser Leu Asp Tyr Lys Gly Gln Asp Phe Gln Phe Ile Pro
            420                 425                 430

Phe Gly Ala Gly Arg Arg Ile Cys Pro Gly Ile Gln Phe Gly Val Glu
        435                 440                 445

Thr Val Glu Leu Ala Leu Ala Asn Leu Leu Tyr Ala Phe Asn Trp Glu
    450                 455                 460

Leu Pro Pro Gly Val Glu Arg Glu Asn Ile Asp Met His Glu Ala Pro
465                 470                 475                 480

Gly Leu Val Thr Arg Arg Ala Thr Asp Leu Arg Leu Val Ala Thr Asn
                485                 490                 495
```

Tyr Glu Glu Ala Asn
            500

<210> SEQ ID NO 23
<211> LENGTH: 501
<212> TYPE: PRT
<213> ORGANISM: Asparagus officinalis
<220> FEATURE:
<221> NAME/KEY: misc_feature
<222> LOCATION: (1)..(501)
<223> OTHER INFORMATION: Public GI no. 13516750

<400> SEQUENCE: 23

Met Thr Val Ser Ile Thr Ala Ala Val Gln Leu Phe Leu Leu Leu Leu
1               5                   10                  15

Leu Leu Leu Gln Leu Leu Phe Val His His Lys Thr Lys Pro Lys Thr
            20                  25                  30

Lys Cys Arg Ser Pro Gly Pro Pro Leu Pro Val Ile Gly Asn
        35                  40                  45

Leu His Gln Leu Ser Leu Leu His Gln Ser Leu Tyr Arg Leu Ser
    50                  55                  60

Lys Ile His Gly Pro Ile Phe Lys Leu Ser Leu Gly Arg Val Pro Val
65                  70                  75                  80

Leu Val Ile Ser Ser Pro Ser Leu Ala Lys Gln Val Leu Lys Thr His
                85                  90                  95

Asp Leu Ala Phe Cys Ser Arg Ala Ser Thr Val Ser Phe Lys Glu Tyr
            100                 105                 110

Thr Tyr Asp Gly Cys Asp Val Ala Gly Ala Pro Tyr Gly Asp Ser Trp
        115                 120                 125

Arg Asn Leu Arg Lys Ile Phe Val Leu Asn Leu Ser Ser Lys Lys
    130                 135                 140

Leu Thr Ser Phe Arg Leu Val Gln Glu Glu Ile Glu Gly Met Ile
145                 150                 155                 160

Ser Ser Ile Arg Thr Arg Ser Asp Thr Asn Ala Thr Val Asn Ile Thr
                165                 170                 175

Glu Phe Val Val Arg Leu Ala Asn Asn Ile Thr Phe Arg Val Ala Phe
            180                 185                 190

Gly Tyr Arg Ser Glu Gly Glu Tyr Gly Glu Lys Ser Arg Phe Gln Arg
        195                 200                 205

Leu Leu Glu Ser Gly Asn Asp Thr Val Ala Ser Phe Tyr Val Gly Asp
    210                 215                 220

Tyr Phe Pro Gly Leu Gly Trp Leu Asp Lys Ile Thr Gly Lys Leu Gly
225                 230                 235                 240

Lys Met Lys Arg Asn Ala Arg Asp Leu Asp Glu Phe Tyr Gln Glu Val
                245                 250                 255

Ile Asp Ala His Met Lys Asp Gly Arg Lys Glu Asp Gly Lys Glu Asp
            260                 265                 270

Ile Val Asp Val Leu Leu Arg Leu Arg Glu Glu Gly Gln Leu Thr Met
        275                 280                 285

Asp His Ile Lys Gly Ala Leu Met Asn Ile Phe Val Gly Gly Thr Asp
    290                 295                 300

Thr Ser Ala Ala Ser Ile Ala Trp Ala Met Ala Glu Leu Ala Arg Lys
305                 310                 315                 320

Pro Lys Val Met Lys Lys Ala Gln Glu Glu Val Arg Lys Ala Ala Ser
                325                 330                 335

Lys Lys Gly Lys Val Glu Glu Asn Asp Leu Ala Gln Leu Gln Tyr Ile

```
                340             345             350
Lys Cys Val Val Asn Glu Thr Leu Arg Leu His Leu Pro Leu Pro Leu
            355                 360                 365

Leu Val Pro Arg Glu Thr Ile Gln His Cys Glu Ile Asn Gly Tyr Asp
        370                 375                 380

Val Ser Ala Lys Thr Arg Val Leu Val Asn Ala Trp Ala Ile Gly Arg
385                 390                 395                 400

Asp Glu Asp Ala Trp Glu Asn Pro Glu Phe Asn Pro Asp Arg Phe
                405                 410                 415

Val Gly Ser Ser Leu Asp Tyr Lys Gly Gln Asp Phe Gln Phe Ile Pro
            420                 425                 430

Phe Gly Ala Gly Arg Arg Ile Cys Pro Gly Ile Gln Phe Gly Val Glu
            435                 440                 445

Thr Val Glu Leu Ala Leu Ala Asn Leu Leu Tyr Ala Phe Asn Trp Glu
        450                 455                 460

Leu Pro Pro Gly Val Arg Glu Asn Ile Asp Met His Glu Ala Pro
465                 470                 475                 480

Gly Leu Val Thr Arg Arg Ala Thr Asp Leu Arg Leu Val Ala Thr Asn
            485                 490                 495

Tyr Glu Glu Ala Asn
            500

<210> SEQ ID NO 24
<211> LENGTH: 496
<212> TYPE: PRT
<213> ORGANISM: Thlaspi arvense
<220> FEATURE:
<221> NAME/KEY: misc_feature
<222> LOCATION: (1)..(496)
<223> OTHER INFORMATION: Public GI no. 1345641

<400> SEQUENCE: 24

Met Asp Leu Leu Tyr Ile Val Ala Ala Leu Val Ile Phe Ala Ser Leu
1               5                   10                  15

Leu Ile Ala Lys Ser Lys Arg Lys Pro Lys Lys Asn Leu Pro Pro Gly
            20                  25                  30

Pro Pro Arg Leu Pro Ile Ile Gly Asn Leu His Gln Leu Gly Glu Lys
        35                  40                  45

Pro His Arg Ala Met Val Glu Leu Ser Lys Thr Tyr Gly Pro Leu Met
    50                  55                  60

Ser Leu Lys Leu Gly Ser Val Thr Thr Val Ala Thr Ser Val Glu
65                  70                  75                  80

Thr Val Arg Asp Val Leu Lys Thr Tyr Asp Leu Glu Cys Cys Ser Arg
                85                  90                  95

Pro Tyr Met Thr Tyr Pro Ala Arg Ile Thr Tyr Asn Leu Lys Asp Leu
            100                 105                 110

Val Phe Ser Pro Tyr Asp Lys Tyr Trp Arg Gln Val Arg Lys Leu Thr
        115                 120                 125

Val Val Glu Leu Tyr Thr Ala Lys Arg Val Gln Ser Phe Arg His Ile
    130                 135                 140

Arg Glu Glu Glu Val Ala Ser Phe Val Arg Phe Asn Lys Gln Ala Ala
145                 150                 155                 160

Ser Ser Glu Glu Thr Val Asn Leu Ser Gln Lys Ile Leu Lys Met Ser
                165                 170                 175

Gly Ser Val Ile Cys Arg Ile Gly Phe Gly Ile Asn Leu Glu Gly Ser
            180                 185                 190
```

```
Lys Leu Glu Asn Thr Tyr Gln Glu Ile Ile Val Gln Ala Phe Glu Val
        195                 200                 205

Leu Gly Ser Leu Ala Ala Val Asp Tyr Phe Pro Val Ile Gly Thr Ile
210                 215                 220

Ile Asp Arg Ile Thr Gly Leu His Ala Lys Cys Glu Lys Val Phe His
225                 230                 235                 240

Gly Ile Asp Ser Phe Phe Asp Gln Ala Ile Gln Arg His Ile Asp Asp
                245                 250                 255

Pro Ser Ile Lys Asp Asp Ile Ile Asp Leu Leu Leu Lys Met Glu Arg
            260                 265                 270

Gly Glu Gly Ser Leu Gly Glu Tyr Glu Leu Thr Arg Glu His Thr Lys
        275                 280                 285

Gly Ile Leu Met Asn Ile Leu Thr Ala Gly Ile Asp Thr Ser Ala Gln
    290                 295                 300

Thr Met Thr Trp Ala Met Thr His Leu Leu Ala Asn Pro Arg Val Met
305                 310                 315                 320

Lys Lys Leu Gln Ala Glu Ile Arg Glu Lys Ile Lys Asn Ile Asp Glu
                325                 330                 335

Ile Thr Asp Asp Asp Val Glu Gln Leu Asp Tyr Phe Lys Leu Val Leu
            340                 345                 350

Lys Glu Thr Phe Arg Ile Ser Pro Ile Val Pro Val Leu Val Pro Arg
        355                 360                 365

Val Ala Ala Lys Asp Leu Lys Ile Ala Gly Tyr Asp Val Pro Glu Lys
    370                 375                 380

Thr Trp Ile His Val Asn Met Trp Ala Val His Met Ser Pro Ser Ile
385                 390                 395                 400

Trp Lys Asp Pro Glu Thr Phe Asn Pro Glu Arg Phe Ile Asp Asn Gln
                405                 410                 415

Thr Asp Phe Lys Gly Leu Asn Phe Glu Leu Leu Pro Phe Gly Ser Gly
            420                 425                 430

Arg Arg Met Cys Pro Gly Met Gly Met Gly Leu Ala Val Val His Leu
        435                 440                 445

Thr Leu Ile Asn Leu Leu Tyr Arg Phe Asp Trp Lys Leu Pro Asn Gly
    450                 455                 460

Met Lys Ala Glu Glu Leu Ser Ile Glu Glu Asn Tyr Gly Leu Ile Cys
465                 470                 475                 480

Val Lys Lys Leu Pro Leu Glu Ala Ile Pro Val Leu Thr Gln Trp Thr
                485                 490                 495

<210> SEQ ID NO 25
<211> LENGTH: 538
<212> TYPE: PRT
<213> ORGANISM: Oryza sativa
<220> FEATURE:
<221> NAME/KEY: misc_feature
<222> LOCATION: (1)..(538)
<223> OTHER INFORMATION: Public GI no. 50936051

<400> SEQUENCE: 25

Met Ala Asp Asp Phe Leu Ser Ser Gln Pro Gln Pro Trp Pro Pro Leu
1               5                   10                  15

Leu Gln Leu Ser Ala Ala Val Leu Phe Phe Leu Leu Pro Leu Leu Tyr
            20                  25                  30

Leu Leu Phe Leu Arg Gly Ser Asn Gly Glu Val Arg Gly Arg Gln Gly
        35                  40                  45
```

```
Asn Ser Ala Ser Ala Pro Ser Leu Pro Gly Pro Cys Arg Gln Leu Pro
    50                  55                  60

Val Leu Gly Asn Leu Leu Gln Ile Gly Ser Arg Pro His Arg Tyr Phe
 65                  70                  75                  80

Gln Ala Val Ser Arg Arg Tyr Gly Pro Val Gln Val Gln Leu Gly
                 85                  90                  95

Gly Val Arg Thr Val Val His Ser Pro Glu Ala Ala Glu Asp Val
                100                 105                 110

Leu Arg Thr Asn Asp Val His Cys Cys Ser Arg Pro Pro Ser Pro Gly
                115                 120                 125

Pro Arg Met Leu Ser Tyr Asn Tyr Leu Asp Val Ala Phe Ala Pro Tyr
    130                 135                 140

Ser Asp Tyr Trp Arg Glu Met Arg Lys Leu Phe Val Val Glu Leu Thr
145                 150                 155                 160

Ser Val Ser Arg Val Arg Ser Phe Ala Tyr Ala Arg Ala Ala Glu Val
                165                 170                 175

Ala Arg Leu Val Asp Thr Leu Ala Ala Ser Pro Pro Gly Val Pro Val
                180                 185                 190

Asp Leu Ser Cys Ala Leu Tyr Gln Leu Leu Asp Gly Ile Ile Gly Thr
                195                 200                 205

Val Ala Phe Gly Lys Gly Tyr Gly Ala Ala Gln Trp Ser Thr Glu Arg
    210                 215                 220

Ala Val Phe Gln Asp Val Leu Ser Glu Leu Leu Val Leu Gly Ser
225                 230                 235                 240

Phe Ser Phe Glu Asp Phe Phe Pro Ser Ser Ala Leu Ala Arg Trp Ala
                245                 250                 255

Asp Ala Leu Ala Gly Val Glu Arg Arg Arg Arg Ile Phe Arg Gln
                260                 265                 270

Val Asp Gly Phe Leu Asp Ser Val Ile Asp Lys His Leu Glu Pro Glu
                275                 280                 285

Arg Leu Ser Ala Gly Val Gln Glu Asp Met Val Asp Ala Leu Val Lys
    290                 295                 300

Met Trp Arg Glu Gln Gln Asp Arg Pro Ser Gly Val Leu Thr Arg Glu
305                 310                 315                 320

His Ile Lys Ala Ile Leu Met Asn Thr Phe Ala Gly Gly Ile Asp Thr
                325                 330                 335

Thr Ala Ile Thr Ala Ile Trp Ile Met Ser Glu Ile Met Arg Asn Pro
                340                 345                 350

Arg Val Met Gln Lys Ala Arg Ala Glu Val Arg Asn Thr Val Lys Asn
    355                 360                 365

Lys Pro Leu Val Asp Glu Glu Asp Ser Gln Asn Leu Lys Tyr Leu Glu
    370                 375                 380

Met Ile Ile Lys Glu Asn Phe Arg Leu His Pro Pro Gly Asn Leu Leu
385                 390                 395                 400

Val Pro Arg Gln Thr Met Gln Pro Cys Leu Ile Gly Gly Tyr Asn Val
                405                 410                 415

Pro Ser Gly Thr Arg Val Phe Ile Asn Ile Trp Ala Met Gly Arg Gly
                420                 425                 430

Pro Met Ile Trp Asp Asn Pro Glu Glu Phe Tyr Pro Glu Arg Phe Glu
                435                 440                 445

Asp Arg Asn Met Asp Phe Arg Gly Ser Asn Phe Glu Leu Val Pro Phe
    450                 455                 460

Gly Ser Gly Arg Arg Ile Cys Pro Gly Val Ala Met Ala Val Thr Ser
```

```
                         465                 470                 475                 480
Leu Glu Leu Val Val Ala Asn Leu Leu Tyr Cys Phe Asp Trp Lys Leu
                    485                 490                 495

Pro Lys Gly Met Lys Glu Glu Asp Ile Asp Met Glu Glu Ile Gly Gln
                500                 505                 510

Ile Ser Phe Arg Arg Lys Val Glu Leu Phe Ile Val Pro Val Lys His
            515                 520                 525

Glu Gln Tyr Gln Leu Met Gly His Ile Asn
        530                 535

<210> SEQ ID NO 26
<211> LENGTH: 494
<212> TYPE: PRT
<213> ORGANISM: Ammi majus
<220> FEATURE:
<221> NAME/KEY: misc_feature
<222> LOCATION: (1)..(494)
<223> OTHER INFORMATION: Public GI no. 46947673

<400> SEQUENCE: 26

Met Lys Met Leu Glu Gln Asn Pro Gln Tyr Leu Tyr Phe Phe Ser Leu
1               5                  10                  15

Phe Leu Val Thr Ile Phe Leu Tyr Lys Trp Leu Thr Leu Lys Lys Thr
                20                  25                  30

Pro Leu Lys Asn Leu Pro Pro Ser Pro Pro Gln Tyr Pro Ile Ile Gly
            35                  40                  45

Asn Leu His Gln Ile Gly Pro Asp Pro Gln Ala Ser Leu Arg Asp Leu
        50                  55                  60

Ala Gln Lys Tyr Gly Pro Leu Met Phe Leu Lys Phe Gly Thr Val Pro
65                  70                  75                  80

Val Leu Val Val Ser Ser Ala Asp Ala Ala Arg Glu Ala Leu Lys Thr
                85                  90                  95

His Asp Leu Val Phe Ala Asp Arg Pro Tyr Ser Ser Val Ala Asn Lys
                100                 105                 110

Ile Phe Tyr Asn Gly Lys Asp Met Val Phe Ala Arg Tyr Thr Glu Tyr
            115                 120                 125

Trp Arg Gln Val Lys Ser Ile Cys Val Thr Gln Leu Leu Ser Asn Lys
        130                 135                 140

Arg Val Asn Ser Phe His Tyr Val Arg Glu Glu Val Asp Leu Leu
145                 150                 155                 160

Val Gln Asn Leu Glu Asn Ser His Ser Lys Val Ala Asn Leu Thr Glu
                165                 170                 175

Leu Leu Ile Glu Val Thr Gly Asn Val Val Cys Arg Val Ser Val Gly
                180                 185                 190

Ser Gly Asp Lys Val Asp Ser Tyr Lys Ile Leu Ile Leu Glu Ile Met
            195                 200                 205

Asp Met Leu Gly Tyr Ser Arg Ser Ile Glu Asp Phe Phe Pro Leu Leu
        210                 215                 220

Gly Trp Val Asp Trp Leu Thr Gly Leu Arg Gly Lys Val Ala Glu Ala
225                 230                 235                 240

Ala Lys Gly Val Asp Thr Phe Leu Glu Gly Val Leu Lys Glu His Leu
                245                 250                 255

Ser Thr Thr Gly Ser Lys Tyr Asn Asp Phe Val Ser Ile Leu Leu Glu
                260                 265                 270

Ile Gln Glu Ala Asp Ala Gly Ser Ser Met Asp Asn Glu Cys Ile Lys
            275                 280                 285
```

```
Ser Leu Ile Trp Asp Met Leu Gly Ala Gly Thr Glu Thr Ile Ser Thr
    290                 295                 300
Ala Leu Glu Trp Thr Leu Ala Ala Leu Ile Lys Asn Pro Asp Ala Met
305                 310                 315                 320
Phe Lys Leu Gln Asn Glu Val Arg Glu Ile Gly Lys Gly Lys Ser Lys
                325                 330                 335
Ile Ser Glu Ala Asp Leu Val Lys Met Asn Tyr Leu Gln Ala Val Met
            340                 345                 350
Lys Glu Ser Met Arg Leu Tyr Phe Thr Ala Pro Leu Leu Val Pro Arg
        355                 360                 365
Glu Ala Arg Gln Asp Ile Lys Phe Met Gly Tyr Asp Ile Ser Ser Gly
    370                 375                 380
Thr Gln Val Leu Ile Asn Ala Trp Ala Ile Ala Arg Asp Pro Leu Leu
385                 390                 395                 400
Trp Asp Lys Pro Glu Glu Phe Arg Pro Glu Arg Phe Leu Asn Ser Pro
                405                 410                 415
Ile Asp Tyr Lys Gly Phe His Tyr Glu Phe Leu Pro Phe Gly Ala Gly
            420                 425                 430
Arg Arg Gly Cys Pro Gly Ile Gln Phe Ala Met Cys Ile Asn Glu Leu
        435                 440                 445
Val Val Ala Asn Leu Val His Lys Phe Asn Phe Glu Leu Pro Asp Gly
    450                 455                 460
Lys Arg Leu Glu Asp Leu Asp Met Thr Ala Ala Ser Gly Ile Thr Leu
465                 470                 475                 480
Arg Lys Lys Ser Pro Leu Leu Val Val Ala Arg Pro His Val
                485                 490

<210> SEQ ID NO 27
<211> LENGTH: 509
<212> TYPE: PRT
<213> ORGANISM: Nepeta racemosa
<220> FEATURE:
<221> NAME/KEY: misc_feature
<222> LOCATION: (1)..(509)
<223> OTHER INFORMATION: Public GI no. 3582021

<400> SEQUENCE: 27

Met Val Ser Leu Ser Tyr Phe Leu Ile Ala Leu Leu Cys Thr Leu Pro
1               5                   10                  15
Phe Leu Leu Phe Leu Asn Lys Trp Arg Arg Ser Tyr Ser Gly Lys Thr
                20                  25                  30
Pro Pro Pro Ser Pro Pro Lys Leu Pro Val Ile Gly Asn Leu His Gln
            35                  40                  45
Leu Gly Leu Tyr Pro His Arg Tyr Leu Gln Ser Leu Ser Arg Arg Tyr
    50                  55                  60
Gly Pro Leu Met Gln Leu His Phe Gly Ser Val Pro Val Leu Val Ala
65                  70                  75                  80
Ser Ser Pro Glu Ala Ala Arg Glu Ile Met Lys Asn Gln Asp Ile Val
                85                  90                  95
Phe Ser Asn Arg Pro Lys Met Ser Ile Ala Asn Arg Leu Phe Phe Asn
            100                 105                 110
Asn Arg Asp Val Ala Phe Thr Gln Tyr Gly Glu Tyr Trp Arg Gln Ile
        115                 120                 125
Arg Ser Ile Cys Val Leu Gln Leu Leu Ser Asn Lys Arg Val Gln Ser
    130                 135                 140
```

```
Phe Arg Arg Val Arg Glu Glu Thr Ser Ile Met Val Glu Lys Ile
145                 150                 155                 160

Met Gln Leu Gly Ser Ser Ser Thr Pro Val Asn Leu Ser Glu Leu
            165                 170                 175

Leu Leu Ser Leu Thr Asn Asp Val Val Cys Arg Val Thr Leu Gly Lys
        180                 185                 190

Lys Tyr Gly Gly Gly Asn Gly Ser Glu Glu Val Asp Lys Leu Lys Glu
    195                 200                 205

Met Leu Thr Glu Ile Gln Asn Leu Met Gly Ile Ser Pro Val Trp Glu
210                 215                 220

Phe Ile Pro Trp Leu Asn Trp Thr Arg Arg Phe Asp Gly Val Asp Gln
225                 230                 235                 240

Arg Val Asp Arg Ile Val Lys Ala Phe Asp Gly Phe Leu Glu Ser Val
                245                 250                 255

Ile Gln Glu His Lys Glu Arg Asp Gly Asp Lys Asp Gly Asp Gly Asp
            260                 265                 270

Gly Ala Leu Asp Phe Val Asp Ile Leu Leu Gln Phe Gln Arg Glu Asn
        275                 280                 285

Lys Asn Arg Ser Pro Val Glu Asp Asp Thr Val Lys Ala Leu Ile Leu
    290                 295                 300

Asp Met Phe Val Ala Gly Thr Asp Thr Thr Ala Thr Ala Leu Glu Trp
305                 310                 315                 320

Ala Val Ala Glu Leu Ile Lys Asn Pro Arg Ala Met Lys Arg Leu Gln
                325                 330                 335

Asn Glu Val Arg Glu Val Ala Gly Ser Lys Ala Glu Ile Glu Glu Glu
            340                 345                 350

Asp Leu Glu Lys Met Pro Tyr Leu Lys Ala Ser Ile Lys Glu Ser Leu
        355                 360                 365

Arg Leu His Val Pro Val Leu Leu Val Pro Arg Glu Ser Thr Arg
    370                 375                 380

Asp Thr Asn Val Leu Gly Tyr Asp Ile Ala Ser Gly Thr Arg Val Leu
385                 390                 395                 400

Ile Asn Ala Trp Ala Ile Ala Arg Asp Pro Ser Val Trp Glu Asn Pro
                405                 410                 415

Glu Glu Phe Leu Pro Glu Arg Phe Leu Asp Ser Ser Ile Asp Tyr Lys
            420                 425                 430

Gly Leu His Phe Glu Leu Leu Pro Phe Gly Ala Gly Arg Arg Gly Cys
        435                 440                 445

Pro Gly Ala Thr Phe Ala Val Ala Ile Asp Glu Leu Ala Leu Ala Lys
    450                 455                 460

Leu Val His Lys Phe Asp Phe Gly Leu Pro Asn Gly Ala Arg Met Glu
465                 470                 475                 480

Glu Leu Asp Met Ser Glu Thr Ser Gly Met Thr Val His Lys Lys Ser
                485                 490                 495

Pro Leu Leu Leu Leu Pro Ile Pro His His Ala Ala Pro
            500                 505

<210> SEQ ID NO 28
<211> LENGTH: 503
<212> TYPE: PRT
<213> ORGANISM: Muscari armeniacum
<220> FEATURE:
<221> NAME/KEY: misc_feature
<222> LOCATION: (1)..(503)
<223> OTHER INFORMATION: Public GI no. 46409049
```

<400> SEQUENCE: 28

```
Met Ser Phe Thr Asp His His Tyr Leu Leu Ile Leu Phe Leu Ile
1               5                   10                  15

Pro Ile Leu Val Tyr Thr Ile Arg Arg Lys Ile Ser Ser Thr Lys Ser
            20                  25                  30

Lys Leu Pro Pro Cys Pro Pro Lys Leu Pro Leu Ile Gly Asn Leu His
            35                  40                  45

Gln Met Gly Thr Leu Pro His Gln Ser Leu His Ala Leu Ser Val Lys
    50                  55                  60

Tyr Gly Pro Leu Met Leu Leu Lys Leu Gly Gln Ile Pro Thr Leu Ile
65                  70                  75                  80

Val Ser Ser Ala Asp Met Ala Arg Glu Ile Met Lys Thr His Asp His
                85                  90                  95

Ile Phe Ala Ser Arg Pro Ser Leu Met Thr Ala Gly Ile Ile Leu Tyr
            100                 105                 110

Gly Ser Met Asp Val Val Phe Ala Pro Tyr Gly Glu His Trp Arg Gln
            115                 120                 125

Met Arg Lys Leu Cys Val Asn His Leu Leu Ser Pro Lys Ala Val Gln
130                 135                 140

Ser Phe Arg Arg Met His Glu Glu Val Ala Thr Met Val Ala Lys
145                 150                 155                 160

Ile Ser Glu Val Ser Ser Ser Gly Val Val Asn Met Ser Glu Thr
            165                 170                 175

Leu Asn Leu Phe Ala Ser Asn Ala Met Leu Lys Ala Ile Ser Arg Lys
            180                 185                 190

Leu Phe Arg Asp Glu Arg Arg Ser Arg Val Ile Cys Glu Leu Asn Glu
            195                 200                 205

Glu Thr Ala Ala Ile Leu Gly Gln Phe Ser Val Ser Asp Phe Met Pro
            210                 215                 220

Leu Leu Ala Trp Phe Asp Met Val Phe Gly Val Gly Ala Arg Ala Lys
225                 230                 235                 240

Lys Thr Ala Arg Leu Trp Asp Arg Val Leu His Glu Ile Ile Glu Asp
            245                 250                 255

Cys Arg Asn Arg Arg Asp Ser Glu Val Asn Thr Asp Phe Val Asn Val
            260                 265                 270

Leu Leu Ala Leu Leu Glu Asp Asn Asp Met Asp Phe Ser Leu Asn Lys
            275                 280                 285

Asp Ile Ile Lys Ala Val Leu Gln Asp Met Ile Ala Ala Gly Thr Glu
            290                 295                 300

Thr Ser Ser Thr Ala Met Asp Trp Cys Met Ala Glu Leu Val Arg Asn
305                 310                 315                 320

Pro Glu Ala Met Lys Lys Leu Gln Asp Glu Val Arg Gly Ile Ala Asn
            325                 330                 335

Thr Lys Pro Met Ile Thr Asp Asp Leu Ser Lys Met Gly Tyr Leu
            340                 345                 350

Lys Ala Val Ile Lys Glu Leu Leu Arg Leu His Pro Val Pro Leu
            355                 360                 365

Leu Ile Pro Arg Glu Ser Met Asp His Cys Glu Val Gln Gly Phe Asp
            370                 375                 380

Ile Pro Lys Gln Thr Arg Val Ile Val Asn Ala Trp Ser Ile Gly Arg
385                 390                 395                 400

Asp Pro Asn Val Trp Glu Ala Pro Glu Glu Phe Arg Pro Glu Arg Phe
            405                 410                 415
```

```
Leu Asp Cys Ala Ile Asn Phe Arg Gly His Asp Phe Glu Leu Ile Pro
            420                 425                 430

Phe Gly Ala Gly Arg Arg Ile Cys Pro Gly Met Gln Phe Ala Val Ser
        435                 440                 445

Thr Leu Glu Leu Ala Leu Ala Asn Leu Val Arg Ser Phe Asp Trp Glu
    450                 455                 460

Leu Pro Asp Gly Met Asn Asn Glu Asp Leu Gly Met Gly Asp Gly Pro
465                 470                 475                 480

Gly Leu Ser Ala Arg Arg Arg Gln Ser Leu Leu Leu Val Ala Lys Pro
            485                 490                 495

Phe Leu Gly Leu Lys Cys Met
            500
```